(12) United States Patent
Jin et al.

(10) Patent No.: US 10,085,983 B2
(45) Date of Patent: Oct. 2, 2018

(54) AZABICYCLO DERIVATIVES, PROCESS FOR PREPARATION THEREOF AND MEDICAL USE THEREOF

(71) Applicants: Shanghai Haiyan Pharmaceutical Technology Co., Ltd., Pudong New Area Shanghai (CN); Yangtze River Pharmaceutical Group Co., Ltd., Taizhou, Jiangsu (CN)

(72) Inventors: Yunzhou Jin, Pudong New Area Shanghai (CN); Ping Bu, Pudong New Area Shanghai (CN); Qi He, Pudong New Area Shanghai (CN); Jiong Lan, Pudong New Area Shanghai (CN); Fusheng Zhou, Pudong New Area Shanghai (CN); Liang Zhang, Pudong New Area Shanghai (CN); Xiangyu He, Pudong New Area Shanghai (CN)

(73) Assignees: Shanghai Haiyan Pharmaceutical Technology Co., Ltd., Shanghai (CN); Yangtze River Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 15/515,767

(22) PCT Filed: Sep. 24, 2015

(86) PCT No.: PCT/CN2015/090568
§ 371 (c)(1),
(2) Date: Mar. 30, 2017

(87) PCT Pub. No.: WO2016/050165
PCT Pub. Date: Apr. 7, 2016

(65) Prior Publication Data
US 2017/0296537 A1    Oct. 19, 2017

(30) Foreign Application Priority Data

Sep. 30, 2014    (CN) .......................... 2014 1 0520700

(51) Int. Cl.
| C07D 487/04 | (2006.01) |
| A61K 31/4985 | (2006.01) |
| A61K 31/53 | (2006.01) |
| A61K 31/4188 | (2006.01) |

(52) U.S. Cl.
CPC ...... *A61K 31/4985* (2013.01); *A61K 31/4188* (2013.01); *C07D 487/04* (2013.01)

(58) Field of Classification Search
None
See application file for complete search history.

(56) References Cited

U.S. PATENT DOCUMENTS

2016/0304471 A1* 10/2016 Qian ................ C07D 473/32

FOREIGN PATENT DOCUMENTS

| CN | 102482277 A | 5/2012 |
| CN | 103702990 A | 4/2014 |
| CN | 103717602 A | 4/2014 |
| WO | 2009102468 A1 | 8/2009 |
| WO | 2011079231 A1 | 6/2011 |
| WO | 2011140338 A1 | 11/2011 |
| WO | 2013042006 A1 | 3/2013 |
| WO | 2013170671 A1 | 11/2013 |

OTHER PUBLICATIONS

Qian et al. Chemical Abstract vol. 165, No. 336344 (Abstract for US 2016/133935) (2016).*
U.S. Appl. No. 62/117,442, filed Feb. 17, 2015.*
Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Simplicio et al. Molecules 2008, 13, 519-547.*
Galvani et al. Current Pharmaceutical Design, 2013, 19, 818-832.*
Noronha et al. OncoTargets and Therapy 2017:10 2903-2908.*
Int'l Search Report dated Dec. 28, 2015 in Int'l Application No. PCT/CN2015/090568.

* cited by examiner

*Primary Examiner* — Emily A Bernhardt
(74) *Attorney, Agent, or Firm* — Panitch Schwarze Belisario & Nadel LLP

(57) ABSTRACT

Azabicyclo derivatives, a preparation process, and medical use thereof are provided. In particular, azabicyclo derivatives of formula (I), pharmaceutically acceptable salts, stereoisomers, solvates and prodrugs thereof are described. The azabicyclo derivatives of formula (I) are useful as Epidermal Growth Factor Receptor (EGFR) inhibitors. The definitions of the variable R groups in the azabicyclo derivatives of formula (I) are described in the specification.

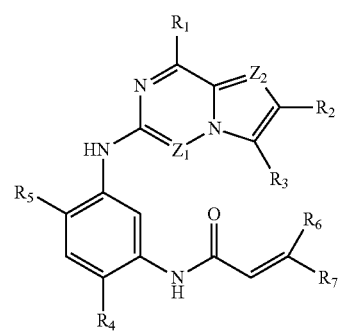

13 Claims, No Drawings

AZABICYCLO DERIVATIVES, PROCESS FOR PREPARATION THEREOF AND MEDICAL USE THEREOF

CROSS-REFERENCE TO RELATED APPLICATION

This application is a Section 371 of International Application No. PCT/CN2015/090568, filed Sep. 24, 2015, which was published in the Japanese language on Apr. 7, 2016 under International Publication No. WO 2016/050165 A1, and the disclosure of which is incorporated herein by reference.

TECHNICAL FIELD

The present invention relates to the field of medical technology, in particular to an azabicyclo derivative, preparation method thereof and use as an EGFR tyrosine kinase inhibitor, as well as pharmaceutical compositions and medicinal compositions prepared therefrom.

BACKGROUND ART

Lung cancer is a cancer having the highest incidence in the world. In China, the incidence of lung cancer ranks first among all cancers and it is also a cancer having the highest morbidity and mortality.

In Chinese patients with lung cancer, 30% of patients have the EGFR mutation, wherein L858R and exon 19 deletion mutations account for more than 90% and these patients are more sensitive to EGFR inhibitors. The existing first generation EGFR inhibitors in market such as erlotinib and gefitinib have good treatment effects on these patients and can make the tumors of more than 60% of the patients shrink, thereby significantly prolonging the progression-free survival of patients. However, drug-resistance develops within 6-12 months for the most majority of patients, and the first-generation EGFR inhibitors are no longer effective, while no drugs are available to these patients currently. It has been found in clinic that EGFR T790M mutation was present in 50% of the patients who developed resistance to the first-generation EGFR inhibitors. The first-generation EGFR inhibitors, erlotinib and gefitinib, were greater than 3 uM in the T790M mutant cell line H1975 and almost have no activity.

Currently the second-generation irreversible pan-EGFR inhibitor, alfatinib, has been approved for the market. This drug has significantly better treatment effect on patients with EGFR mutation lung cancer compared with the first-generation EGFR inhibitors. However, the second-generation inhibitors also have a strong inhibitory activity on wild-type EGFR. The inhibitory activity on wild-type EGFR is significantly higher than that on the resistant T790M mutation. The side effects such as rash and the like are serious and it has poor treatment effect on drug-resistant patients. Only a small proportion of the patients resistant to first-generation EGFR inhibitors respond to this kind of drugs.

In order to increase the inhibitory activity against EGFR T790M resistance mutant while reduce the inhibitory activity against wild-type EGFR, developing third-generation EGFR mutant selective inhibitors with higher activity, better selectivity and lower toxicity is of great significance.

SUMMARY OF THE INVENTION

The object of the present invention is to provide a novel class of azabicyclo derivatives which are low cytotoxic and have high selective inhibitory effect on EGFR mutants.

In the first aspect of the present invention, a compound represented by formula (I), or a pharmaceutically acceptable salt, solvate, stereoisomer, or prodrug thereof is provided,

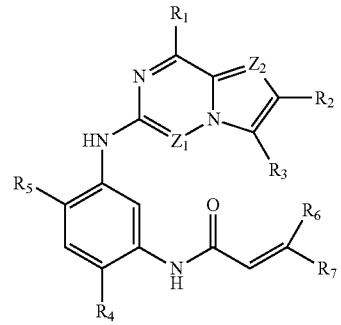

I wherein, $Z_1$ and $Z_2$ are each independently N or $CR_0$; wherein, $R_0$ is selected from the group consisting of H, halogen, $C_{1-10}$ alkyl (preferably $C_{1-6}$ alkyl, more preferably $C_{1-3}$ alkyl), $C_{1-10}$ haloalkyl (preferably $C_{1-6}$ haloalkyl, more preferably $C_{1-3}$ haloalkyl);

$R_1$ and $R_2$ are each independently H, halogen, $C_{1-10}$ alkyl (preferably $C_{1-6}$ alkyl, more preferably $C_{1-3}$ alkyl), $C_{1-10}$ haloalkyl (preferably $C_{1-6}$ alkyl, more preferably $C_{1-3}$ alkyl), $C_{1-10}$ alkoxy (preferably $C_{1-6}$ alkoxy, more preferably $C_{1-3}$ alkoxy), $C_{3-8}$ cycloalkoxy (preferably $C_{3-6}$ cycloalkoxy);

$R_3$ is H, halogen, $C^{2-10}$ alkenyl (preferably $C_{2-6}$ alkenyl), $C_{1-10}$ alkyl (preferably $C_{1-6}$ alkyl, more preferably $C_{1-3}$ alkyl), $C_{1-10}$ haloalkyl (preferably $C_{1-6}$ haloalkyl, more preferably $C_{1-3}$ haloalkyl), $C_{1-10}$ alkoxy (preferably $C_{1-6}$ alkoxy, more preferably $C_{1-3}$ alkoxy), $C_{3-8}$ cycloalkoxy (preferably $C_{3-6}$ cycloalkoxy), substituted or unsubstituted $C_{3-10}$ cycloalkyl (preferably $C_{3-6}$ cycloalkyl), substituted or unsubstituted $C_{3-10}$ heterocyclic radical, substituted or unsubstituted $C_{6-10}$ aromatic ring, substituted or unsubstituted $C_{4-10}$ cycloalkenyl;

$R_4$ is selected from the group consisting of:

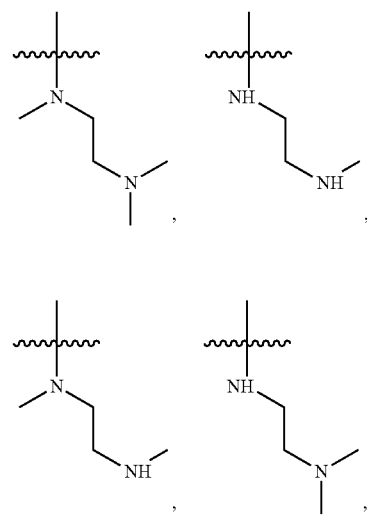

-continued

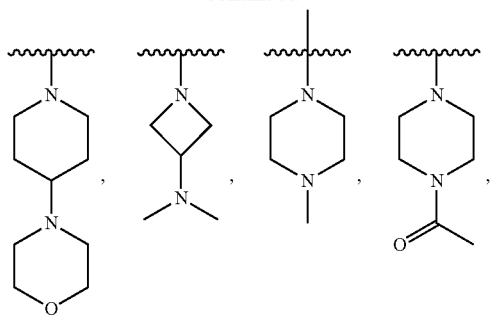
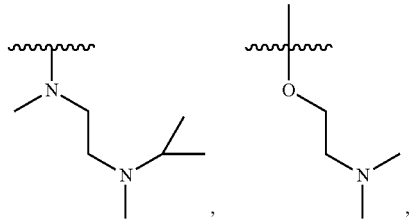

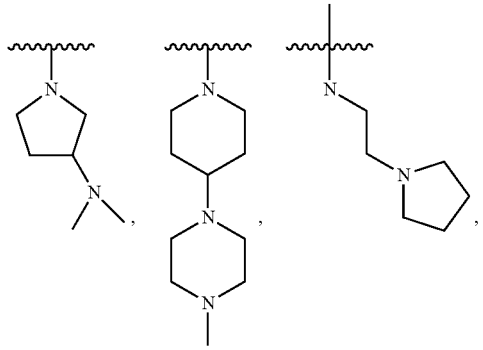
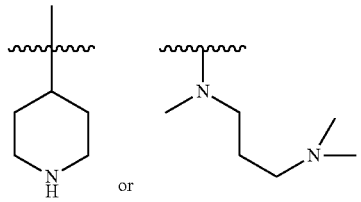

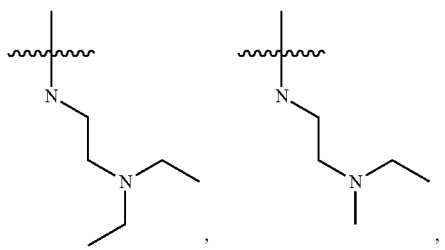

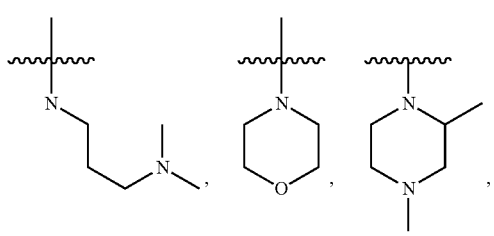

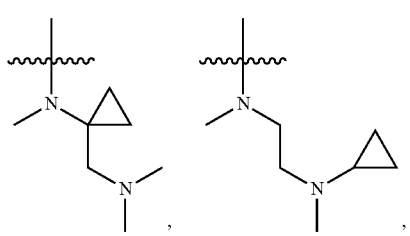

$R_5$ is H, hydroxy, CN, $NO_2$, halogen, $C_{1-10}$ alkyl (preferably $C_{1-6}$ alkyl, more preferably $C_{1-3}$ alkyl), $C_{1-10}$ haloalkyl (preferably $C_{1-6}$ haloalkyl, more preferably $C_{1-3}$ haloalkyl), $C_{1-10}$ alkoxy (preferably $C_{1-6}$ alkoxy, more preferably $C_{1-3}$ alkoxy), $C_{3-10}$ cycloalkyl (preferably $C_{3-6}$ cycloalkyl), $C_{3-8}$ cycloalkoxy (preferably $C_{3-6}$ cycloalkoxy), —$CON(C_{1-10}$ alkyl$)_2$ (preferably —$CON(C_{1-6}$ alkyl$)_2$, more preferably —$CON(C_{1-3}$ alkyl$)_2$), —$NC(O)C_{1-10}$ alkyl (preferably —$NC(O)C_{1-6}$ alkyl, more preferably —$NC(O)C_{1-3}$ alkyl), —$C(O)OC_{1-10}$ alkyl (preferably —$C(O)OC_{1-6}$ alkyl, more preferably —$C(O)OC_{1-3}$ alkyl), —$OC(O)C_{1-10}$ alkyl (preferably —$OC(O)C_{1-6}$ alkyl, more preferably —$OC(O)C_{1-3}$ alkyl), —$COC_{1-10}$ alkyl (preferably —$COC_{1-6}$ alkyl, more preferably —$COC_{1-3}$ alkyl), —CO-phenyl, —$SO_2C_{1-10}$ alkyl (preferably —$SO_2C_{1-6}$ alkyl, more preferably —$SO_2C_{1-3}$ alkyl), —$SO_2$-phenyl, —$S(O)C_{1-10}$ alkyl (preferably —$S(O)C_{1-6}$ alkyl, more preferably —$S(O)C_{1-3}$ alkyl), —S(O)-phenyl, —$N(C_{1-10}$ alkyl); (preferably —$N(C_{1-6}$ alkyl$)_2$, more preferably —$N(C_{1-3}$ alkyl$)_2$); wherein, said phenyl is unsubstituted or substituted with 1-3 substituents selected from the group consisting of halogen and $C_{1-10}$ alkyl;

$R_6$ and $R_7$ are each independently H, $C_{1-10}$ alkyl (preferably $C_{1-6}$ alkyl, more preferably $C_{1-3}$ alkyl, most preferably methyl), substituted or unsubstituted $C_{6-10}$ aryl;

wherein, said "substituted" means 1-6 hydrogen atoms on a ring atom are substituted with a substituent selected from the group consisting of: hydroxy, CN, $NO_2$, halogen, $C_{1-10}$ alkyl, $C_{1-10}$ haloalkyl, —$CON(C_{1-10}$ alkyl$)_2$, —$C(O)OC_{1-10}$ alkyl, —$OC(O)C_{1-10}$ alkyl, —$COC_{1-10}$ alkyl, —CO-phenyl, —$SO_2C_{1-10}$ alkyl, —$SO_2$-phenyl, —$S(O)C_{1-10}$ alkyl, —S(O)-phenyl, —$N(C_{1-10}$ alkyl$)_2$; wherein said phenyl is unsubstituted or substituted with 1-3 substituents selected from the group consisting of halogen, and $C_{1-10}$ alkyl.

In another preferred embodiment, said formula (I) compound is a compound represented by formula (I-a):

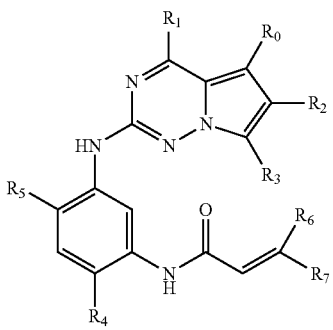

wherein, $R_0$, $R_1$, $R_2$, $R_3$, $R_4$, $R_5$, $R_6$, and $R_7$ are defined as above.

In another preferred embodiment, said formula (I) compound is a compound represented by formula (I-b):

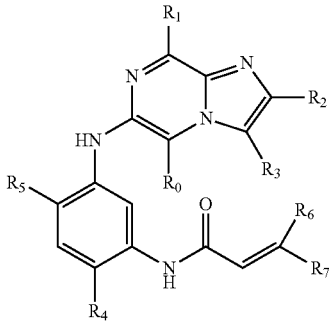

wherein, $R_0$, $R_1$, $R_2$, $R_3$, $R_4$, $R_5$, $R_6$, and $R_7$ are defined as above.

In another preferred embodiment, in formula (I-a) compound and/or formula (I-b) compound, $R_5$ is H, hydroxy, CN, $NO_2$, F, Cl, Br, I, methyl, ethyl, propyl, isopropyl, monofluoroethyl, difluoromethyl, trifluoromethyl, methoxy, ethoxy, propoxy, isopropoxy, cyclopropyloxy, cyclopropyl, cyclobutyl, cyclopentyl, cyclohexyl, —$CON(CH_3)_2$, —NC(O)$CH_3$, —C(O)O$CH_3$, —OC(O)$CH_3$, —CO-phenyl, —CO$CH_3$, —$SO_2$-phenyl, —$SO_2CH_3$, —$N(CH_3)_2$.

In another preferred embodiment, in formula (I-a) compound and/or formula (I-b) compound, $R_6$ and $R_7$ are H.

In another preferred embodiment, in formula (I-a) compound and/or foil (I-b) compound, $R_1$ and $R_2$ are H.

In another preferred embodiment, in formula (I-a) compound and/or foil (I-b) compound, $R_3$ is:

(i) substituted or unsubstituted 9-10 membered bicyclic heteroaryl containing 1, 2 or 3 nitrogen atoms;

(ii) substituted or unsubstituted 5-6 membered monocyclic heteroaryl containing 1-2 nitrogen atoms;

(iii) substituted or unsubstituted 4-7 membered saturated mono-heterocyclic radical containing 1 or 2 heteroatoms selected from N, O or S;

(iv) substituted or unsubstituted 6 membered partially unsaturated monocyclic group;

(v) substituted or unsubstituted $C_{6-10}$ aryl;

(vi) $C_{1-3}$ alkyl; or (vii) $C_{3-10}$ cycloalkyl.

In another preferred embodiment, said "substituted" means 1-3 hydrogen atoms on a ring atom is unsubstituted with a substituent selected from the group consisting of: hydroxy; $NO_2$, halogen, $C_{1-3}$ alkyl, $C_{1-3}$ haloalkyl, —$SO_2C_{1-3}$ alkyl, —$COC_{1-3}$ alkyl.

In another preferred embodiment, said "substituted" means 1-3 hydrogen atoms on a ring atom is unsubstituted with a substituent selected from the group consisting of: hydroxy, $NO_2$, F, Cl, Br, I, methyl, ethyl, propyl, isopropyl, monofluoroethyl, difluoromethyl, trifluoromethyl, —$COCH_3$, —$SO_2CH_3$.

In another preferred embodiment, in formula (I) compound, $R_0$ is H, F, Cl, Br, I, methyl, ethyl, propyl, isopropyl, monofluoroethyl, difluoromethyl, trifluoromethyl.

In another preferred embodiment, in formula (I) compound, $R_1$ and $R_2$ are each independently H, F, Cl, Br, I, methyl, ethyl, propyl, isopropyl, monofluoroethyl, difluoromethyl, trifluoromethyl, methoxy, ethoxy, propoxy, isopropoxy, cyclopropyloxy.

In another preferred embodiment, $R_4$ is selected from the group consisting of:

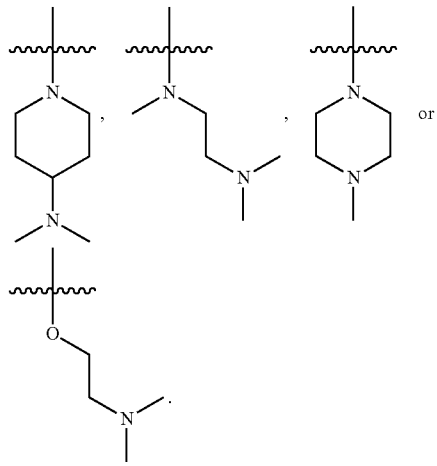

In another preferred embodiment, $R_3$ is methyl, ethyl, propyl, isopropyl, monofluoroethyl, difluoromethyl, trifluoromethyl, cyclopropyl, cyclobutyl, cyclopentyl, cyclohexyl, methoxy, ethoxy, propoxy, isopropoxy, cyclopropyloxy, substituted or unsubstituted $C_{3-10}$ heterocyclic radical, substituted or unsubstituted phenyl or substituted or unsubstituted $C_{4-8}$ cycloalkenyl.

In another preferred embodiment, said $C_{3-10}$ heterocyclic radical is pyrazolyl, morpholinyl, aza-$C_{3-7}$ cycloalkyl, pyrrolopyridyl, pyridopyrrolyl, pyrrolyl, indolyl, quinolyl, pyrimidyl or pyridyl.

In another preferred embodiment, said $C_{4-10}$ cycloalkenyl is cyclopentenyl, 1,3-cyclohexadienyl, 1,4-cyclohexadienyl, cyclohexenyl, or cycloheptenyl.

In another preferred embodiment, said substituted or unsubstituted $C_{3-10}$ heterocyclic radical is selected from the group consisting of:

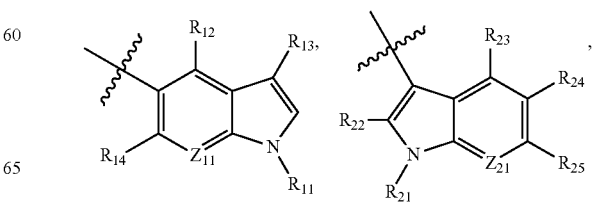

-continued

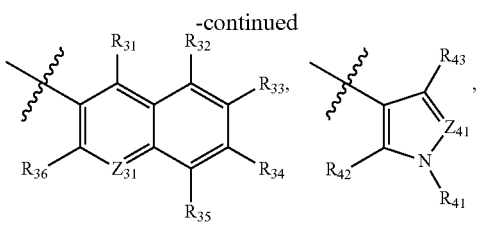

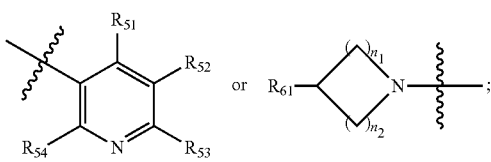

wherein, $Z_{11}$ is $CR_{15}$ or N; $Z_{21}$ is $CR_{26}$ or N; $Z_{31}$ is $CR_{37}$ or N, $Z_{41}$ is $CR_{44}$ or N; $n_1$ is 1, 2 or 3; $n_2$ is 1 or 2;

$R_{12}$, $R_{13}$, $R_{14}$, $R_{15}$, $R_{22}$, $R_{23}$, $R_{24}$, $R_{25}$, $R_{26}$, $R_{31}$, $R_{32}$, $R_{33}$, $R_{34}$, $R_{35}$, $R_{36}$, $R_{37}$, $R_{42}$, $R_{43}$, $R_{44}$, $R_{51}$, $R_{52}$, $R_{53}$, $R_{54}$, and $R_{61}$ are each independently H, hydroxy, CN, $NO_2$, halogen, $C_{1-10}$ haloalkyl, $C_{1-10}$ alkyl, —$CON(C_{1-10}$ alkyl$)_2$, —$N(C_{1-10}$ alkyl$)_2$, —$C(O)OC_{1-10}$ alkyl, —$OC(O)C_{1-10}$ alkyl, —$COC_{1-10}$ alkyl, —CO-phenyl, —$SO_2C_{1-10}$ alkyl, —$SO_2$-phenyl, —$S(O)C_{1-10}$ alkyl, —$S(O)$-phenyl; said alkyl or phenyl is unsubstituted or substituted with 1-3 substituents selected from the group consisting of F, Cl, and methyl;

$R_{11}$, $R_{21}$, and $R_{41}$ are each independently H, $C_{1-10}$ haloalkyl, $C_{1-10}$ alkyl, —$COC_{1-10}$ alkyl, —CO-phenyl, —$SO_2C_{1-10}$ alkyl, —$SO_2$-phenyl; wherein, said phenyl is unsubstituted or substituted with 1-3 substituents selected from the group consisting of F, Cl, and methyl.

In another preferred embodiment, $Z_{11}$ is N; $R_{12}$, $R_{13}$, and $R_{14}$ are each independently H, halogen, $C_{1-3}$ haloalkyl, $C_{1-3}$ alkyl; $R_{11}$ is H, $C_{1-3}$ haloalkyl, $C_{1-3}$ alkyl, —$COC_{1-3}$ alkyl, —$SO_2C_{1-3}$ alkyl.

In another preferred embodiment, $Z_{11}$ is N; $R_{12}$, $R_{13}$, and $R_{14}$ are each independently H, F, Cl, Br, methyl, ethyl, propyl, isopropyl, monofluoroethyl, difluoromethyl, trifluoromethyl; $R_{11}$ is H, methyl, ethyl, propyl, isopropyl, monofluoroethyl, difluoromethyl, trifluoromethyl, —$COCH_3$, —$SO_2CH_3$.

In another preferred embodiment, $Z_{21}$ is $CR_{26}$, $R_{22}$, $R_{23}$, $R_{24}$, $R_{25}$, and $R_{26}$ are each independently H, halogen, $C_{1-3}$ haloalkyl, $C_{1-3}$ alkyl; $R_{21}$ is H, $C_{1-3}$ haloalkyl, $C_{1-3}$ alkyl, —$COC_{1-3}$ alkyl, —$SO_2C_{1-3}$ alkyl.

In another preferred embodiment, $Z_{21}$ is $CR_{26}$; $R_{22}$, $R_{23}$, $R_{24}$, $R_{25}$, and $R_{26}$ are each independently H, F, Cl, Br, methyl, ethyl, propyl, isopropyl, monofluoroethyl, difluoromethyl, trifluoromethyl; $R_{21}$ is H, methyl, ethyl, propyl, isopropyl, monofluoroethyl, difluoromethyl, trifluoromethyl, —$COCH_3$, —$SO_2CH_3$.

In another preferred embodiment, $Z_{31}$ is N; $R_{31}$, $R_{32}$, $R_{33}$, $R_{34}$, $R_{35}$, and $R_{36}$ are each independently H, halogen, $C_{1-3}$ haloalkyl, $C_{1-3}$ alkyl.

In another preferred embodiment, $Z_{31}$ is N; $R_{31}$, $R_{32}$, $R_{33}$, $R_{34}$, $R_{35}$, and $R_{36}$ are each independently H, F, Cl, Br, methyl, ethyl, propyl, isopropyl, monofluoroethyl, difluoromethyl, trifluoromethyl.

In another preferred embodiment, $Z_{41}$ is N or $CR_{44}$; $R_{42}$, $R_{43}$, and $R_{44}$ are each independently H, halogen, $C_{1-3}$ haloalkyl, $C_{1-3}$ alkyl; $R_{41}$ is H, $C_{1-3}$ haloalkyl, $C_{1-3}$ alkyl, —$COC_{1-3}$ alkyl, —$SO_2C_{1-3}$ alkyl.

In another preferred embodiment, $Z_{41}$ is N or $CR_{44}$; $R_{42}$, $R_{43}$, and $R_{44}$ are each independently H, F, Cl, Br, methyl, ethyl, propyl, isopropyl, monofluoroethyl, difluoromethyl, trifluoromethyl; $R_{41}$ is H, methyl, ethyl, propyl, isopropyl, monofluoroethyl, difluoromethyl, trifluoromethyl, —$COCH_3$, —$SO_2CH_3$.

In another preferred embodiment, $R_{51}$, $R_{52}$, $R_{53}$, and $R_{54}$ are each independently H, halogen, $C_{1-3}$ haloalkyl, $C_{1-3}$ alkyl.

In another preferred embodiment, $R_{51}$, $R_{52}$, $R_{53}$, and $R_{54}$ are each independently H, F, Cl, Br, methyl, ethyl, propyl, isopropyl, monofluoroethyl, difluoromethyl, trifluoromethyl.

In another preferred embodiment, $n_1$ is 2; $n_2$ is 2; $R_{61}$ is H, halogen, $C_{1-3}$ haloalkyl, $C_{1-3}$ alkyl, —$COC_{1-3}$ alkyl, —$SO_2C_{1-3}$ alkyl.

In another preferred embodiment, $n_1$ is 2; $n_2$ is 2; $R_{61}$ is H, F, Cl, Br, methyl, ethyl, propyl, isopropyl, monofluoroethyl, difluoromethyl, trifluoromethyl, —$COCH_3$, —$SO_2CH_3$.

In another preferred embodiment, said formula (I) compound is a compound represented by formula (II), formula (III), formula (IV), formula (V), formula (VI), formula (VII), formula (VIII), or formula (IX):

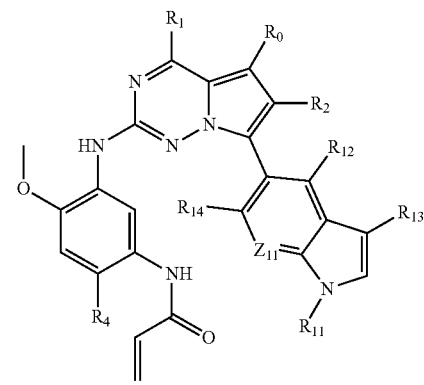

II wherein, $R_{11}$, $R_{12}$, $R_{13}$, $R_{14}$, $R_0$, $R_1$, $R_2$, $R_4$, and $Z_{11}$ are defined as above;

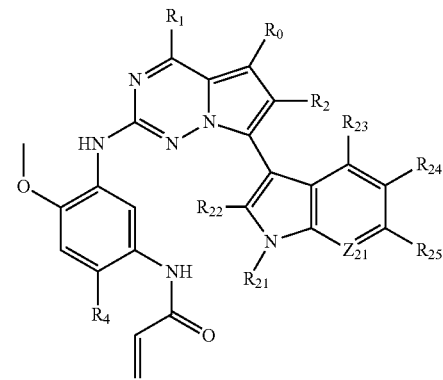

III wherein, $R_{21}$, $R_{22}$, $R_{23}$, $R_{24}$, $R_{25}$, $R_0$, $R_1$, $R_2$, $R_4$, and $Z_{21}$ are defined as above;

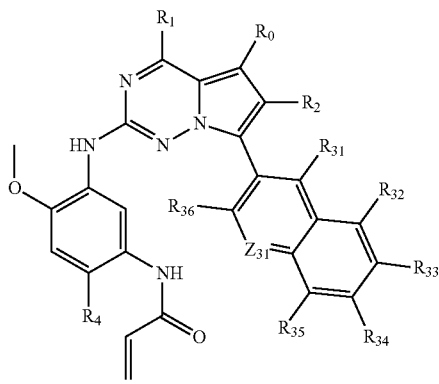

IV wherein, $R_{31}$, $R_{32}$, $R_{33}$, $R_{34}$, $R_{35}$, $R_{36}$, $R_0$, $R_1$, $R_2$, $R_4$, and $Z_{31}$ are defined as above;

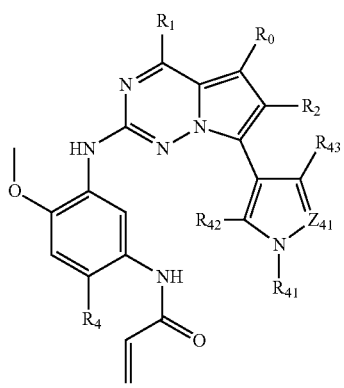

V wherein, $R_0$, $R_1$, $R_2$, $R_4$, $R_{41}$, $R_{42}$, $R_{43}$, and $Z_{41}$ are defined as above;

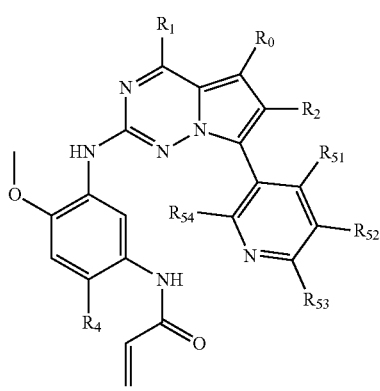

VI wherein, $R_{51}$, $R_{52}$, $R_{53}$, $R_{54}$, $R_0$, $R_1$, $R_2$, and $R_4$ are defined as above;

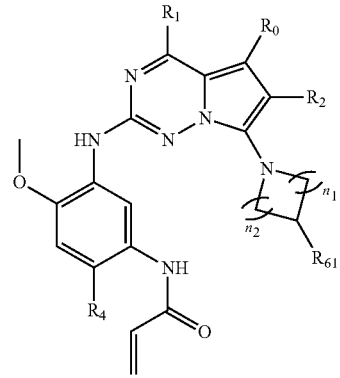

VII wherein, $R_0$, $R_1$, $R_2$, $R_4$, $R_{61}$, $n_1$, and $n_2$ are defined as above;

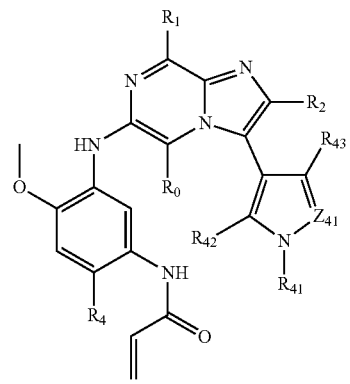

VIII wherein, $R_0$, $R_1$, $R_2$, $R_4$, $R_{41}$, $R_{42}$, $R_{43}$, and $Z_{41}$ are defined as above;

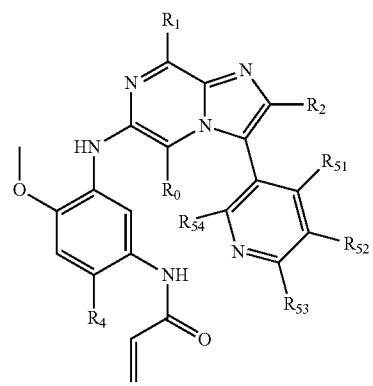

IX wherein, $R_{51}$, $R_{52}$, $R_{53}$, $R_{54}$, $R_0$, $R_1$, $R_2$, and $R_4$ are defined as above.

In another preferred embodiment, said formula (I) compound is selected from the group consisting of the following compounds and compounds J-24 to J-54 in Table 5:

11
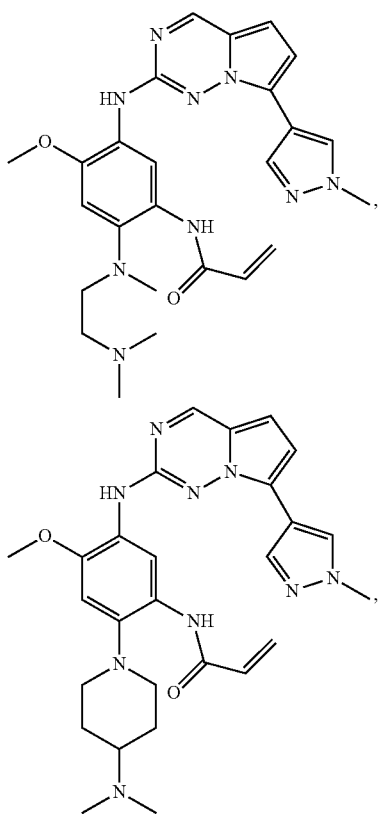
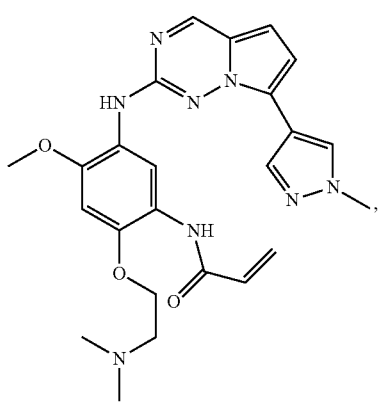
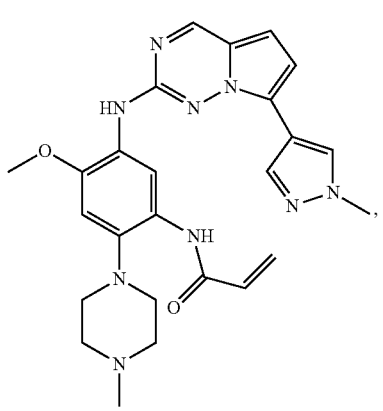
12
-continued
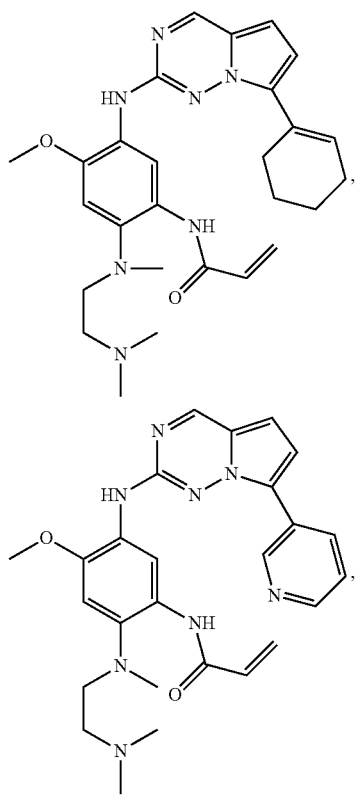
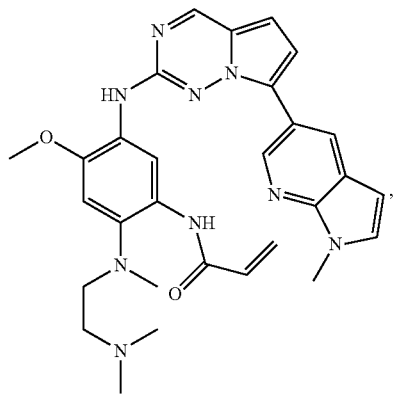
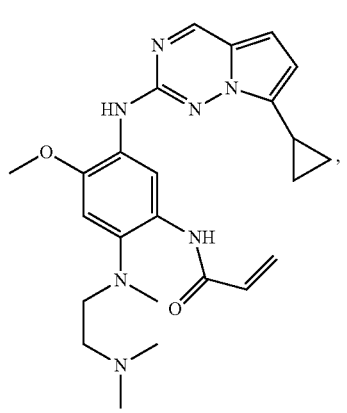

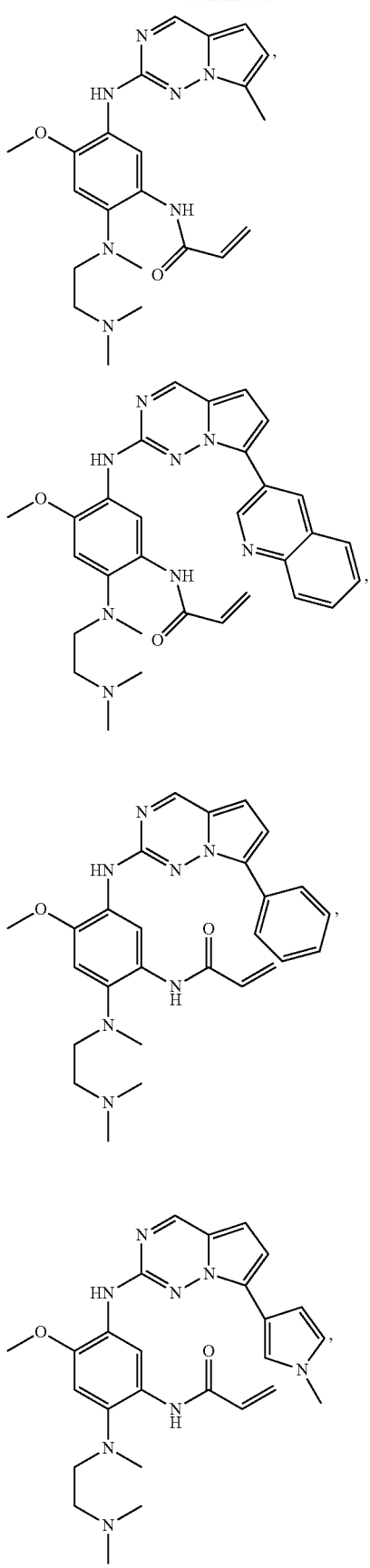
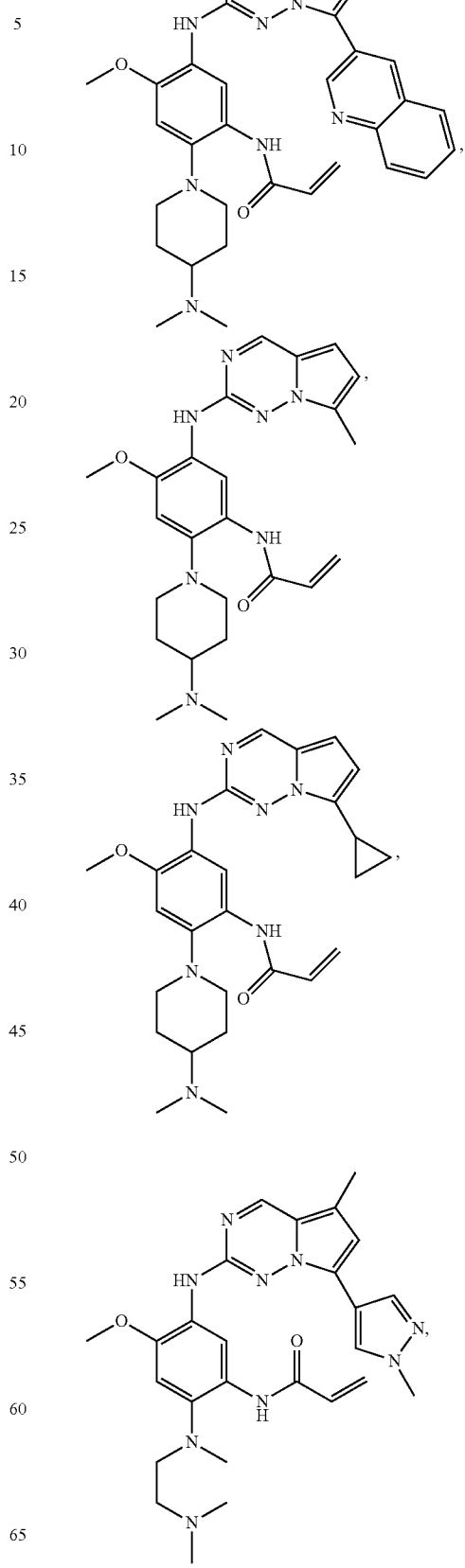

15
-continued
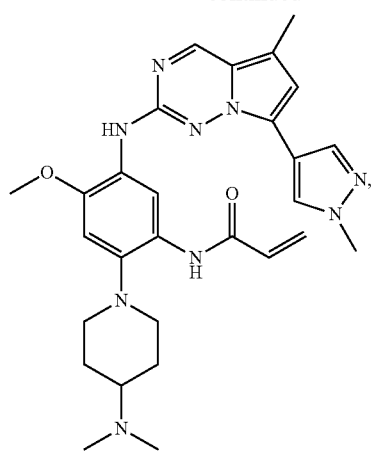
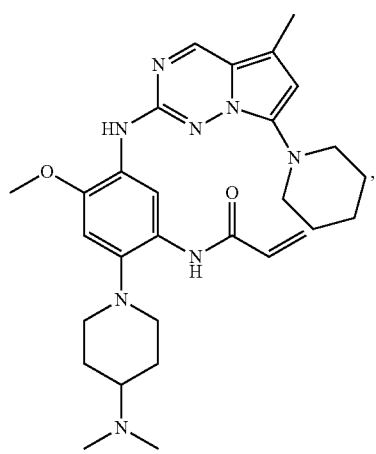
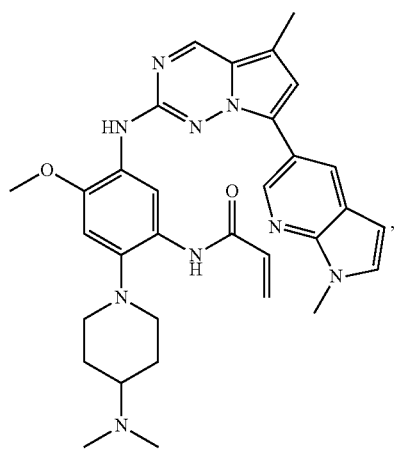
16
-continued
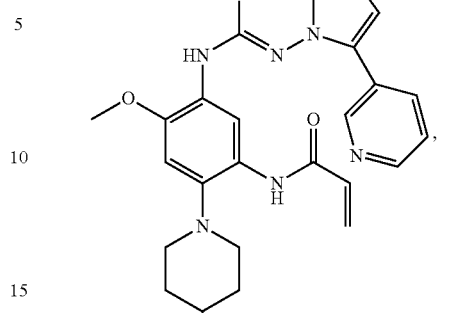
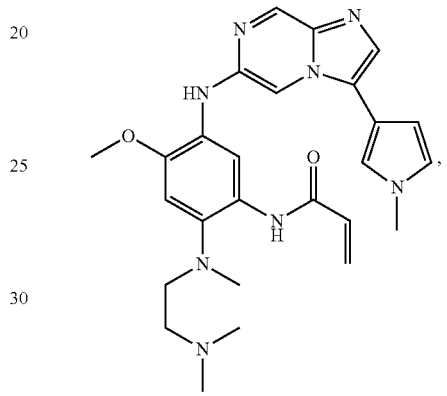
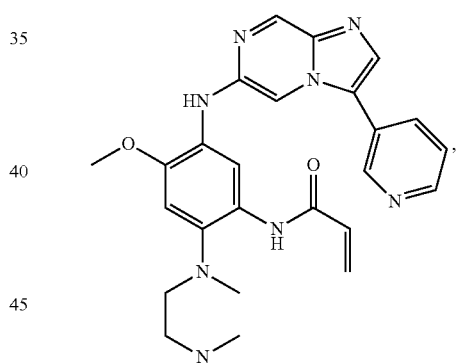
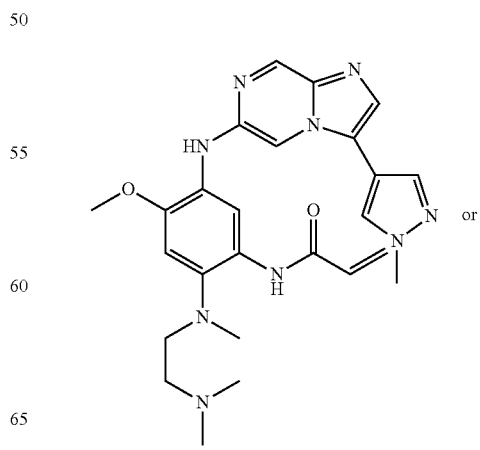 or -continued

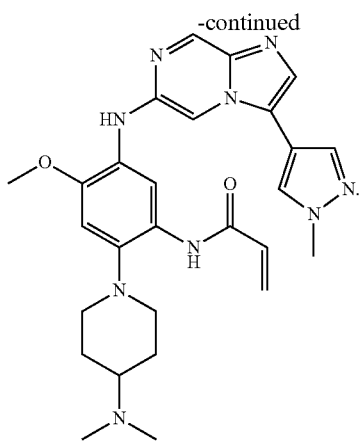

In the second aspect of the present invention, a pharmaceutical composition is provided, wherein said composition comprises the compound, or pharmaceutically acceptable salt, solvate, stereoisomer, or prodrug thereof of the first aspect of the present invention, and a pharmaceutically acceptable carrier.

In the third aspect of the present invention, there is provided use of the compound, or pharmaceutically acceptable salt, solvate, stereoisomer, or prodrug thereof of the first aspect of the present invention in (i) the manufacture of a medicament for the regulation of EGFR tyrosine kinase activity or (ii) the manufacture of a medicament for preventing and/or treating a EGFR-related disease.

In another preferred embodiment, said regulation is up-regulation or down-regulation.

In another preferred embodiment, said EGFR-related disease is selected from the group consisting of cancer, diabetes, immune system disease, neurodegenerative disease, cardiovascular disease, or a disease with acquired drug-resistance during treatment with an EGFR modulator.

In another preferred embodiment, said cancer is non-small cell lung cancer, head and neck cancer, breast cancer, kidney cancer, pancreatic cancer, cervical cancer, esophageal cancer, pancreatic cancer, prostate cancer, bladder cancer, colorectal cancer, ovarian cancer, gastric cancer, brain malignancies including glioblastomas, etc., or any combination thereof.

In another preferred embodiment, said non-small cell lung cancer is caused by an EGFR mutation, including a sensitive mutation (such as L858R mutation or exon 19 deletion) and a drug-resistance mutation (such as EGFR T790M mutation).

In the present invention, EGFR modulators refer to small molecule tyrosine kinase inhibitors targeting EGFR, such as gefitinib, erlotinib, icotinib, lapatinib, afatinib and the like.

In another preferred embodiment, said disease with acquired drug-resistance is a disease caused by the T790 mutation encoded by EGFR exon 20 or comprises a disease caused by the T790 mutation encoded by EGFR exon 20.

In another preferred embodiment, said T790 encoded by EGFR exon 20 is T790M.

In the fourth aspect of the present invention, a medicinal composition is provided, wherein said medicinal composition comprises the compound, or pharmaceutically acceptable salt, solvate, stereoisomer, or prodrug thereof of the first aspect of the present invention, and an additional medicament which is one or more medicaments selected from the group consisting of: gefitinib, erlotinib, icotinib, lapatinib, XL647, NVP-AEE-788, kRRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitors, CNF2024, tanespimycin, alvespimycin, IPI-504, SNX-5422, NVP-AUY922.

Except the compounds of the present invention or pharmaceutically acceptable salt, solvate, stereoisomer, or prodrug thereof, the additional medicaments in the aforementioned medicinal composition are all antitumor drugs well known to those skilled in the art It is to be understood that within the scope of the present invention, each foregoing technical feature of the present invention and each technical feature described in detail below (e.g., examples) may be combined with each other to form a new or preferred technical solution which needs not be described one by one due to space limitations.

DETAILED DESCRIPTION OF THE INVENTION

Based on a long-term and in-depth study, the inventors have unexpectedly found a class of selective inhibitors of the EGFR mutation which can inhibit EGFR-resistant mutant enzymes (e.g. T790M/L858R double mutant enzymes) and the proliferation of cell lines thereof (e.g. H1975) at a low concentration (e.g., nanomolar concentration), while have a relatively weak inhibition against wild-type EGFR enzyme and the cell lines thereof (e.g., A431). Therefore, this kind of structure is suitable for the cases wherein the secondary resistance is generated in the current EGFR-TKI treatment, and at the same time the mutation selectivity thereof greatly reduces the side effects produced by the inhibition of wild-type EGFR. Meanwhile, such compounds have lower cytotoxicity in normal cell lines (e.g., NIH-3T3 cells), thus greatly reducing the non-specific toxic side effects, which makes them ideal replacements for the second-generation EGFR-TKI. On such basis, the present invention has been completed.

Definition of the Terms

As used herein, "$C_{3-10}$ heterocyclic radical" refers to a heterocyclic radical having 3-10 carbon atoms, wherein the atoms constituting the ring contain at least one heteroatom selected from N, S, and O in addition to the carbon atoms. The examples include a 5-6 membered monocyclic heteroaromatic ring containing 1 to 2 nitrogen atoms, a 9-10 membered bicyclic heteroaromatic ring containing 1, 2 or 3 nitrogen atoms, and 4-7 membered saturated mono-heterocyclic radical containing 1 to 2 heteroatoms selected from N, S, and O. Specific examples include pyrazolyl, morpholinyl, aza-$C_{3-7}$ cycloalkyl, pyrrolopyridyl, pyridopyrrolyl, pyrrolyl, pyrazolopyridyl, indazolyl, indolyl, quinolyl, pyridyl, imidazolyl, pyridazinyl, pyrimidinyl, pyrazinyl, isoindolyl, isoquinolyl, benzimidazolyl, quinazolinyl, quinoxalinyl, cinnolinyl, phthalazinyl, piperidinyl, tetrahydropyrrolyl, azetidinyl, azepanyl and the like.

As used herein, "$C_{1-10}$ alkyl" refers to a straight or branched saturated aliphatic hydrocarbyl having 1 to 10 carbon atoms, such as methyl, ethyl, propyl, isopropyl and the like.

As used herein, "$C_{1-10}$ haloalkyl" means that $C_{1-10}$ alkyl is substituted with 1, 2 or 3 halogen atoms (preferably fluorine atoms), such as monochloroethyl, dichloromethyl, 1,2-dichloroethyl, monobromoethyl, monofluoroethyl, difluoromethyl, trifluoromethyl and the like.

As used herein, "$C_{3-10}$ cycloalkyl" refers to a cycloalkyl having 3 to 10 carbon atoms. Examples of cycloalkyl are cyclopropyl, cyclobutyl, cyclopentyl, cyclohexyl and the like.

As used herein, "$C_{3-8}$ cycloalkoxy" refers to $C_{3-8}$ cycloalkyl-O—, such as cyclopropyloxy, cyclobutoxy, cyclopentyloxy, cyclohexyloxy and the like.

As used herein, "$C_{1-10}$ alkoxy" refers to $C_{1-10}$ alkyl-O—, such as methoxy, ethoxy, propoxy, butoxy and the like.

As used herein, "$C_{2-10}$ alkenyl" refers to a straight or branched chain unsaturated aliphatic hydrocarbyl with a carbon-carbon double bond (C=C) having 2-10 (preferably 2-6) carbon atoms, such as vinyl, propenyl, isopropenyl, n-butenyl, isobutenyl, pentenyl, hexenyl and the like.

As used herein, "aza-$C_{3-7}$ cycloalkyl" refers to a cycloalkyl group having 3-7 carbon atoms and the atoms constituting the ring contain at least one N atom in addition to carbon, such as piperidine ring, tetrahydropyrrole ring, azetidine, azepane and the like.

As used herein, "$C_{6-10}$ aryl" and "$C_{6-10}$ aromatic ring" can be used interchangeably and refer to aromatic hydrocarbyl having 6 to 10 carbon atoms such as phenyl, naphthyl and the like.

As used herein, "halogen" refers to F, Cl, Br or I.

As used herein, "$C_{4-10}$ cycloalkenyl" refers to a partially unsaturated monocarbocycle containing 4-10 carbon atoms as ring atoms, preferably $C_{4-8}$ cycloalkenyl, including but not limited to, cyclopentenyl, 1,3-cyclohexadienyl, 1,4-cyclohexadienyl, cyclohexenyl, cycloheptenyl and the like.

As used herein, "heteroaromatic ring" and "heteroaryl" can be used interchangeably and refer to a group having 5-10 ring atoms, preferably 5, 6, 9 or 10 ring atoms and having 1-5 heteroatoms beside carbon atoms, wherein the ring array shares 6, 10 or 14π electrons. The term "heteroatom" refers to nitrogen, oxygen or sulfur.

As used herein, "partially unsaturated" refers to a 7π-electron system containing one or more unsaturated bonds but not fully conjugated.

As used herein, "5-6 membered monocyclic heteroaromatic ring containing 1-2 nitrogen atoms" refers to a monocyclic heteroaryl having 5-6 ring atoms and 1-2 nitrogen atoms, such as including but not limited to imidazolyl, pyrrolyl, pyrazolyl, pyridyl, pyridazinyl, pyrimidinyl, pyrazinyl and the like.

As used herein, "9-10 membered bicyclic heteroaromatic ring containing 1, 2 or 3 nitrogen atoms" refers to a bicyclic heteroaryl having 9-10 ring atoms and 1, 2 or 3 nitrogen atoms, such as including but not limited to indolyl, isoindolyl, quinolyl, isoquinolyl, indazolyl, benzimidazolyl, quinazolinyl, quinoxalinyl, cinnolinyl, phthalazinyl.

As used herein, the 5-6 membered monocyclic heteroaromatic ring or 9-10 membered bicyclic heteroaromatic ring in the present invention are preferably selected from the group consisting of:

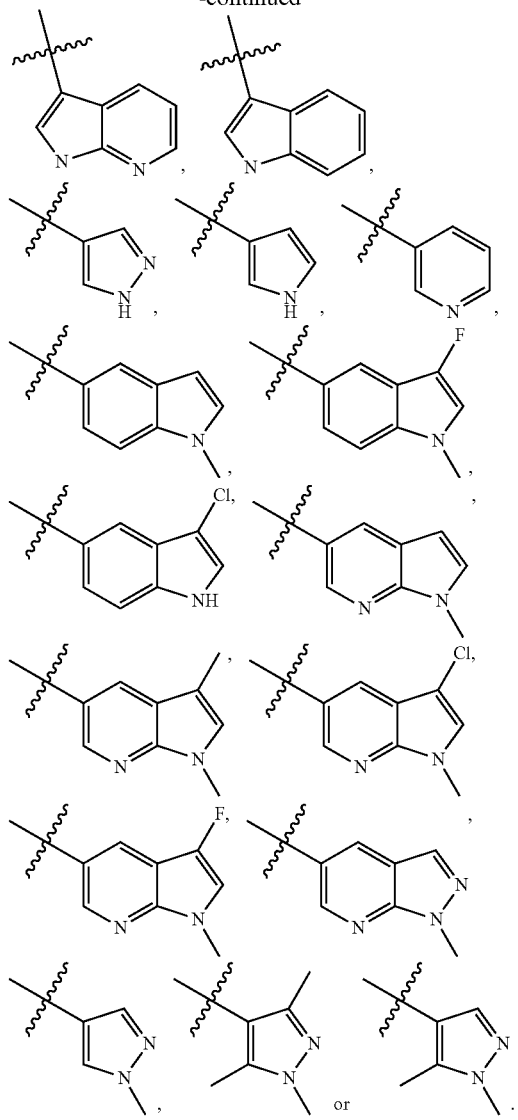

As used herein, "4-7 membered saturated mono-heterocyclic radical containing 1 or 2 heteroatoms selected from N, O or S" refers to a saturated monocyclic group containing 4-7 ring atoms, wherein 1 or 2 carbon atoms are replaced by nitrogen, oxygen or sulfur atom. Examples of mono-heterocyclic radical include, but are not limited to, morpholinyl, piperidinyl, tetrahydropyrrolyl, azetidine, azepane.

As used herein, "6 membered partially unsaturated monocyclic group" refers to a partially unsaturated monocyclic group containing 6 carbon atoms as ring atoms including, but not limited to 1,3-cyclohexadienyl, 1,4-cyclohexadienyl, cyclohexenyl and the like.

Pharmaceutical Compositions

The phrase "the active substance of the present invention" or "the active compound of the present invention" refers to the compound of formula (I) of the present invention, or a pharmaceutically acceptable salt, solvate, stereoisomer, or prodrug thereof, which has significant EGFR inhibitory activity. It not only has a high inhibitory activity against EGFR T790M resistance mutations, but also has a significantly reduced inhibitory activity against wild-type EGFR, which means it has a high selectivity inhibitory activity and also low cytotoxicity. In addition, the compounds of the present invention exhibit advantageous physical properties, toxicity characteristics and/or metabolic characteristics as compared to other known EGFR mutant inhibitors.

As used herein, said "pharmaceutically acceptable salt" includes a pharmaceutically acceptable acid addition salt and a pharmaceutically acceptable base addition salt.

"Pharmaceutically acceptable acid addition salt" refers to a salt formed with an inorganic acid or an organic acid that is capable of retaining the bioavailability of the free base without other side effects. Inorganic acid salt includes, but is not limited to, hydrochloride, hydrobromide, sulfate, phosphate and the like; and organic acid salt includes, but is not limited to formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

"Pharmaceutically acceptable base addition salt" includes, but is not limited to, salt of an inorganic base such as sodium, potassium, calcium and magnesium salts and the like, and includes, but is not limited to, salt of an organic base such as ammonium salt, triethylamine salt, lysine salt, arginine salt and the like. These salts can be prepared by the methods known in the art.

As used herein, the compounds of formula (I) may be present in one or more crystalline forms, and the active compounds of the present invention include various crystalline forms and mixtures thereof.

"Solvate" as used in the present invention refers to a complex formed by the compound of the present invention with a solvent. They either react in a solvent or precipitate or crystallize out of the solvent. For example, a complex formed with water is called a "hydrate". Solvates of the compounds of formula (I) are within the scope of this invention.

The compounds represented by formula (I) of the present invention may contain one or more chiral centers and exist in different optically active forms. When the compound contains one chiral center, the compound comprises an enantiomer. The present invention includes both isomers and mixtures thereof, such as racemic mixtures. Enantiomers can be resolved by methods known in the art, such as crystallization, chiral chromatography and the like. When the compound of formula (I) contains more than one chiral center, diastereomers may be present. The present invention includes specific optically pure isomers which have been resolved, as well as mixtures of diastereomers. Diastereomers can be resolved by methods known in the art, such as crystallization and preparative chromatography.

The present invention includes prodrugs of the above-mentioned compounds. Prodrugs include amino-protecting group and carboxy-protecting group known in the art, which are released to yield the parent compound via hydrolyzation or enzymatic reactions under physiological conditions. For specific preparation methods of prodrug, one can refer to Saulnier, M. G.; Frennesson, D. B.; Deshpande, M. S.; Hansel, S. B and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, Med. Chem. 2000, 43, 475.

In general, the compounds of the present invention or pharmaceutically acceptable salts, solvates, stereoisomers or prodrugs thereof may be administered in a suitable dosage form with one or more pharmaceutically acceptable carriers. These dosage forms are suitable for oral, rectal administration, topical administration, intraoral administration, and other parenteral administration (e.g., subcutaneous, intramuscular, intravenous, etc.). For example, dosage forms suitable for oral administration include capsules, tablets, granules, and syrups. The compounds of the present invention contained in these formulations may be solid powders or granules; solutions or suspensions in aqueous or non-aqueous liquids; water-in-oil or oil-in-water emulsions and the like. The above dosage forms may be made from the active compound and one or more carriers or excipients via a general pharmaceutical method. The above carrier needs to be compatible with the active compound or other excipients. For solid preparations, commonly used non-toxic carriers include, but are not limited to, mannitol, lactose, starch, magnesium stearate, cellulose, glucose, sucrose and the like. Carriers for liquid preparations include water, physiological saline, aqueous dextrose solution, ethylene glycol, polyethylene glycol and the like. The active compound may form a solution or a suspension with the above carrier.

The compositions of the present invention are formulated, quantified and administered in a manner consistent with medical practice. The "therapeutically effective amount" of the compound administrated is determined by factors such as the particular condition to be treated, the subject being treated, the cause of the disorder, the target of the drug, and the mode of administration.

The "therapeutically effective amount" refers to an amount that can be functional or active to humans and/or animals and which can be accepted by humans and/or animals.

The therapeutically effective amount of the compound of the present invention or a pharmaceutically acceptable salt, solvate, stereoisomer, or prodrug thereof contained in the pharmaceutical composition or medicinal composition of the present invention contains is preferably from 0.1 mg to 5 g/kg (body weight).

The compounds of formula (I) of the present invention, or pharmaceutically acceptable salts, solvates, stereoisomers or prodrugs thereof may be used in combination with other drugs in certain diseases to achieve the desired therapeutic effect. An example of a combined application is for the treatment of advanced NSCLC. For example, a therapeutically effective amount of a compound of formula (I) of the present invention is used in combination with a mTOR inhibitor (e.g., rapamycin); or in combination with a Met inhibitor (including Met antibody MetMAb and Met small molecule inhibitor PF02341066); or in combination with an IGF1R inhibitor (e.g., OSI-906); or in combination with a heat shock protein inhibitor and so on.

Preparation Methods

The preparation method of compounds represented by formula (I) of the present invention will be described in more detail below, but these specific methods do not constitute any restriction on the present invention. The compounds of the present invention may also be conveniently prepared by optionally combining the various synthetic methods described in the present specification or those known in the art, and such combinations may be readily carried out by one of skill in the art to which this invention pertains.

For example, the preparation process of the compounds of formulas (I-a) and (I-b) of the present invention may include, but is not limited to, the following procedure.

Scheme 1

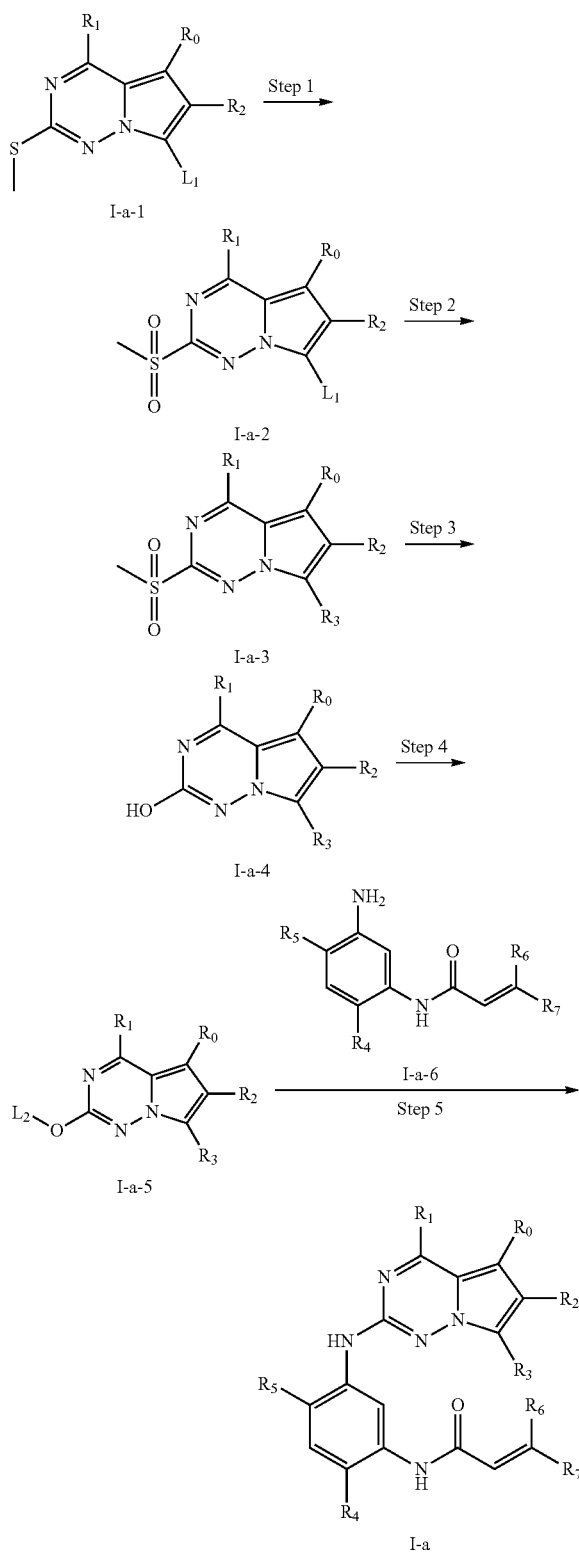

In Scheme 1, $L_1$ and $-O-L_2$ are a leaving group including, but not limited to, trifluoromethanesulfonates; chlorine, bromine, iodine; sulfonate groups such as methanesulfonate, tosylate, p-bromobenzenesulfonate, p-toluenesulfonate and the like; acyloxy groups such as acetoxy, trifluoroacetoxy and the like. Other substituents and groups are as defined in the specification.

The compound of the formula (I-a-1) may be sequentially subjected to an oxidation reaction, a coupling reaction, a reduction reaction, a substitution reaction, and a coupling reaction to form a compound of the formula (I-a).

In step 2, the compound of the formula (I-a-2) may be subjected to a coupling reaction (e.g., Suzuki coupling or the like) with a boronic acid or boron ester compound having an $R_3$ group to form a compound of the formula (I-a-3); this synthesis can be conveniently carried out by selecting the appropriate conditions and methods according to different substrates. For example, the process can be carried out at a certain temperature using a suitable catalyst (or containing an appropriate ligand) or a base and a suitable solvent. The method is a conventional method used by those skilled in the art.

In step 4, the compound of formula (I-a-4) may be reacted with a suitable reagent to form a leaving group, such as a sulfonate group, an acetoxy group or the like.

In step 5, the compound of formula (I-a-5) may be reacted with a compound of formula (I-a-6) through a substitution reaction or coupling reaction to form a compound of formula (I-a), for example at a certain temperature using a suitable catalyst (or with suitable ligand) or a base and a suitable solvent. For example, if acid catalysis is used, the catalyst can be, but is not limited to, TFA or p-toluenesulfonic acid. In case Buchwald-Hartwig amination is used, the palladium catalyst used can be, but is not limited to, $Pd_2(dba)_3$, and the ligand used can be, but is not limited to, XantPhos (4,5-bis(diphenylphosphino)-9,9-dimethylxanthene), the base used can be, but is not limited to, cesium carbonate.

The above-mentioned various reactions in Scheme 1 are reactions well known by those skilled in the art.

The compounds of formula (I-a-1) and formula (I-a-6) can be prepared by methods well known in the art. The compound of formula (I-a-1) can be prepared by the following exemplary methods:

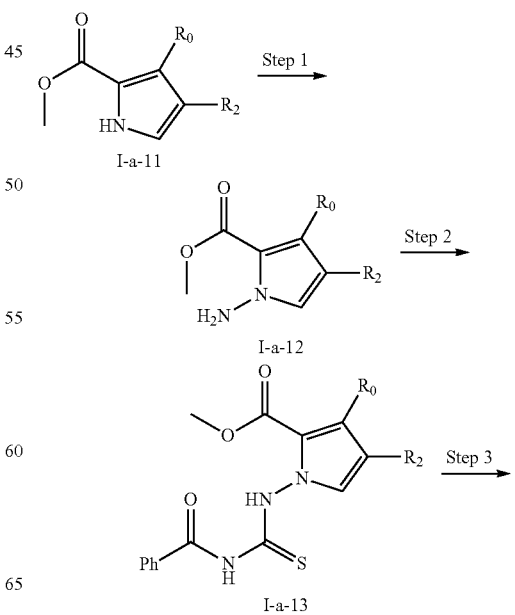

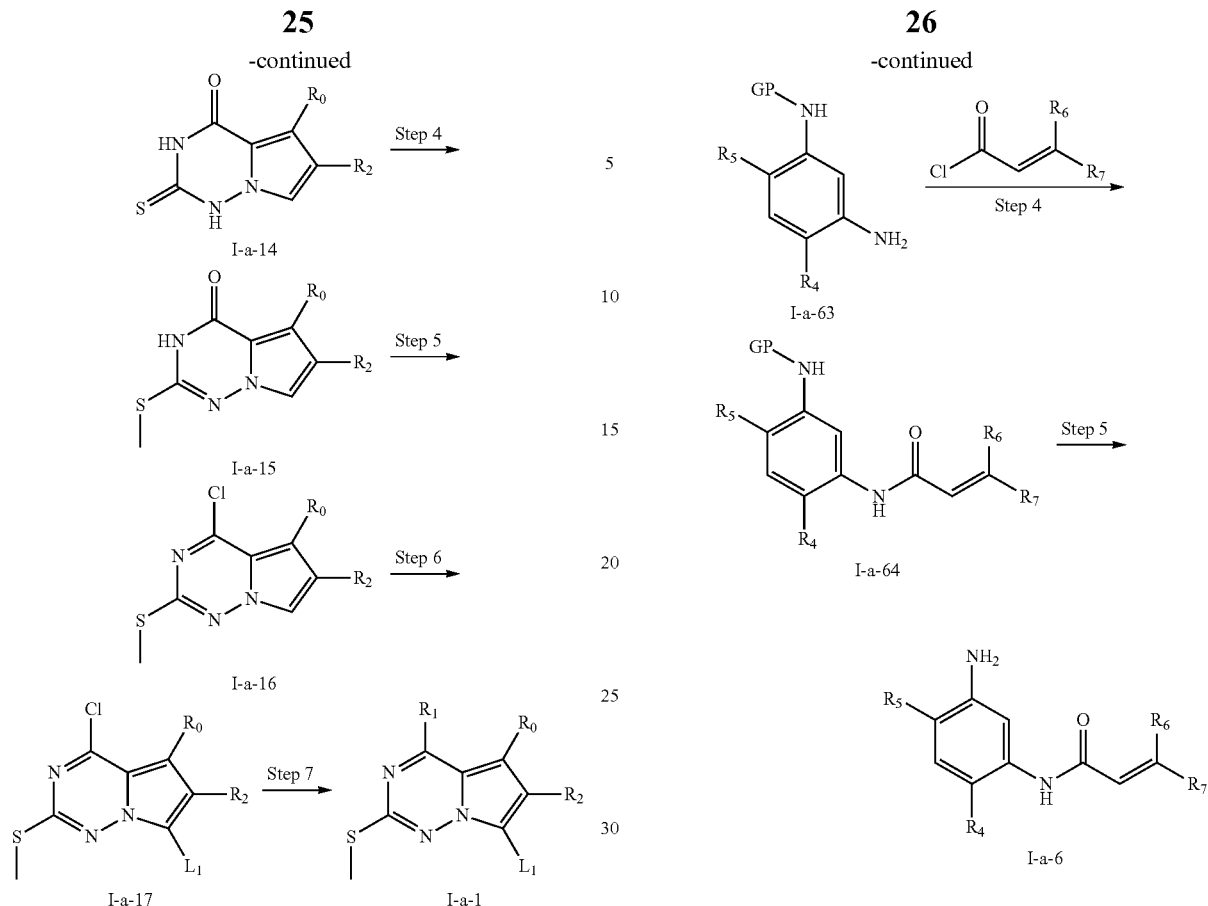

In each of the above formulas, the substituents and groups are as defined in the specification. The formula (I-a-11) compound (commercially available) as a starting material is sequentially subjected to an amine substitution reaction, a benzoyl isothiocyanate esterification reaction, a cyclization reaction, a methylation reaction, a chlorination reaction and a substitution reaction to generate the formula (I-a-1) compound. One can refer to known methods for each of the above-mentioned reaction reagents and reactions.

The compound of formula (I-a-6) can be prepared by the following exemplary methods:

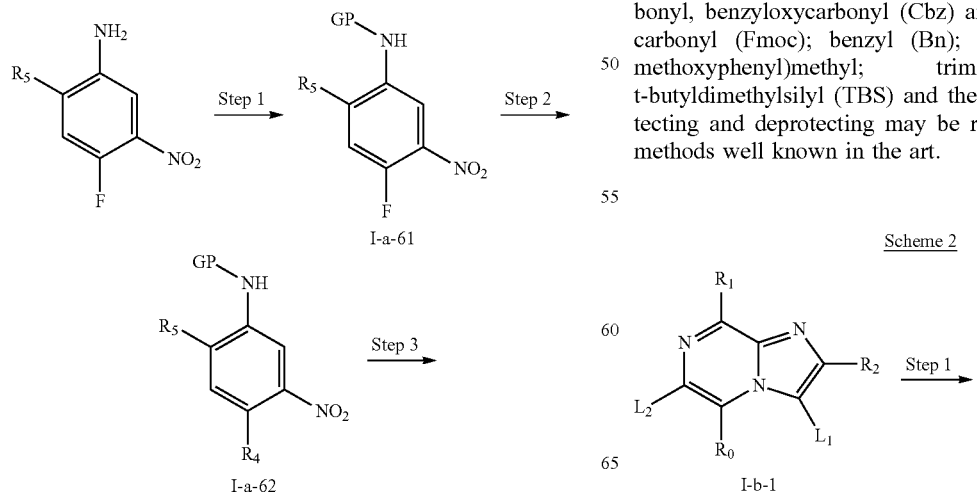

The compound 4-fluoro-2-$R_5$-5-nitroaniline as a starting material is sequentially subjected to an amino protection reaction, an amine substitution reaction, a nitro reduction reaction, an acylation reaction and an amino deprotection reaction to prepare the formula (I-a-6) compound. The above-mentioned reactions are conventional reactions in the art. The compound 4-fluoro-2-$R_5$-5-nitroaniline is commercially available or can be prepared by methods known to those skilled in the art (Methods for synthesizing formula (I-a-6) compound can be referred to WO2013014448A1).

PG in the compound of formula (I-a-61) is an amino-protecting group. Amino-protecting groups include, but are not limited to, tert-butoxycarbonyl (floc); arylmethoxycarbonyl, benzyloxycarbonyl (Cbz) and 9-fluorenylmethoxycarbonyl (Fmoc); benzyl (Bn); trityl (Tr); 1,1-bis-(4'-methoxyphenyl)methyl; trimethylsilyl (TMS), t-butyldimethylsilyl (TBS) and the like. Methods for protecting and deprotecting may be referred to conventional methods well known in the art.

Scheme 2

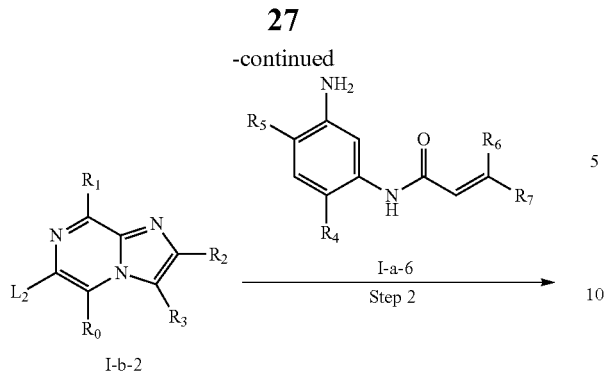

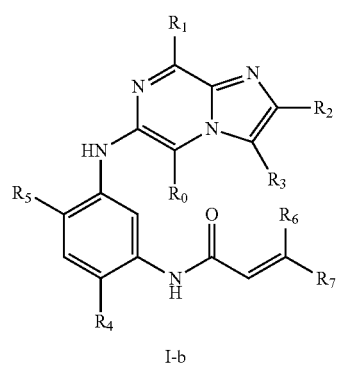

In Scheme 2, the substituents and groups are as defined in the specification.

The compound of the formula (I-b-1) may be sequentially subjected to a substitution reaction or a coupling reaction with various boronic acid or boron ester compound having a $R_3$ group and with formula (I-a-6) compound to form formula (I-b) compound. The reagents and conditions used in the reactions are known in the art.

The compound of formula (I-b-1) may be prepared by methods well known in the art, for example prepared by the following exemplary method:

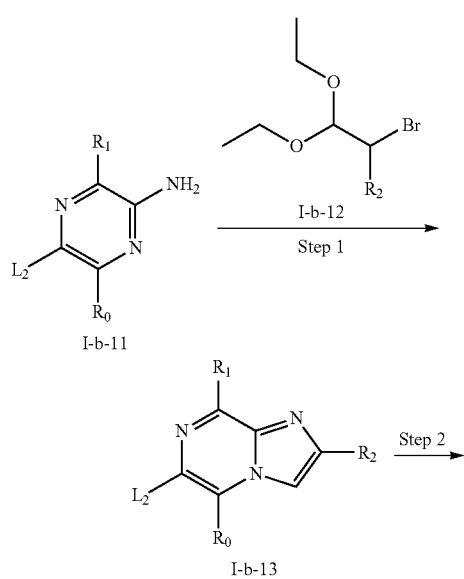

wherein, the substituents and groups are as defined in the specification. The formula (I-b-11) compound and formula (I-b-12) compound are subjected to a cyclization reaction and then reacted with a suitable reagent to form a leaving group such as bromine, iodine, sulfonate, acetoxy and the like, thereby generating formula (I-b-1) compound. The synthesis method is a known method.

The formula (I-a) compound or formula (I-b) compound, the preparation methods thereof, the pharmaceutical composition, and the therapeutic regimens disclosed in the present invention can be achieved by the skilled in the art with reference to the contents of the present invention and with appropriate modification of the process parameters. It is to be noted that all similar alternatives and modifications will be apparent to those skilled in the art and are considered to be included in the present invention. The products, methods and applications of the present invention have been described by way of preferred embodiments and examples, and it will be apparent to those skilled in the art that changes or appropriate modification and combinations of the methods and applications described herein can be made to realize and apply the technology of the present invention while not departing from the contents, spirit and scope of the present invention.

Compared with the prior art, the main advantages of the present invention are:

(1) The compounds of the present invention have a high inhibitory activity against EGFR T790M mutant (particularly EGFR T790M/L858R double mutant) enzymes or cells thereof and have a low inhibitory activity against wild type EGFR (EGFR WT) enzyme or cells thereof. Therefore, the compounds of the present invention have high selectivity.

(2) The compounds of the present invention exhibit high selectivity to EGFR double mutant enzymes and cells, while have low nonspecific cytotoxicity.

(3) The compounds of the present invention also exhibit favorable physical properties (e.g., higher water solubility), favorable toxicity characteristics (e.g., lower hERG blocking tendency) and favorable metabolic characteristics (e.g., better pharmacokinetic properties, such as bioavailability) compared to other known EGFR mutation inhibitors.

The present invention will be further elucidated with reference to specific examples. It is to be understood that these examples are merely illustrative of the present invention and are not intended to limit the scope of the present invention. The experimental methods which do not specify specific conditions in the following examples are generally carried out according to conventional conditions such as those described in Sambrook et al., Molecular Cloning: Laboratory Manual (New York: Cold Spring Harbor Laboratory Press, 1989), or conditions as recommended by the manufacturers. Unless otherwise indicated, percentages and parts are by weight.

Unless otherwise defined, terms used herein are of the same meanings that are familiar to those skilled in the art. In addition, any methods and materials similar with or equivalent to those described herein can be applied to the present invention.

Reagents and Instruments

¹HNMR: Bruker AVANCE-400 NMR instrument, internal standard is tetramethylsilane (TMS).

LC-MS: Agilent 1200 HPLC System/6140 MS spectrometer (manufacturer: Agilent), WatersX-B ridge column, 150× 4.6 mm, 3.5 μm.

Preparative high performance liquid chromatography (pre-HPLC): Waters PHW007, XBridge C18 column, 4.6*150 mm, 3.5 μm.

ISCO Combiflash-Rf75 or Rf200 automatic column instrument as well as Agela 4 g, 12 g, 20 g, 40 g, 80 g, and 120 g disposable silica gel column were used.

Known starting materials may be synthesized using methods known in the art, or can be purchased from ABCR GmbH & Co. KG, Acros Organics, Aldrich Chemical Company, Accela ChemBio Inc, Darryl Chemicals and so on.

Unless otherwise specified, the reactions in the examples were carried out in nitrogen or argon atmosphere.

Unless otherwise stated, the solutions in the examples were aqueous solutions.

DMF: dimethylformamide, DMSO: dimethylsulfoxide, THF: tetrahydrofilran, DIEA: N,N-diisopropylethylamine, EA: ethyl acetate, PE: petroleum ether, BINAP: (2R,3S)-2, 2'-bis-diphenylpho sphino-1,1'-binaphthalene. NBS (N-bromosuccinimide), NCS (N-chlorosuccinimide), Pd$_2$(dba)$_3$ (tris (dibenzylideneacetone) dipalladium), Pd (dppf)Cl$_2$ ([1, 1'-bis (diphenylphosphino) ferrocene] dichloropalladium).

As used herein, room temperature refers to about 20-30° C.

The Preparation of Compound 1-a

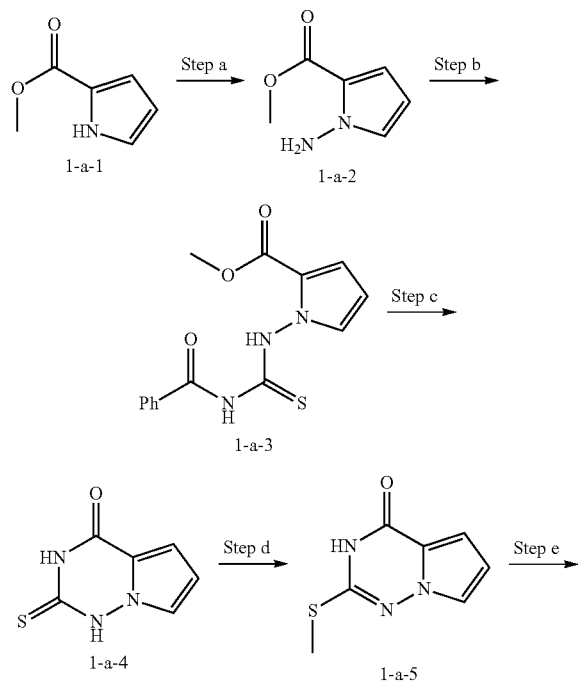

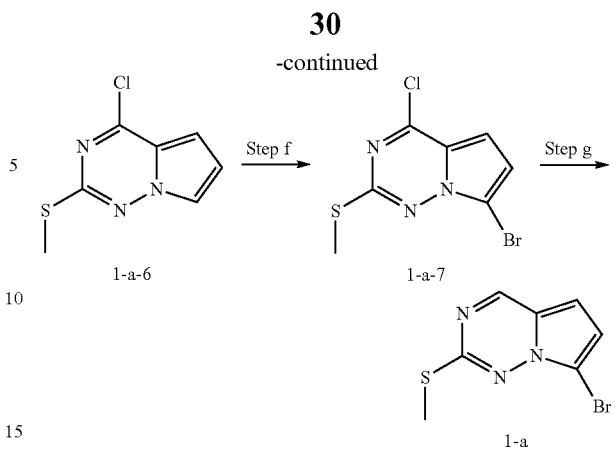

Step a: 25.0 g of the starting material 1-a-1 (0.19 mol) was dissolved in 1 L of tetrahydrofuran in a 4 L flask and stirred at room temperature for 20 minutes under nitrogen. A solution of 1 M potassium t-butoxide in tetrahydrofuran (500.0 mL, 0.50 mol) was added to the solution and stirred for 1 hour. Then, 0.15 M of chloramine ether solution (2.1 L, 0.31 mol) was added to the reaction solution at 10° C. over 20 minutes while nitrogen gas was introduced. After 2 hours, a saturated aqueous solution of sodium thiosulfate (500 ml) was added dropwise to the reaction mixture and stirred for another one hour. The organic phases were separated, washed with water and saturated brine, respectively, and dried over anhydrous sodium sulfate. After removal of the desiccant, the filtrate was concentrated under reduced pressure to give compound 1-a-2 as an oil. MS m/z (ESI): 141.2 [M+H]$^+$.

Step b: The crude compound 1-a-2 was dissolved in 500 ml of tetrahydrofuran, and then a solution of benzoyl isothiocyanate in tetrahydrofuran was added dropwise at room temperature, followed by reaction overnight. After completion of the reaction, the reaction solution was concentrated under reduced pressure. 200 ml of diethyl ether was added to the crude product and stirred for 30 minutes, filtered and washed with n-hexane/diethyl ether (9:1) to give off-white solid compound 1-a-3 (38.2 g, 65%). MS m/z (ESI): 304.0 [M+H]$^+$.

Step c: Compound 1-a-3 (38.20 g, 126 mmol) and sodium hydroxide solution (2M, 252 ml, 504 mmol) were added to a 500 ml flask, heated to 85° C. and reacted for 90 minutes, then cooled to room temperature. 100 ml of ethanol was added and acetic acid (29 ml, 510 mmol) was added dropwise under ice bath and stirred for another 30 minutes. The solid was filtered and washed with iced ethanol and concentrated to give a white solid. 200 ml of diethyl ether was added and stirred for 30 minutes. The mixture was filtered and washed with diethyl ether to give compound 1-a-4 (17.5 g, 83%) as a white solid. MS m/z (ESI): 168.1 [M+H]$^+$.

Step d: Compound 1-a-4 (17.5 g, 105 mmol) and 500 ml of tetrahydrofuran were added to a 1 L flask, followed by the addition of 8.4 ml of methyl iodide (135 mmol) and stirred at 45° C. for 1 hour. The reaction solution was concentrated to give a white solid which was added with 500 ml of water and 500 ml saturated aqueous solution of sodium bicarbonate and filtered with stirring. The filter cake was washed with water to give compound 1-a-5 (17.7 g, 93%) as a white solid. MS m/z (ESI): 182.1 [M+H]$^+$.

Step e: Compound 1-a-5 (17.6 g, 97.1 mmol) and 110 ml of phosphorus oxychloride were added to a 500 ml flask and reacted at 100° C. for 4 hours. After completion of the reaction, phosphorus oxychloride was evaporated under reduced pressure, and iced water was added and stirred for 5 minutes. Iced ammonium hydroxide (25 ml) was slowly added dropwise to the system, stirred for 20 minutes and filtered. The filter cake was washed with a large amount of water to obtain a yellow solid. The crude yellow solid was dissolved in 1 L of dichloromethane, washed with water and saturated brine, respectively, and dried over anhydrous sodium sulfate to give compound 1-a-6 (17.4 g, 90%) as a yellow solid. MS m/z (ESI): 199.7 [M+H]$^+$.

Step f: Compound 1-a-6 (10 g, 50.1 mmol), 500 ml of tetrahydrofuran and 250 ml of methanol were added to a 1 L flask, and N-bromosuccinimide (8.91 g, 50.1 mmol) was slowly added under ice bath. After completion of the reaction at room temperature, the reaction mixture was concentrated to give a yellow solid which was dissolved in 500 ml of methylene chloride, washed with water and saturated brine, respectively, and dried and concentrated to give about 14 g of crude compound 1-a-7 as a yellow solid.

Step g: About 14 g of crude compound 1-a-7 was dissolved in 150 ml of isopropanol at 55° C. and 3.98 g of sodium borohydride (50 mmol) was added slowly in batches to the system and then heated to 60° C. The reaction was carried out for 3 hours. After the reaction was completed, the mixture was cooled to room temperature, filtered, and the filter cake was washed with dichloromethane and the filtrate was concentrated to obtain a viscous liquid. The crude product was dissolved in 300 ml of dichloromethane and 12.5 g of 2,3-dichloro-5,6-dicyano-p-benzoquinone (55.1 mmol) was slowly added in batches to the reaction solution. The mixture was stirred at room temperature for 2 hours. After completion of the reaction, the filtrate was concentrated to give the crude product which was purified by column chromatography (petroleum ether/ethyl acetate=40: 1-20:1) to give compound 1-a as yellow solid (9.8 g, 774%). MS m/z (ESI): 244.0 [M+H]$^+$. $^1$H NMR (400 MHz, DMSO-d6): δ 8.956 (s, 1H), 7.095 (s, 2H), 2.578 (s, 3H).

The Preparation of Compound 2-a

Step a: The reaction substrate 2-a-1 (10.6 g, 58 mmol) was placed in a 500 mL reaction flask and the substrate was dissolved by the addition of tetrahydrofuran/water (100 mL/60 mL). At room temperature, ammonium chloride (15.5 g, 292 mmol) and reduced iron powder (26 g, 467 mmol) were added successively to the reaction flask with stirring, followed by heating the reaction system to 65° C. and stirring for 3 hours. The reaction was monitored by TLC. After the substrate was completely reacted, the excess iron was removed by filtration and the filter cake was rinsed three times with ethyl acetate. The filtrate was extracted three times with ethyl acetate/water system. The organic layer was separated, washed with water and saturated brine, dried over anhydrous sodium sulfate and concentrated under reduced pressure to give compound 2-a-2 (8.0 g) which was directly used in the next reaction. Yield: 93%; Purity: 90%; MS m/z (ESI): 142.0 [M+H]$^+$.

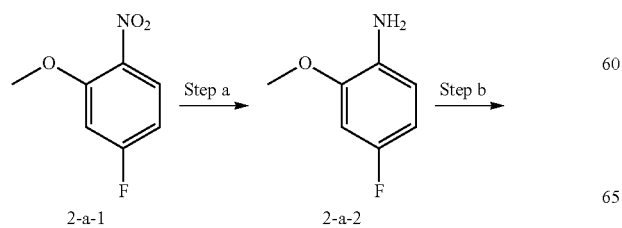

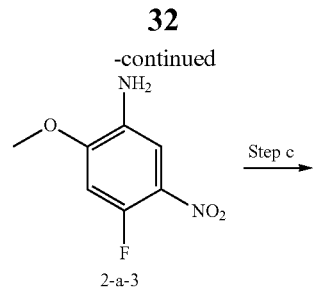

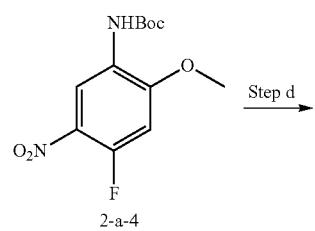

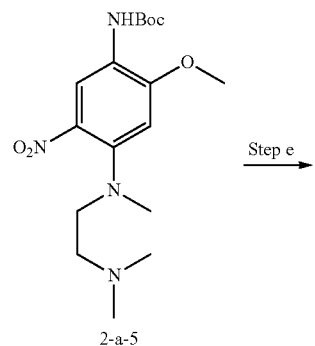

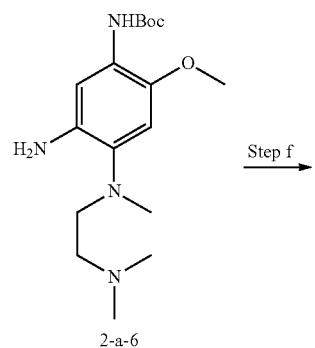

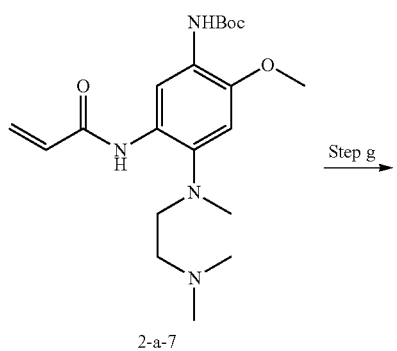

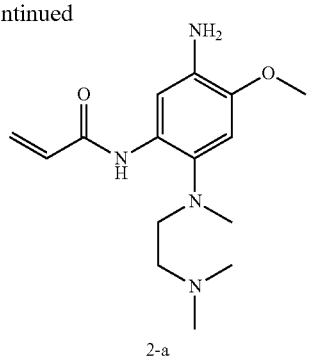

2-a

Step b: Compound 2-a-2 (8.0 g, 43 mmol) was placed in a 500 mL reaction flask and concentrated sulfuric acid (100 mL) was added with stirring to dissolve the substrate. Concentrated nitric acid (6.15 mL, 48 mmol) was slowly added dropwise to the reaction flask with stirring at −20° C. and stirred at this temperature for 5 minutes. The progress of the reaction was monitored by TLC until the substrate was completely reacted and the reaction mixture was poured into iced water. At −20° C. in ice bath, sodium hydroxide/water (150 mL/300 mL) was slowly added to the reaction system to adjust the pH to 8-9. The reaction solution after completion of neutralization was extracted three times with ethyl acetate/water system. The organic layer was separated, washed with water and saturated brine, dried over anhydrous sodium sulfate and concentrated under reduced pressure to give compound 4-fluoro-2-methoxy-5-nitroaniline 2-a-3 (8.7 g) which was used directly in the next step. Yield: 80%; Purity: 100%; MS In/z (ESI): 187.0 [M+H]$^+$; $^1$H NMR (400 MHz, DMSO-d6): δ 7.34 (d, J=7.8 Hz, 1H), 7.04 (d, J=13.4 Hz, 1H), 5.25 (brs, 2H), 3.90 (s, 3H).

Step c: Compound 2-a-3 (11.16 g, 60 mmol) was dissolved in dichloromethane (150 mL), triethylamine (12.24 g, 120 mmol), di-tert-butyl dicarbonate (15.60 g, 72 mmol), and 4-dimethylaminopyridine (0.74 g, 6 mmol) were added. The mixture was stirred at room temperature for 18 hours and then filtered. The filtrate was dried by rotary evaporation. The residue was purified by column chromatography (PE:EA=4:1) to give orange solid 2-a-4 (12.56 g, yield: 73%). MS m/z (ESI): 285 [M+H]$^+$. Purity=97% (UV254).

Step d: Compound 2-a-4 (11.46 g, 40 mmol) was dissolved in DMA (60 mL) and N,N,N'-trimethylethylenediamine (4.90 g, 48 mmol) and N,N-diisopropylethylamine (7.74 g, 60 mmol) were added. The mixture was heated to 90° C. under nitrogen and stirred for 6 hours. After cooled to room temperature, the mixture was poured into iced water and extracted with ethyl acetate (400 mL). The organic phase was separated and washed with brine (300 mL). The mixture was dried over anhydrous sodium sulfate and filtered. The filtrate was dried by rotary evaporation to give an orange solid 2-a-5 (12.51 g, yield: 85%). MS in/z (ESI): 369 [M+H]$^+$, purity=98% (UV214).

Step e: Compound 2-a-5 (12 g, 32.6 mmol) was dissolved in methanol (200 mL) and Pd/C (1.0 g) was added. The mixture was hydrogenated with hydrogen balloon at room temperature for 1 hour and then filtered. The filtrate was dried by rotary evaporation to give black solid 2-a-6 (10.70 g, yield: 97%). MS m/z (ESI): 339 [M+H]$^+$, purity=97% (UV254).

Step f: Compound 2-a-6 (10.1 g, 30 mmol) and triethylamine (6.12 g, 60 mmol) were dissolved in dichloromethane (200 mL) and cooled to 0° C. Acryloyl chloride (3.24 g, 36 mmol) was added. The mixture was stirred under nitrogen at room temperature for 3 hours. The reaction mixture was washed with saturated aqueous sodium bicarbonate solution (200 mL) and brine (200 mL). The mixture was dried over anhydrous sodium sulfate and filtered. The filtrate was dried by rotary evaporation to give brown solid 2-a-7 (9.64 g, yield: 82%). MS in/z (ESI): 393 [M+H]$^+$, purity=88% (UV254).

Step g: Compound 2-a-7 (9.41 g, 24 mmol) was dissolved in dichloromethane (100 mL) and cooled to 0° C. and trifluoroacetic acid (20 mL) was added. The mixture was stirred under nitrogen at room temperature for 18 hours. The reaction mixture was dried by rotary evaporation. The residue was dissolved in dichloromethane (300 mL) and washed with saturated aqueous sodium bicarbonate solution (200 mL) and brine (200 mL). The mixture was dried over anhydrous sodium sulfate and filtered. The filtrate was dried by rotary evaporation and the residue was purified by column chromatography (DCM:MeOH=10:1) to give orange oil 2-a (3.26 g, yield: 46.5%). MS m/z (ESI): 293 [M+H]$^+$, Purity=99% (UV214). $^1$H NMR (400 MHz, CDCl-3) δ: 10.07 (s, 1H), 7.98 (s, 1H), 7.26 (s, 1H), 6.40 (dd, J=16.8, 1.6 Hz, 1H), 6.29-6.32 (m, 1H), 5.66 (dd, J=10.0, 1.6 Hz, 1H), 3.81 (s, 3H), 3.76 (s, 2H), 2.85 (t, J=5.6 Hz, 2H), 2.65 (s, 3H), 2.25 (s, 8H).

The Preparation of Compound 3-a

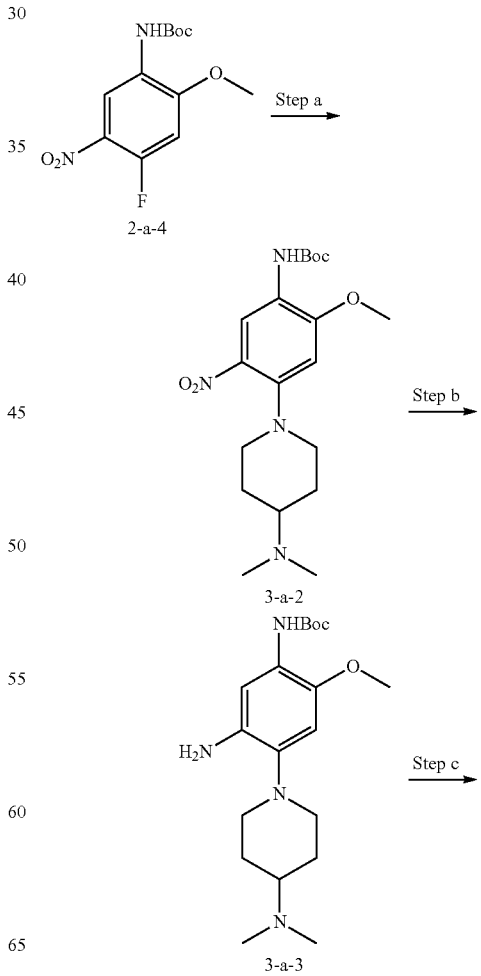

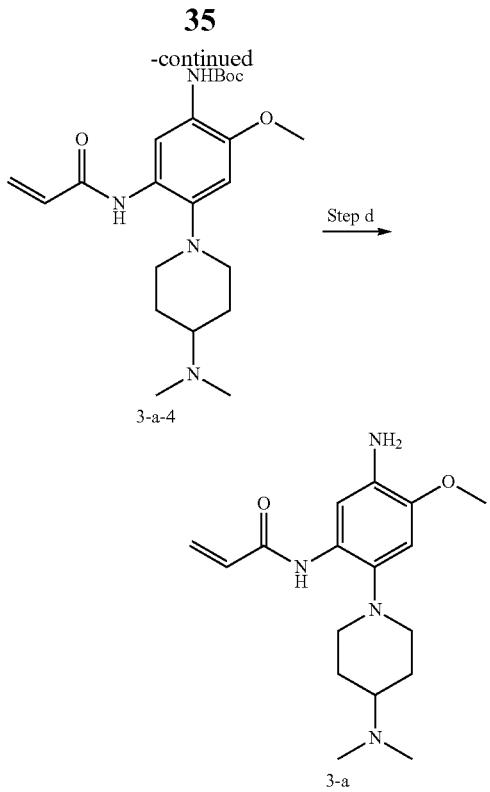

Step a: Compound 2-a-4 (14.0 g, 50 mmol) was dissolved in DMA (70 mL), 4-dimethylaminopiperidine (7.56 g, 60 mmol) and N,N-diisopropylethylamine (12.9 g, 100 mmol) were added. The mixture was heated to 90° C. under nitrogen and stirred for 6 hours. After cooled to room temperature, the mixture was poured into iced water and extracted with ethyl acetate (400 mL). The organic phase was separated and washed with brine (300 mL). The mixture was dried over anhydrous sodium sulfate and filtered. The filtrate was dried by rotary evaporation to give 3-a-2 as an orange solid (19.1 g, yield: 81%). MS m/z (ESI): 395 [M+H]$^+$, purity=99% (UV214).

Step b: Compound 3-a-2 (15.76 g, 40 mmol) was dissolved in methanol (150 mL) and Pd/C (2.0 g) was added. The mixture was hydrogenated with hydrogen balloon at room temperature for 1 hour and then filtered. The filtrate was dried by rotary evaporation to give black solid 3-a-3 (13.41 g, yield: 92%). MS m/z (ESI): 365 [M+H]$^+$, purity=93% (UV214).

Step c: Compound 3-a-3 (11 g, 30 mmol) and triethylamine (6.2 g, 60 mmol) were dissolved in dichloromethane (150 mL) and cooled to 0° C. Acryloyl chloride (3.24 g, 36 mmol) was added. The mixture was stirred under nitrogen at room temperature for 3 hours. The reaction mixture was washed with saturated aqueous sodium bicarbonate solution (200 mL) and brine (200 mL). The mixture was dried over anhydrous sodium sulfate and filtered. The filtrate was dried by rotary evaporation to give brown solid 3-a-4 (9.61 g, yield: 77%). MS m/z (ESI): 393 [M+H]$^+$, purity=91% (UV254).

Step d: Compound 3-a-4 (6.27 g, 15 mmol) was dissolved in dichloromethane (100 mL), cooled to 0° C. and trifluoroacetic acid (30 mL) was added. The mixture was stirred under nitrogen for 24 hours at room temperature. The reaction mixture was dried by rotary evaporation. The residue was dissolved in dichloromethane (300 mL) and washed with saturated aqueous sodium bicarbonate solution (200 mL) and brine (200 mL). The mixture was dried over anhydrous sodium sulfate and filtered. The filtrate was dried by rotary evaporation and the residue was purified by column chromatography (DCM:MeOH=20:1) to give orange solid 3-a (3.4 g, yield: 71%). MS m/z (ESI): 319 [M+H]$^+$, purity=96% (UV214). $^1$H NMR (400 MHz, CDCl-3) δ: 8.50 (s, 1H), 7.93 (s, 1H), 6.61 (s, 1H), 6.32-6.35 (m, 2H), 5.73 (dd, J=8.8, 2.8 Hz, 1H), 3.80 (s, 5H), 3.01-3.05 (m, 3H), 2.71-2.77 (m, 8H), 2.14-2.17 (m, 2H), 1.90-1.99 (m, 2H).

Example 1: The Preparation of N-(2-((2-(dimethylamino)ethyl)(methyl)amino)-4-methoxy-5-(7-(1-methyl-1H-pyrazol-4-yl)pyrrolo[1,2-f][1,2,4]triazin-2-ylamino)phenyl)acrylamide (J-1)

Step 1: Compound 1-a (6.0 g, 24.6 mmol), 1-methyl-4(4,4,5,5-tetramethyl-1,3,2-dioxaborolan-2-yl)-1H-pyrazole (10.2 g, 49.0 mmol), tetrakis(triphenylphosphine)palladium (2.84 g, 2.46 mmol), potassium carbonate (10.2 g, 73.8 mmol), dioxane 60 ml, and water 20 ml were mixed under Argon and stirred at 100° C. for 4 hours. The reaction was completed and the mixture was cooled to room temperature. Dichloromethane and water were added. The organic phase was separated and concentrated under reduced pressure to give crude product which was purified by Combi-flash column chromatography [PE:EA=100:0-0:100] to give compound 1-b (5.7 g) as yellow solid which was used directly in the next step. Yield: 94.5%; Purity: 98.76% (UV254). MS m/z (ESI): 246.0[M+H]$^+$.

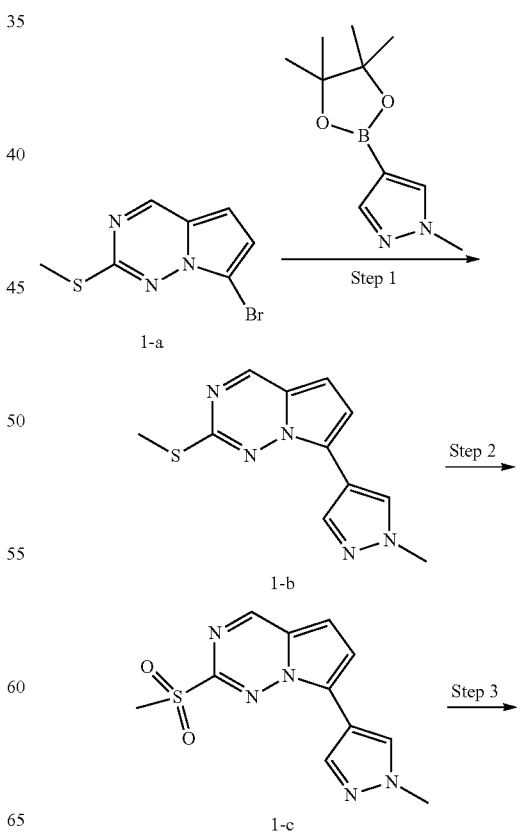

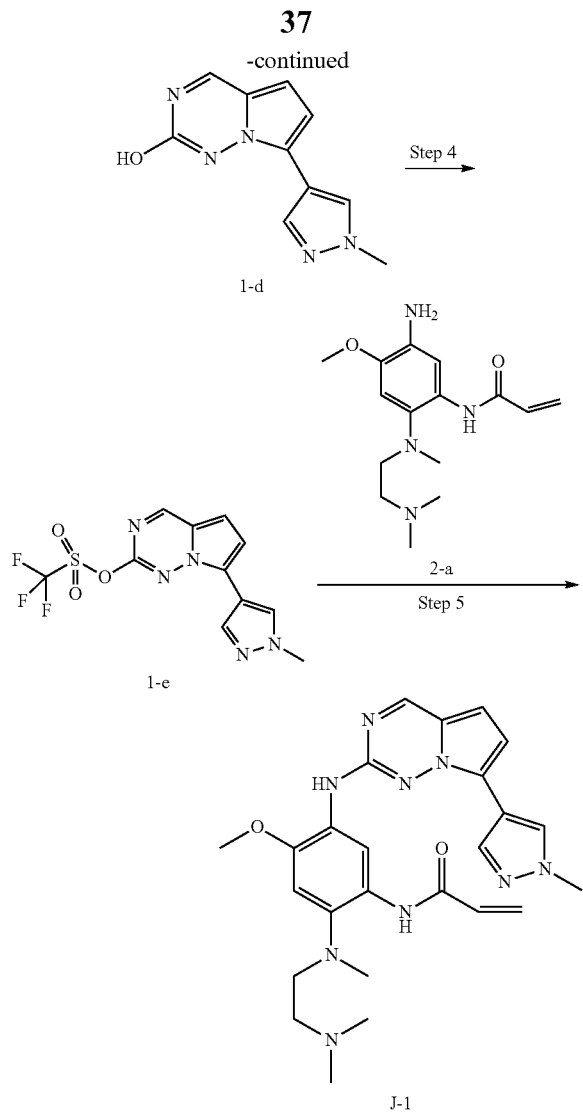

pressure to give a reddish brown solid compound 1-d (1.2 g) which was used directly in the next step. Yield: 80.8%; Purity: 71% (UV254). MS m/z (ESI): 216.1 [M+H]⁺.

Step 4: Compound 1-d (1.2 g, 3.96 mmol) was dissolved in 10 ml of dimethylformamide and then N-phenyl bis (trifluoromethanesulfonimide) (2.1 g. 5.88 mmol) and N,N-diisopropylethylamine (1.5 g, 11.61 mmol) were added and stirred at room temperature for 3 hours. After the reaction was complete, 50 ml of methylene chloride was added and the organic phase was washed with water twice. The organic phase was separated, dried over anhydrous sodium sulfate and filtered. The filtrate was concentrated under reduced pressure to give crude product which was purified by Combi-flash column chromatography [PE:EA=100:0-80:20] to give semi-solid compound 1-e (160 mg) which was used directly in the next step. Yield: 11.6%; Purity: 68% (UV254). MS m/z (ESI): 348.0 [M+H]⁺.

Step 5: Tris (dibenzylideneacetone) dipalladium (8 mg, 0.0086 mmol) was added to a solution of compound 1-e (30 mg, 0.086 mmol), compound 2-a (25 mg, 0.086 mmol), 4,5-bis(diphenylphosphino)-9,9-dimethylxanthene (10 mg, 0.0172) and cesium carbonate (6 mg, 0.0072 mmol) in 4 ml of dioxane under argon and stirred at 160° C. under microwave for 15 minutes. After the reaction was completed, the mixture was cooled to room temperature, filtered, and the filtrate was concentrated under reduced pressure to give 107 mg of crude product which was purified by preparative liquid phase to give compound J-1 (10.16 mg), yield: 23.8%; purity: 97.83% (UV254). MS m/z (ESI): 490.2 [M+H]⁺. ¹H NMR (400 MHz, DMSO) δ 10.22 (s, 1H), 8.83 (s, 1H), 8.76 (s, 1H), 8.38 (s, 1H), 8.01 (s, 1H), 7.88 (s, 1H), 7.06-7.05 (d, J=4.7 Hz, 2H), 6.89-6.88 (d, J=4.7 Hz, 1H), 6.45-6.38 (dd, J1=10.2 Hz, J2=16.9 Hz, 1H), 6.21-6.17 (dd, J1=1.8 Hz, J2=16.9 Hz, 1H), 5.76-5.73 (dd, J1=1.8 Hz, J2=10.1 Hz, 1H), 3.82 (s, 3H), 3.75 (s, 3H), 2.90-2.88 (t, J=4.7 Hz, 2H), 2.73 (s, 3H), 2.33 (s, 2H), 2.22 (s, 6H).

Example 2: The Preparation of N-(2-(4-(dimethylamino)piperidin-1-yl)-4-methoxy-5-(7-(1-methyl-1H-pyrazol-4-yl)pyrrolo[1,2-f][1,2,4]triazin-2-ylamino)phenyl)acrylamide (J-2)

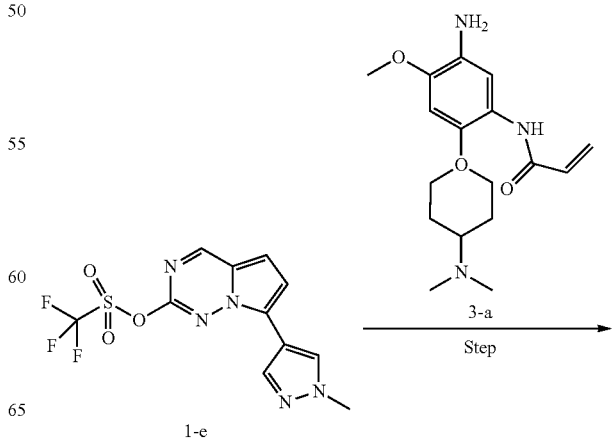

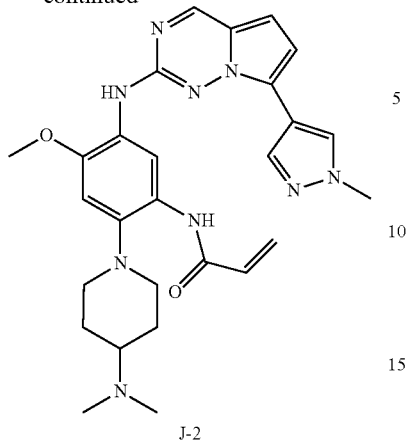

J-2

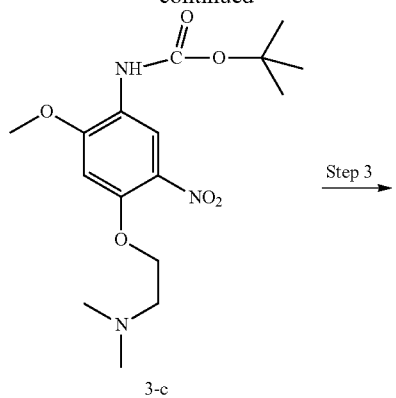

3-c

Step: Compound 1-e (50 mg, 0.098 mmol), compound 3-a (32 mg, 0.1 mmol), tris(dibenzylideneacetone) dipalladium (9 mg, 0.0098 mmol), 4,5-bis(diphenylphosphino)-9,9-dimethylxanthene (9 mg, 0.016 mmol) and cesium carbonate (64 mg, 0.196 mmol) were added to 4 mL of diaxane under argon and stirred at 120° C. under microwave for 10 minutes. After the reaction was complete, the mixture was cooled to room temperature, and filtered through diatomaceous earth. The filter cake was washed with dichloromethane. The filtrate was concentrated under reduced pressure to give the crude product which was purified by preparative liquid to obtain a yellow solid compound J-2 (5.67 mg) in a yield of 11.2%. Purity: 100% (UV254). MS m/z (ESI): 516.0 [M+H]$^+$. $^1$H NMR (400 MHz, DMSO) δ 9.11 (s, 1H), 8.84 (s, 1H), 8.48 (s, 1H), 8.34 (s, 1H), 8.04 (s, 1H), 7.88 (s, 1H), 7.07 (d, J=4.7 Hz, 1H), 6.90 (s, 1H), 6.89 (s, 1H), 6.72 (dd, J=16.8, 10.5 Hz, 1H), 6.19 (d, J=15.2 Hz, 1H), 5.74 (d, J=11.7 Hz, 1H), 3.84 (s, 3H), 3.80 (s, 3H), 3.07 (d, J=10.4 Hz, 2H), 2.76-2.65 (m, 2H), 2.27 (s, 7H), 1.86 (d, J=12.0 Hz, 2H), 1.73 (m, 2H).

Example 3: The Preparation of N-(2-(2-(dimethylamino)ethoxyl)-4-methoxy-5-(7-(1-methyl-1H-pyrazol-4-yl)pyrrolo[1,2-f][1,2,4]triazin-2-ylamino)phenyl)acrylamide (J-3)

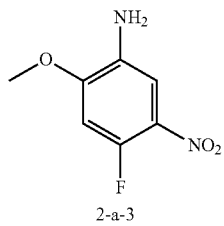

2-a-3

Step 1

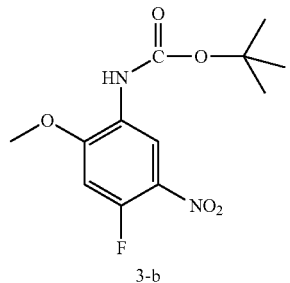

3-b

Step 2

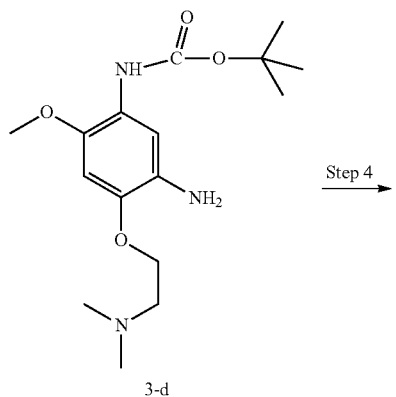

3-d

Step 4

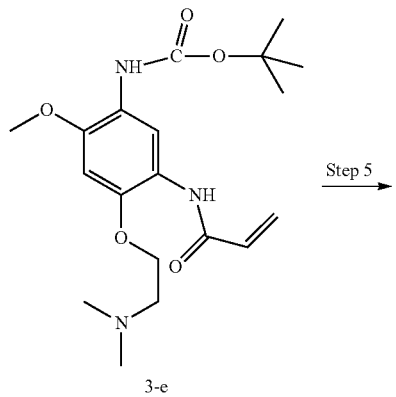

3-e

Step 5

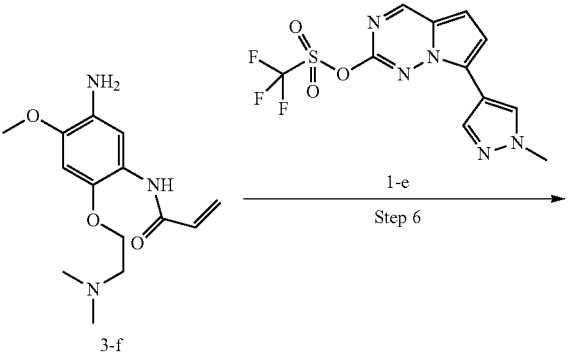

3-f 1-e
Step 6

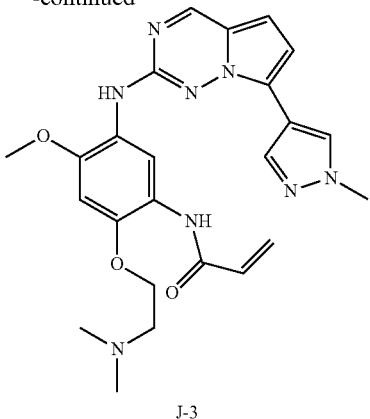

J-3

Step 1: Compound 2-a-3 (25 g, 134.3 mmol) was dissolved in 200 ml of methylene chloride and cooled to 5° C. 4-dimethylaminopyridine (3.3 g, 27 mmol) was added and di-tert-butyl dicarbonate (33 g, 151.2 mmol) was added slowly and stirred at room temperature overnight. After the reaction was complete, the mixture was filtered through celatom and the filter cake was washed with dichloromethane. The filtrate was concentrated under reduced pressure to give 38 g of brown crystalline solid, which was purified by Combi-flash column chromatography [PE:EA=90:10~80:20] to give compound 3-b (13.6 g) as a pale yellow crystal which was used directly in the next step. Yield: 35.4%; purity: 92.41% (UV254). MS m/z (EST): 231.0 [M−55]+.

Step 2: Compound 2-(dimethylamino) ethanol (2.26 g, 25.34 mmol) was dissolved in 55 ml of tetrahydrofuran and cooled to 0° C. Sodium hydride (1.093 g, 27.325 mmol) was slowly added under argon and stirred at room temperature for 3 hours. A solution of compound 3-b (5.4 g, 17.49 mmol) in 31 ml of tetrahydrofuran was slowly added and stirred at room temperature overnight. After the reaction was complete, the reaction solution was concentrated under reduced pressure to give the crude product which was purified by Combi-flash column chromatography [DCM:MeOH=100:0-90:10] to give compound 3-c (6.66 g) as a yellow solid which was used directly in the next reaction. Yield: 99.34%; Purity: 91.01% (UV254). MS m/z (ESI): 356.1 [M+H]+.

Step 3: Compound 3-c (6.66 g, 17.06 mmol) was dissolved in 150 ml of methanol, palladium on charcoal (600 mg) was added, and the mixture was stirred at room temperature for 5 hours under hydrogen. After the reaction was finished, the reaction mixture was filtered, washed with methanol and the filtrate was concentrated under reduced pressure to give compound 3-d (6.06 g) as a dark brown oil which was used directly in the next step. Yield: 109.19%; purity: 66.01% (UV254). MS m/z (ESI): 326.1 [M+H]+.

Step 4: Compound 3-d (6.06 g, 12.29 mmol) was dissolved in 50 ml of dichloromethane, cooled to 0° C., and N,N-diisopropylethylamine (3.18 g, 24.61 mmol) was added and stirred for 5 minutes. A solution of acryloyl chloride (1.45 g, 16.02 mmol) in 10 ml of dichloromethane was added and the mixture was warmed to room temperature and stirred for 2 hours. After completion of the reaction, 25 ml of saturated sodium bicarbonate solution was added and stirred for 10 minutes, and then the mixture was washed with water and saturated brine. The organic phase was separated, dried over anhydrous sodium sulfate and filtered. The filtrate was concentrated under reduced pressure to give crude product which was purified by Combi-flash column chromatography [DCM: (10% $NH_3.H_2O$) MeOH=100:0-80:20] to give the light brown solid compound 3-e (2.29 g) which was used directly in the next step. Yield: 49.1%; purity: 97.24% (UV254). MS m/z (ESI): 380.2[M+H]+.

Step 5: Compound 3-e (2.29 g, 5.87 mmol) was dissolved in 50 ml of dichloromethane and cooled to 0° C. Trifluoroacetic acid (13.39 g, 117.44 mmol) was slowly added and stirred at room temperature overnight. After the reaction was finished, the reaction solution was concentrated under reduced pressure, dissolved in dichloromethane and extracted with hydrochloric acid (1N). The aqueous phase was adjusted to pH 9 with sodium carbonate solution and extracted with dichloromethane/methanol. The combined organic phases were separated, dried over anhydrous sodium sulfate and filtered. The filtrate was concentrated under reduced pressure and purified by Combi-flash column chromatography [DCM: (10% $NH_3.H_2O$) MeOH=100:0-80:20] to give compound 3-f (1.1 g) as a dark brown oil which was directly used in the next step. Yield: 67.07%; purity: 99.38% (UV254). MS m/z (ESI): 280.1 [M+H]+.

Step 6: Compound 1-e (50 mg, 0.098 mmol), compound 3-f (28 mg, 0.1 mmol), tris(dibenzylideneacetone) dipalladium (9 mg, 0.0098 mmol), 4,5-bis(diphenylphosphino)-9,9-dimethylxanthene (9 mg, 0.016 mmol), and cesium carbonate (64 mg, 0.196 mmol) were added to a 4 ml of dioxane solution and stirred with microwave at 120° C. for 10 minutes under argon. After the reaction was terminated, the mixture was cooled to room temperature and filtered through celatom. The filter cake was washed with dichloromethane. The filtrate was concentrated under reduced pressure to give the crude product which was separated and purified by preparative liquid chromatography to give compound J-3 (7.71 mg) as a yellow solid. Yield: 16.5%; purity: 100% (UV254). MS m/z (ESI): 477.0[M+H]+. $^1$H NMR (400 MHz, DMSO) δ 9.81 (s, 1H), 8.82 (s, 1H), 8.50 (s, 1H), 8.30 (s, 1H), 8.00 (s, 1H), 7.89 (s, 1H), 7.04 (d, J=4.7 Hz, 1H), 6.97 (s, 1H), 6.87 (d, J=4.7 Hz, 1H), 6.56-6.41 (m, 1H), 6.18 (d, J=15.1 Hz, 1H), 5.73 (d, J=12.2 Hz, 1H), 4.20 (t, J=5.7 Hz, 2H), 3.82 (s, 3H), 3.76 (s, 3H), 2.60 (t, J=5.6 Hz, 2H), 2.27 (s, 6H).

Example 4: The Preparation of N-(4-methoxy-5-(7-(1-methyl-1H-pyrazol-4-yl)pyrrolo[1,2-f][1,2,4]triazin-2-ylamino)-2-(4-methyl-1-yl)phenyl)acrylamide (J-4)

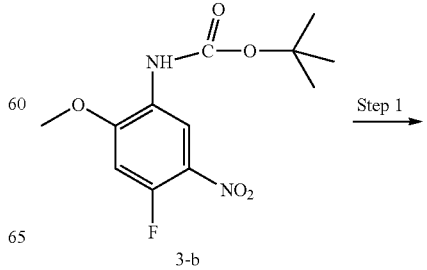

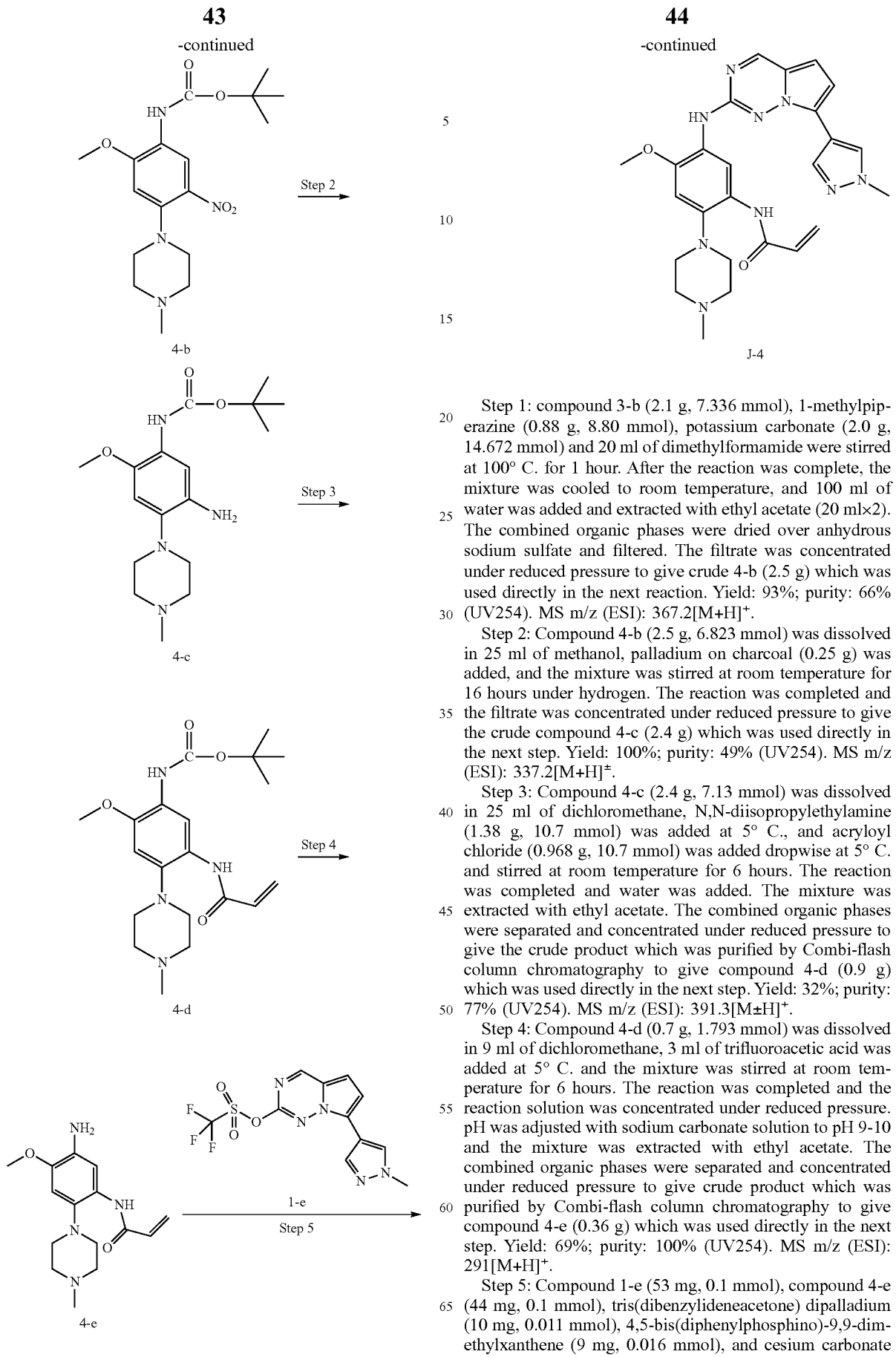

Step 1: compound 3-b (2.1 g, 7.336 mmol), 1-methylpiperazine (0.88 g, 8.80 mmol), potassium carbonate (2.0 g, 14.672 mmol) and 20 ml of dimethylformamide were stirred at 100° C. for 1 hour. After the reaction was complete, the mixture was cooled to room temperature, and 100 ml of water was added and extracted with ethyl acetate (20 ml×2). The combined organic phases were dried over anhydrous sodium sulfate and filtered. The filtrate was concentrated under reduced pressure to give crude 4-b (2.5 g) which was used directly in the next reaction. Yield: 93%; purity: 66% (UV254). MS m/z (ESI): 367.2[M+H]$^+$.

Step 2: Compound 4-b (2.5 g, 6.823 mmol) was dissolved in 25 ml of methanol, palladium on charcoal (0.25 g) was added, and the mixture was stirred at room temperature for 16 hours under hydrogen. The reaction was completed and the filtrate was concentrated under reduced pressure to give the crude compound 4-c (2.4 g) which was used directly in the next step. Yield: 100%; purity: 49% (UV254). MS m/z (ESI): 337.2[M+H]$^±$.

Step 3: Compound 4-c (2.4 g, 7.13 mmol) was dissolved in 25 ml of dichloromethane, N,N-diisopropylethylamine (1.38 g, 10.7 mmol) was added at 5° C., and acryloyl chloride (0.968 g, 10.7 mmol) was added dropwise at 5° C. and stirred at room temperature for 6 hours. The reaction was completed and water was added. The mixture was extracted with ethyl acetate. The combined organic phases were separated and concentrated under reduced pressure to give the crude product which was purified by Combi-flash column chromatography to give compound 4-d (0.9 g) which was used directly in the next step. Yield: 32%; purity: 77% (UV254). MS m/z (ESI): 391.3[M±H]$^+$.

Step 4: Compound 4-d (0.7 g, 1.793 mmol) was dissolved in 9 ml of dichloromethane, 3 ml of trifluoroacetic acid was added at 5° C. and the mixture was stirred at room temperature for 6 hours. The reaction was completed and the reaction solution was concentrated under reduced pressure. pH was adjusted with sodium carbonate solution to pH 9-10 and the mixture was extracted with ethyl acetate. The combined organic phases were separated and concentrated under reduced pressure to give crude product which was purified by Combi-flash column chromatography to give compound 4-e (0.36 g) which was used directly in the next step. Yield: 69%; purity: 100% (UV254). MS m/z (ESI): 291[M+H]$^+$.

Step 5: Compound 1-e (53 mg, 0.1 mmol), compound 4-e (44 mg, 0.1 mmol), tris(dibenzylideneacetone) dipalladium (10 mg, 0.011 mmol), 4,5-bis(diphenylphosphino)-9,9-dimethylxanthene (9 mg, 0.016 mmol), and cesium carbonate (68 mg, 0.21 mmol) were added to 4 mL of dioxane solution under argon and stirred under microwave at 120° C. for 10 minutes. The reaction was completed and the reaction solution was cooled to room temperature and filtered through celatom. The filter cake was washed with dichloromethane and the filtrate was concentrated under reduced pressure to give the crude product which was separated and purified by preparative liquid chromatography to obtain yellow solid compound J-4 (5.89 mg). Yield: 11.6%; purity: 100% (UV254). MS m/z (ESI): 488.0[M+H]$^+$. $^1$H NMR (400 MHz, DMSO) δ 9.09 (s, 1H), 8.83 (s, 1H), 8.44 (s, 1H), 8.32 (s, 1H), 8.03 (s, 1H), 7.88 (s, 1H), 7.06 (d, J=4.7 Hz, 1H), 6.92 (s, 1H), 6.89 (d, J=4.7 Hz, 1H), 6.70-6.60 (m, 1H), 6.18 (d, J=15.3 Hz, 1H), 5.73 (d, J=11.7 Hz, 1H), 3.84 (s, 3H), 3.80 (s, 3H), 2.88 (t, J=4.7 Hz, 4H), 2.55 (s, 4H), 2.26 (s, 3H).

Example 5: The Preparation of N-(5(7-cyclohexenyl-pyrrolo[1,2-f][1,2,4]triazin-2-ylamino)-2-((2-(dimethylamino)ethyl)(methyl)amino)-4-methoxyphenyl)acrylamide (J-5)

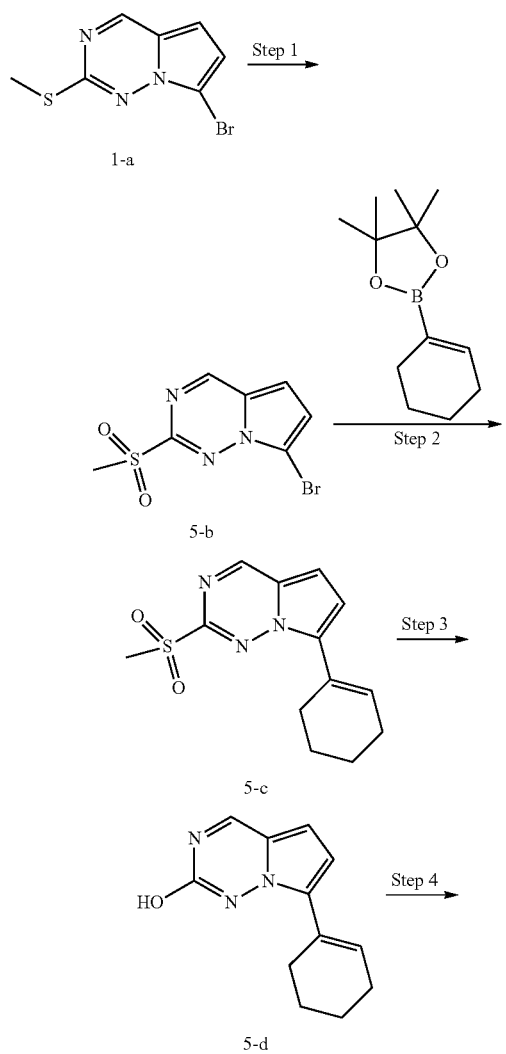

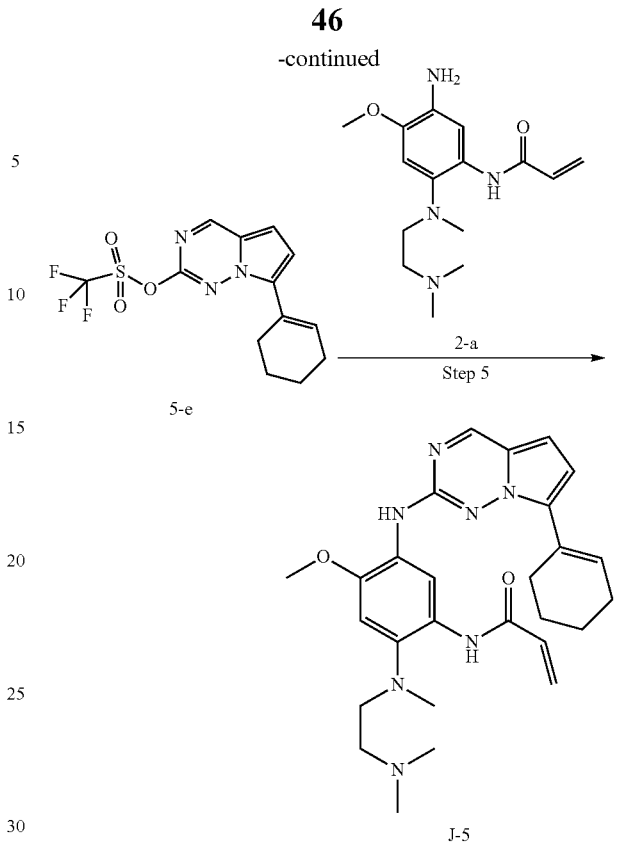

Step 1: Compound 1-a (2.3 g, 9.4 mmol) was dissolved in 200 ml of dichloromethane and cooled to 0° C. m-CPBA (m-chloroperoxybenzoic acid)(6.5 g, 37.7 mmol) was added slowly. After the addition, the mixture was stirred at room temperature for 2 h. The reaction was completed and 200 ml saturated sodium thiosulfate solution was added and stirred for 1 h. The organic phase was separated, and washed with saturated sodium bicarbonate. The organic phase was separated, dried over anhydrous sodium sulfate and filtered. The filtrate was concentrated under reduced pressure to give solid compound 5-b (733 mg) which was used directly in the next reaction. Yield: 28.2%; purity: 84.2% (UV254). MS m/z (ESI): 275.8[M+H]$^+$.

Step 2: Compound 5-b (650 mg, 1.98 mmol), 2-cyclohexenyl-4,4,5,5-tetramethyl-1,3,2-dioxaborolane (825 mg, 3.96 mmol), tetrakis(triphenylphosphine)palladium (145 mg, 0.198 mmol), and sodium carbonate (630 mg, 5.94 mmol) were added to a mixed solution of dioxane 12 ml/water 4 ml under argon and stirred under microwave at 120° C. for 15 minutes. The reaction was completed and the mixture was cooled to room temperature. 50 ml of dichloromethane was added and the mixture was filtered through celatom. The filtrate was extracted with water/dichloromethane, washed with saturated brine, dried over anhydrous sodium sulfate and filtered. The filtrate was concentrated under reduced pressure to give the crude product which was separated and purified by Combi-flash column chromatography [PE:EA=100:0-0:100] to give compound 5-c (251 mg) as an orange solid which was used directly in the next reaction. Yield: 45.7%; purity: 81.54% (UV254). MS m/z (ESI): 278.1 [M+H]$^+$.

Step 3: Compound 5-c (249 mg, 0.73 mmol) was added to 4 mL of aqueous solution of sodium hydroxide (300 mg, 7.5 mmol) and stirred at 100° C. for 2 h. The reaction was completed, the mixture was cooled to 0° C., and acetic acid was added slowly to adjust pH to 5, with solid precipitated. It was extracted with dichloromethane. The combined organic phases were separated, dried over anhydrous sodium sulfate and filtered. The filtrate was concentrated under reduced pressure to give compound 5-d (240 mg) as a brown solid which was used directly in the next reaction. Yield: 152.87%; purity: 84.55% (UV254). MS m/z (ESI): 216.2 [M+H]$^+$.

Step 4: Compound 5-d (240 mg, 0.94 mmol) was dissolved in 10 ml of dimethylformamide and cooled to 0° C. N,N-diisopropylethylamine (183 mg, 1.42 mmol) was added and stirred for 10 minutes. N-phenyl bis(trifluoromethanesulfonimide) (370 mg, 1 mmol) was added and stirred at room temperature for 3 h. The reaction was completed and the reaction solution was concentrated under reduced pressure to give the crude product which was purified by Combi-flash column chromatography [PE:EA=100:0-80:20] to give compound 5-e (43 mg) as a yellow solid which was used directly in the next reaction. Yield: 13.2%; purity: 53% (UV254). MS m/z (ESI): 348.1 [M+H]$^+$.

Step 5: Compound 5-e (23 mg, 0.066 mmol), compound 2-a (20 mg, 0.068 mmol), tris(dibenzylideneacetone) dipalladium (6 mg, 0.0066 mmol), 4,5-bis(diphenylphosphino)-9,9-dimethylxanthene (6 mg, 0.01 mmol), and cesium carbonate (43 mg, 0.132 mmol) were added to 3 ml of dioxane solution under argon and stirred at 140° C. under microwave for 15 minutes. The reaction was completed and the reaction solution was cooled to room temperature and filtered through celatom. The filter cake was washed with dichloromethane and the filtrate was concentrated under reduced pressure to give the crude product which was purified by preparative liquid chromatography to obtain compound J-5 (3.46 mg) as a yellow solid. Yield: 9.79%; purity: 100% (UV254). MS m/z (ESI): 490.4 [M+H]$^+$. $^1$H NMR (400 MHz, DMSO) δ 10.16 (s, 1H), 8.85 (s, 1H), 8.66 (s, 1H), 8.25 (s, 1H), 7.74 (s, 1H), 7.03 (s, 1H), 6.99 (s, 1H), 6.82 (d, J=4.7 Hz, 1H), 6.76 (d, J=4.7 Hz, 1H), 6.42 (dd, J=16.9, 10.1 Hz, 1H), 6.21 (dd, J=17.0, 1.9 Hz, 1H), 5.74 (dd, J=10.1, 1.9 Hz, 1H), 3.84 (s, 3H), 2.90 (t, J=5.7 Hz, 2H), 2.69 (s, 3H), 2.42 (s, 2H), 2.35 (t, J=5.8 Hz, 2H), 2.24 (s, 6H), 2.08 (s, 2H), 1.70-1.60 (m, 2H), 1.59-1.48 (m, 2H).

Example 6: The Preparation of N-(2-((2-(dimethylamino)ethyl)(methyl)amino)-4-methoxy-5-(7-(pyridin-3-yl)pyrrolo[1,2-f][1,2,4]triazin-2-ylamino)phenyl)acrylamide (J-6)

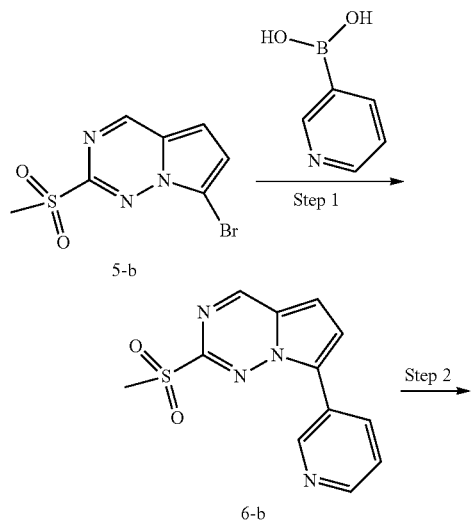

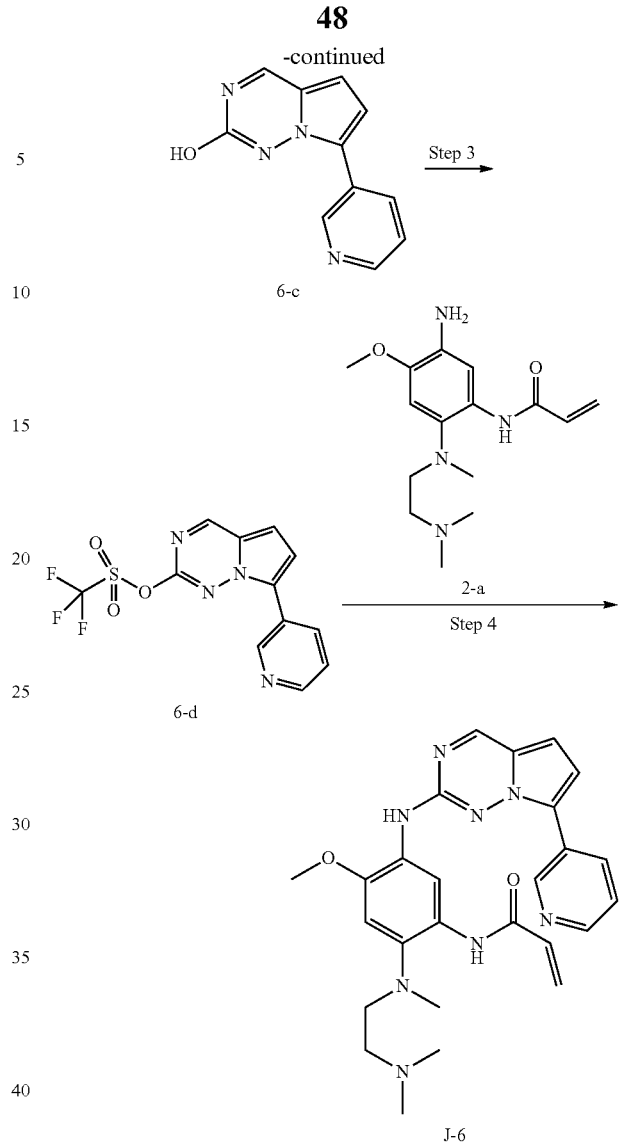

Step 1: [1,1'-bis(diphenylphosphino)ferrocene]dichloropalladium(II) (72 mg, 0.1 mmol) was added to a mixed solution of compound 5-b (552 mg, 2.0 mmol), pyridin-3-yl boric acid (246 mg, 2.0 mmol), and sodium carbonate (424 mg, 4.0 mmol) in dioxane 20 ml/water 5 ml under argon and stirred under microwave at 130° C. for 15 minutes. The reaction was completed and the mixture was cooled to room temperature, extracted with dichloromethane/water. The combined organic phases were separated, dried over anhydrous sodium sulfate and filtered. The filtrate was concentrated under reduced pressure to give compound 6-b (160 mg) as a yellow solid which was used directly in the next reaction. Yield: 29.1%; purity: 60% (UV254). MS m/z (ESI): 275.1 [M+H]$^+$.

Step 2: Compound 6-b (160 mg, 0.583 mmol) was added to sodium hydroxide solution (2 ml, 11.67 mmol) and stirred at 100° C. for 2 h. The reaction was completed, the mixture was cooled to 0° C., and acetic acid was added slowly to adjust pH to 4-5. The mixture was extracted with dichloromethane. The combined organic phases were separated, washed with saturated brine, dried over anhydrous sodium sulfate and filtered. The filtrate was concentrated under reduced pressure to give compound 6-c (130 mg) as a brown solid which was used directly in the next reaction. Yield: 100%; purity: 52% (UV254). MS m/z (ESI): 213.1 [M+H]+.

Step 3: N-phenyl bis(trifluoromethanesulfonimide) (297 mg, 0.79 mmol) was added to the solution of compound 6-c (130 mg, 0.61 mmol) and N,N-diisopropylethylamine (158 mg, 1.22 mmol) in 5 ml of dimethylformamide at 0° C. and stirred at room temperature for 1 h. The reaction was completed and the mixture was extracted with dichloromethane. The combined organic phases were separated, dried over anhydrous sodium sulfate and filtered. The filtrate was concentrated under reduced pressure to give the crude product which was separated and purified by Combi-flash column chromatography [PE:EA=100:0-40:60] to give compound 6-d (30 mg) as a yellow solid which was used directly in the next reaction. Yield: 15%; purity: 89% (UV254). MS m/z (ESI): 345[M+H]+.

Step 4: Compound 6-d (30 mg, 0.087 mmol), compound 2-a (25 mg, 0.085 mmol), tris(dibenzylideneacetone) dipalladium (8 mg, 0.0087 mmol), 4,5-bis(diphenylphosphino)-9,9-dimethylxanthene (10 mg, 0.017 mmol) and cesium carbonate (57 mg, 0.174 mmol) were added to 4 mL of dioxane solution under argon and stirred at 170° C. under microwave for 15 minutes. The reaction was completed and the reaction solution was cooled to room temperature and filtered. The filtrate was concentrated under reduced pressure to give the crude product which was separated and purified by preparative liquid chromatography to give compound J-6 (7.84 mg) as a pale yellow solid. Purity: 95.46% (UV254). MS m/z (ESI): 487.3[M+H]+. 1H NMR (500 MHz, DMSO) δ 10.13 (s, 1H), 9.15-9.14 (d, J=1.9 Hz, 1H), 8.99 (s, 1H), 8.65-8.63 (d, J=8.1 Hz, 1H), 8.60 (s, 1H), 8.41-8.40 (t, J=3.5 Hz, 1H), 8.12 (s, 1H), 7.32-7.31 (d, J=4.8 Hz, 1H), 7.28-7.25 (dd, J$_1$=4.8 Hz, J$_2$=8.0 Hz, 1H), 7.01 (s, 1H), 6.97-6.96 (d, J=4.8 Hz, 1H), 6.45-6.40 (dd, J$_1$=10.2 Hz, J$_2$=17.0 Hz, 1H), 6.18-6.15 (dd, J$_1$=1.6 Hz, J$_2$=17.0 Hz, 1H), 5.76-5.73 (dd, J$_1$=1.5 Hz, J$_2$=10.1 Hz, 1H), 3.81 (s, 3H), 2.89 (s, 2H), 2.72 (s, 3H), 2.32 (s, 2H), 2.22 (s, 6H).

Example 7: The Preparation of N-(2-((2-(dimethylamino)ethyl)(methyl)amino)-4-methoxy-5-(7-(1-methyl-1H-pyrrolo[2,3-b]pyridin-5-yl)pyrrolo[1,2-f][1,2,4]triazin-2-ylamino)phenyl)acrylamide (J-7)

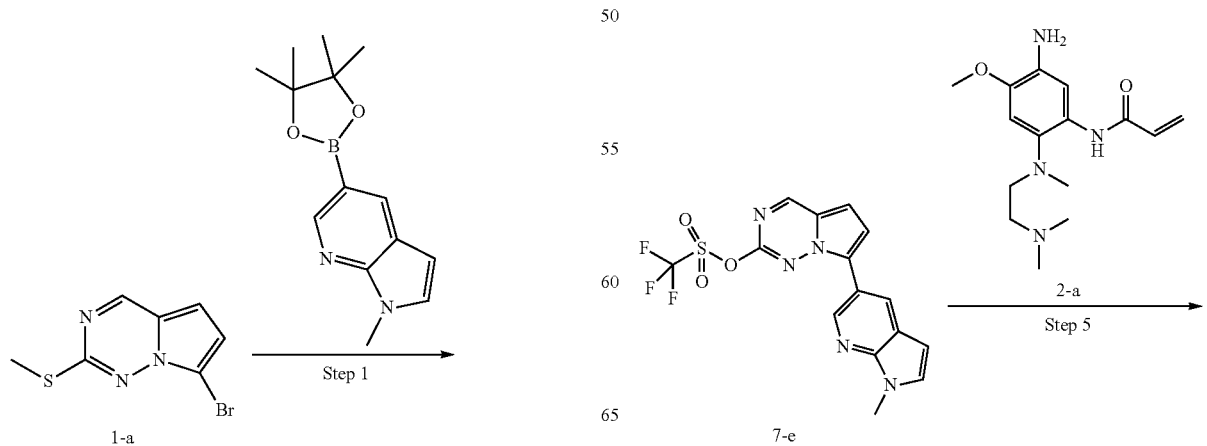

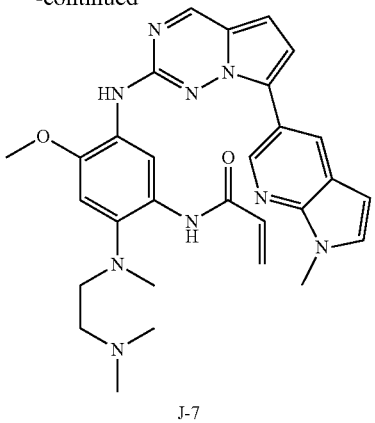

J-7

Step 1: Compound 1-a (250 mg, 1 mmol), 1-methyl-5-(4,4,5,5-tetramethyl-1,3,2-dioxaborolan-2-yl)-1H-pyrrolo[2,3-b]pyridine (387 mg, 1.5 mmol), [1,1'-bis(diphenylphosphino)ferrocene]dichloropalladium(II) (36 g, 0.05 mmol), potassium carbonate (317 mg, 3 mmol) were added to dioxane 50 ml/water 5 ml solution under argon and stirred at 80° C. for 16 h. The reaction was completed and the reaction solution was cooled to room temperature, filtered and extracted with ethyl acetate/water. The combined organic phases were separated, dried over anhydrous sodium sulfate and filtered. The filtrate was concentrated under reduced pressure to give the crude product which was separated and purified by Combi-flash column chromatography to give compound 7-b (232 mg) as a yellow-brown solid which was used directly in the next reaction. Yield: 78.5%; purity: 94.46% (UV254). MS m/z (ESI): 296[M+H]$^+$.

Step 2: Compound 7-b (180 mg, 0.61 mmol) was dissolved in 10 ml of dichloromethane, cooled to 0° C., and m-CPBA (m-chloroperoxybenzoic acid) (421 mg, 2.4 mmol) was added slowly. After the addition, the mixture was stirred at room temperature overnight. The reaction was completed and saturated sodium carbonate solution was added. The organic phase was separated, dried over anhydrous sodium sulfate and filtered. The filtrate was concentrated under reduced pressure to give compound 7-c (80 mg) as a brown solid which was used directly in the next reaction. Yield: 37.2%; purity: 47% (UV254). MS m/z (ESI): 328[M+H]$^+$.

Step 3: Compound 7-c (75 mg, 0.23 mmol) in saturated sodium hydroxide solution (0.65 ml) was stirred at 100° C. for 2 h. The reaction was completed and the mixture was cooled to room temperature, adjusted with acetic acid to pH 4-5, and extracted with dichloromethane, The combined organic phases were separated, dried over anhydrous sodium sulfate and filtered. The filtrate was concentrated under reduced pressure to give compound 7-d (50 mg) as a brown solid which was used directly in the next reaction. Yield: 82%; purity: 62% (UV254). MS m/z (ESI): 266[M+H]$^+$.

Step 4: N-phenyl bis(trifluoromethanesulfonimide) (118 mg, 0.33 mmol) was added to the solution of compound 7-d (80 mg, 0.3 mmol) and N,N-diisopropylethylamine (116 mg, 0.9 mmol) in 5 ml of dimethylformamide at 0° C. and stirred at room temperature for 2 h. The reaction was completed, and the mixture was extracted with dichloromethane and washed with saturated brine. The organic phase was separated, dried over anhydrous sodium sulfate and filtered. The filtrate was concentrated under reduced pressure to give the crude product which was separated and purified by Combi-flash column chromatography [DCM:MeOH=90:10-80:20] to give compound 7-e (25 mg) as a yellow solid which was used directly in the next reaction. Yield: 33%; purity: 94% (UV254). MS m/z (ESI): 398[M+H]$^+$.

Step 5: Tris(dibenzylideneacetone) dipalladium (5 mg, 0.005 mmol) was added to the solution of compound 7-e (20 mg, 0.05 mmol), compound 2-a (15 mg, 0.05 mmol), 4,5-bis(diphenylphosphino)-9,9-dimethylxanthene (6 mg, 0.01 mmol), and cesium carbonate (33 mg. 0.1 mmol) in 3 ml of dioxane and stirred at 160° C. under microwave for 20 minutes. The reaction was completed and the reaction solution was cooled to room temperature and filtered. The filtrate was concentrated under reduced pressure to give the crude product which was separated and purified by preparative liquid chromatography to give compound J-7 (2.01 mg). Purity: 96.92% (UV254). MS m/z (ESI): 540[M+H]$^+$.

Example 8: The Preparation of N-(5(7-cyclopropylpyrrolo[1,2-f][1,2,4]triazin-2-ylamino)-2-((2-(dimethylamino)ethyl)(methyl)amino)-4-methoxyphenyl)acrylamide (J-8)

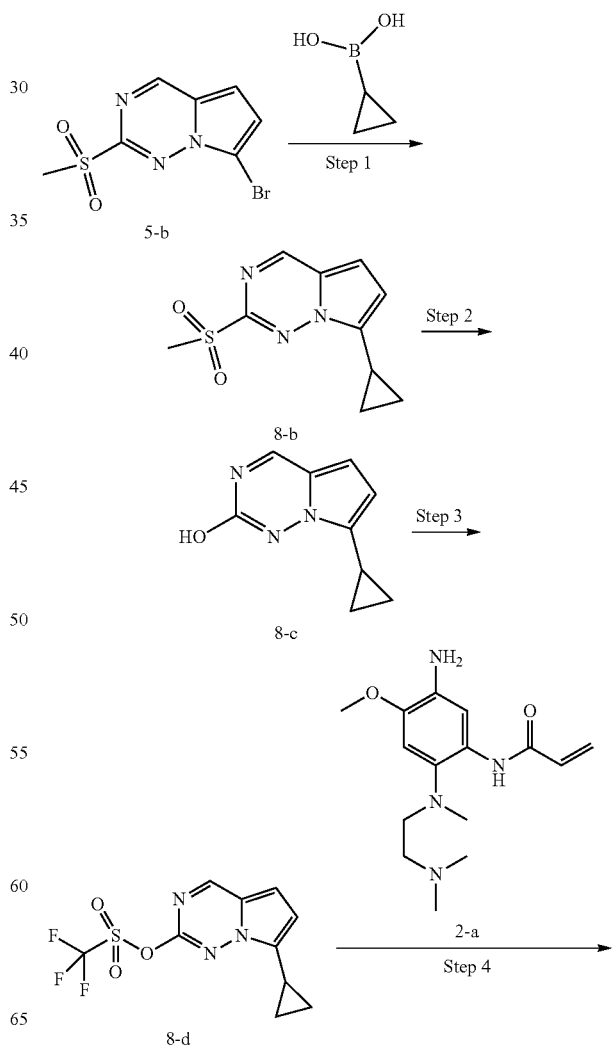

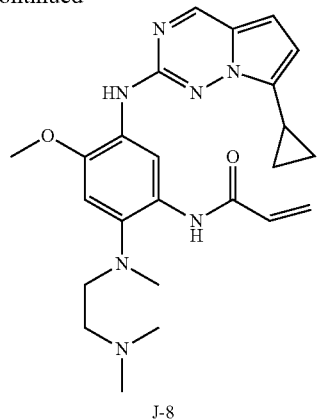

J-8

Step 1: [1,1'-bis(diphenylphosphino)ferrocene]dichloropalladium(II) (37 mg, 0.05 mmol) was added to a mixed solution of compound 5-b (276 mg, 1.0 mmol), cyclopropyl boric acid (258 mg, 3.0 mmol), sodium carbonate (318 mg, 3.0 mmol) in dioxane 15 ml/water 5 ml under argon and stirred under microwave at 110° C. for 5 h. The reaction was completed and the mixture was cooled to room temperature, extracted with dichloromethane/water, and washed with saturated brine. The combined organic phases were separated, dried over anhydrous sodium sulfate and filtered. The filtrate was concentrated under reduced pressure to give the crude product which was separated and purified by Combi-flash column chromatography [PE:EA=50:50-30:70] to give compound 8-b (90 mg) as a yellow solid which was used directly in the next reaction. Yield: 38%; purity: 79% (UV254). MS m/z (ESI): 238.1 [M+H]+.

Step 2: Compound 8-b (160 mg, 0.67 mmol) was added to sodium hydroxide solution (6 N, 1.1 ml, 6.7 mmol) and stirred at 100° C. for 2 h. The reaction was completed and the mixture was cooled to room temperature. Acetic acid was added slowly to adjust pH to 4-5 and the mixture was extracted with dichloromethane and water. The combined organic phases were separated, dried over anhydrous sodium sulfate and filtered. The filtrate was concentrated under reduced pressure to give compound 8-c (117 mg) as a brown solid which was used directly in the next reaction. Yield: 100%; purity: 67% (UV254). MS m/z (ESI): 176[M+H]+.

Step 3: N-phenyl bis(trifluoromethanesulfonimide) (479 mg, 1.34 mmol) was added to the solution of compound 8-c (117 mg, 0.67 mmol) and N,N-diisopropylethylamine (173 mg, 1.34 mmol) in 10 ml of dimethylformamide at 0° C. and stirred at room temperature for 2 h. The reaction was completed and the mixture was concentrated under reduced pressure to give the crude product which was purified by Combi-flash column chromatography [PE:EA=100:0-70:30] to give compound 8-d (180 mg) as a yellow solid which was used directly in the next reaction. Yield: 87.4%; purity: 85% (UV254). MS m/z (ESI): 308.0[M+H]+.

Step 4: Tris(dibenzylideneacetone) dipalladium(27 mg, 0.029 mmol) was added to the solution of compound 8-d (90 mg, 0.29 mmol), compound 2-a (85 mg, 0.29 mmol), 4,5-bis(diphenylphosphino)-9,9-dimethylxanthene (34 mg, 0.058 mmol), and cesium carbonate (190 mg, 0.58 mmol) in 10 ml of dioxane and stirred under microwave at 160° C. for 20 minutes. The reaction was completed and the reaction solution was cooled to room temperature and filtered. The filtrate was concentrated under reduced pressure to give the crude product which was separated and purified by preparative liquid chromatography to give compound J-8 (18.89 mg) as a pale yellow solid. Purity: 100% (UV254). MS m/z (ESI): 450.3[M+H]+. 1H NMR (400 MHz, DMSO) δ 10.08 (s, 1H), 9.48 (s, 1H), 8.76 (s, 1H), 8.26 (s, 1H), 7.51 (s, 1H), 7.00 (s, 1H), 6.76-6.75 (d, J=4.6 Hz, 1H), 6.40-6.39 (d, J=4.6 Hz, 2H), 6.18-6.13 (dd, J1=1.7 Hz, J2=16.8 Hz, 1H), 5.72-5.69 (t, J=9.9 Hz, 1H), 3.89 (s, 3H), 2.89-2.86 (t, J=4.5 Hz, 3H), 2.68 (s, 3H), 2.32 (s, 2H), 2.21 (s, 6H), 1.08-1.06 (dd, J1=2.0 Hz, J2=8.3 Hz, 2H), 0.80 (s, 2H).

Example 9: The Preparation of N-(2-((2-(dimethylamino)ethyl)(methyl)amino)-4-methoxy-5-(7-methylpyrrolo[1,2-f][1,2,4]triazin-2-ylamino)phenyl) acrylamide (J-9)

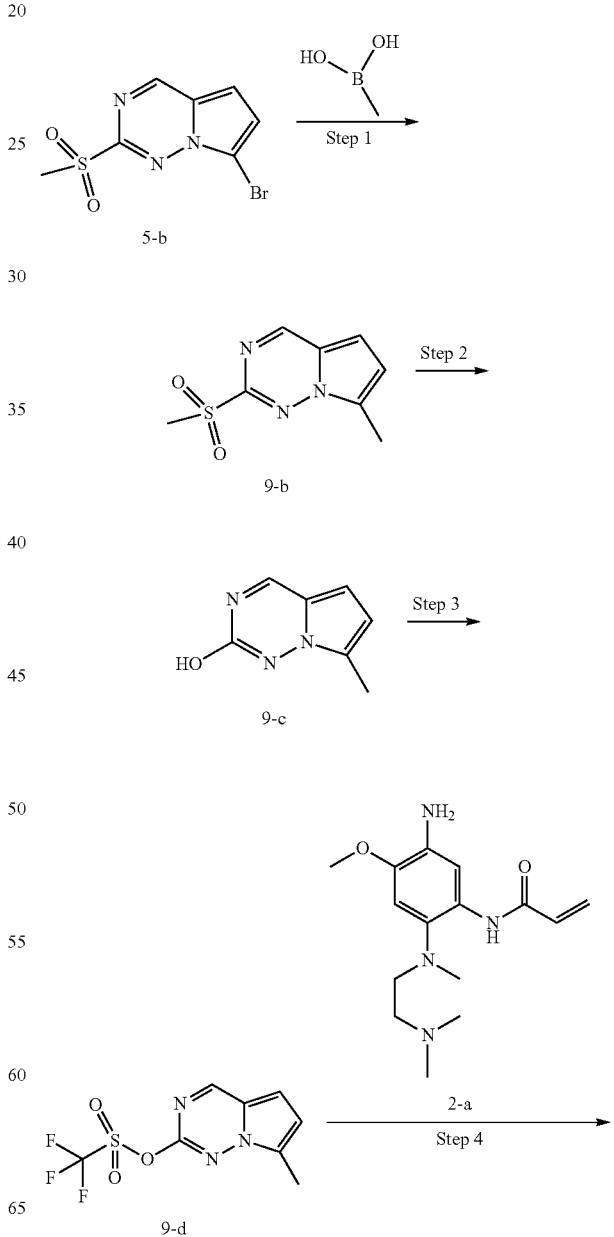

-continued

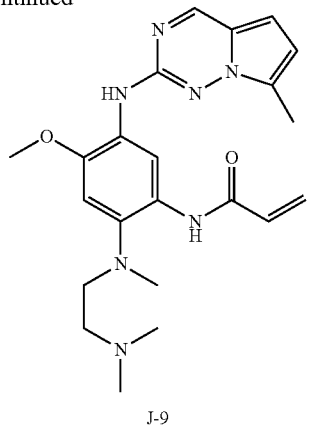

J-9 to give the crude product which was separated and purified by preparative liquid chromatography to give compound J-9 (33 mg) as a yellow solid. Yield: 24.4%, purity: 96.82% (UV254). MS m/z (ESI): 424.2[M+H]$^+$. $^1$H NMR (400 MHz, DMSO) δ 10.07 (s, 1H), 9.38 (s, 1H), 8.80 (s, 1H), 7.53 (s, 1H), 7.01 (s, 1H), 6.80-6.79 (d, J=4.4 Hz, 1H), 6.62-6.61 (d, J=4.4 Hz, 1H), 6.42-6.36 dd, J1=10.0 Hz, J2=16.9 Hz, 1H), 6.25-6.20 (dd, J1=2.1 Hz, J2=16.9 Hz, 1H), 5.75-5.72 (dd, J1=1.8 Hz, J2=10.1 Hz, 1H), 3.88 (s, 3H), 2.87-2.86 (d, J=5.3 Hz, 2H), 2.68 (s, 3H), 2.57 s, 3H), 2.30 (s, 2H), 2.21 (s, 6H).

Example 10: The Preparation of N-(2-((2-(dimethylamino)ethyl)(methyl)amino)-4-methoxy-5-(7-(quinolin-3-yl)pyrrolo[1,2-f][1,2,4]triazin-2-ylamino)phenyl)acrylamide (J-10)

Step 1: [1,1'-bis(diphenylphosphino)ferrocene]dichloropalladium(II) (110 mg, 0.15 mmol) was added to a mixed solution of compound 5-b (828 mg, 3.0 mmol), methyl boric acid (539 mg, 9.0 mmol) and sodium carbonate (795 mg, 7.5 mmol) in dioxane 30 ml/water 10 ml and stirred under microwave at 110° C. for 6 h. The reaction was completed and the mixture was cooled to room temperature and extracted with dichloromethane/water. The combined organic phases were separated, dried over anhydrous sodium sulfate and filtered. The filtrate was concentrated under reduced pressure to give the crude product which was separated and purified by Combi-flash column chromatography [PE:EA=80:20-60:40] to give compound 9-b (242 mg) as a brown solid which was used directly in the next reaction. Yield: 38.2%; purity: 65% (UV254). MS m/z (ESI): 212.1 [M+H]$^+$.

Step 2: Compound 9-b (242 mg, 1.14 mmol) was added to sodium hydroxide solution (6N, 2 ml, 11.4 mmol) and stirred at 100° C. for 2 h. The reaction was completed and the mixture was cooled to room temperature. Acetic acid was added slowly to adjust pH to 3-4 and the mixture was extracted with dichloromethane and water. The combined organic phases were separated, dried over anhydrous sodium sulfate and filtered. The filtrate was concentrated under reduced pressure to give compound 9-c (137 mg) as a brown solid which was used directly in the next reaction. Yield: 80.6%; purity: 89% (UV254). MS m/z (ESI): 150.1 [M+H]$^+$.

Step 3: N-phenyl bis(trifluoromethanesulfonimide) (656 mg, 1.84 mmol) was added in batches to the solution of compound 9-c (137 mg, 0.92 mmol) and N,N-diisopropylethylamine (357 mg, 2.76 mmol) in 10 ml of dimethylformamide and stirred at room temperature for 2 h. The reaction was completed and the mixture was concentrated under reduced pressure to give the crude product which was purified by Combi-flash column chromatography [PE:EA=100:0-80:20] to give compound 9-d (180 mg) as a yellow oil which was used directly in the next reaction. Yield: 70%; purity: 73% (UV254). MS m/z (ESI): 280.0 [M+H]$^+$.

Step 4: Tris(dibenzylideneacetone) dipalladium (29 mg, 0.032 mmol) was added to the solution of compound 9-d (90 mg, 0.32 mmol), compound 2-a (93 mg, 0.32 mmol), 4,5-bis(diphenylphosphino)-9,9-dimethylxanthene (37 mg, 0.064 mmol), and cesium carbonate (209 mg, 0.64 mmol) in 8 ml of dioxane under argon and stirred under microwave at 170° C. for 15 minutes. The reaction was completed and the reaction solution was cooled to room temperature and filtered. The filtrate was concentrated under reduced pressure

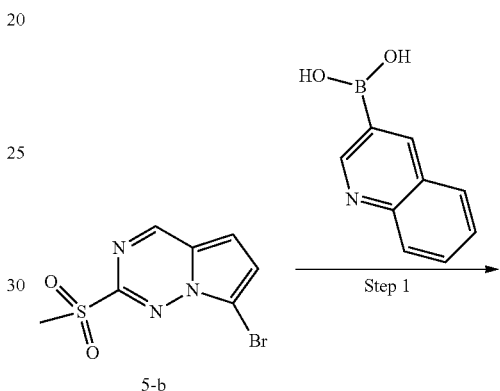

5-b

Step 1

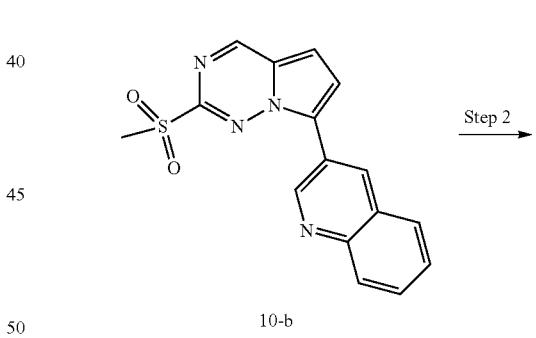

10-b

Step 2

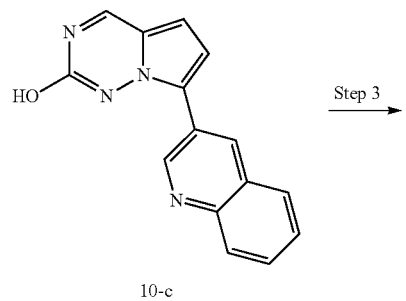

10-c

Step 3

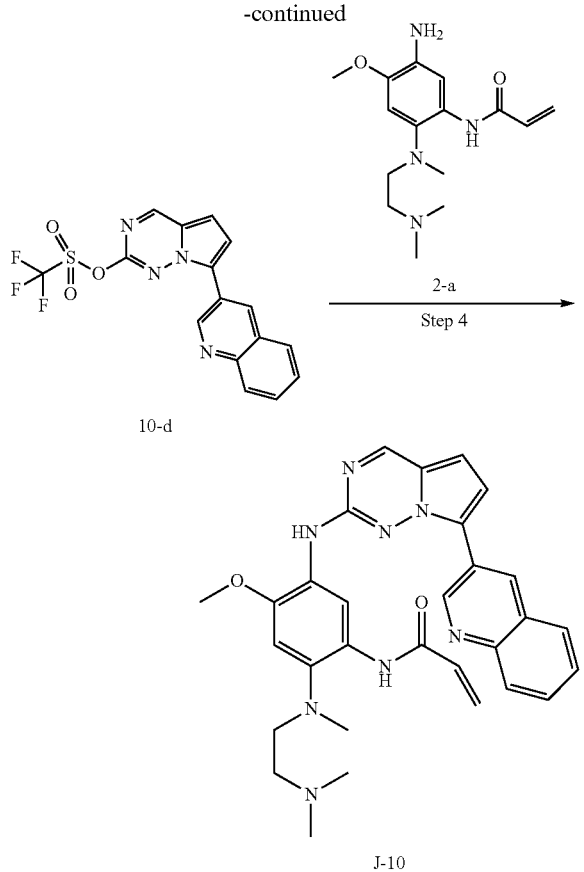

Step 1: [1,1'-bis(diphenylphosphino)ferrocene]dichloropalladium(II) (110 mg, 0.15 mmol) was added to a mixed solution of compound 5-b (828 mg, 3.0 mmol), quinolin-3-yl boric acid (571 mg, 3.3 mmol) and sodium carbonate (795 mg, 7.5 mmol) in dioxane 30 ml/water 10 ml and stirred under microwave at 100° C. overnight. The reaction was completed and the mixture was cooled to room temperature, and extracted with dichloromethane/water. The combined organic phases were separated, dried over anhydrous sodium sulfate and filtered. The filtrate was concentrated under reduced pressure to give the crude product which was separated and purified by Combi-flash column chromatography [PE:EA=100:0-20:80] to give compound 10-b (226 mg) as a yellow solid which was used directly in the next reaction. Yield: 23%; purity: 49% (UV254). MS m/z (ESI): 325.1 [M+H]$^+$.

Step 2: Compound 10-b (226 mg, 0.7 mmol) was added to sodium hydroxide solution (3N, 2.3 ml, 7 mmol) and stirred at 100° C. for 2 h. The reaction was completed and the mixture was cooled to room temperature. pH was adjusted to 4-5 and the mixture was extracted with dichloromethane and water. The combined organic phases were separated, dried over anhydrous sodium sulfate and filtered. The filtrate was concentrated under reduced pressure to give compound 10-c (180 mg) as a brown solid which was used directly in the next reaction. Yield: 98%; purity: 87% (UV254). MS m/z (ESI): 263.1 [M+H]$^+$.

Step 3: N-phenyl bis(trifluoromethanesulfonimide) (493 mg, 1.38 mmol) was added in batches to the solution of compound 10-c (180 mg, 0.69 mmol) and N,N-diisopropylethylamine (267 mg, 2.07 mmol) in 10 ml of dimethylformamide at 0° C. and stirred at room temperature for 2 h. The reaction was completed and the mixture was concentrated under reduced pressure to give the crude product which was purified by Combi-flash column chromatography [PE:EA=100:0-80:20] to give compound 10-d (120 mg) as a yellow solid which was used directly in the next reaction. Yield: 44.3%; purity: 90% (UV254). MS m/z (ESI): 395.1 [M+H]$^+$.

Step 4: Tris(dibenzylideneacetone) dipalladium(14 mg, 0.015 mmol) was added to the solution of compound 10-d (60 mg, 0.15 mmol), compound 2-a (44 mg, 0.15 mmol), 4,5-bis(diphenylphosphino)-9,9-dimethylxanthene (18 mg, 0.03 mmol), and cesium carbonate (98 mg, 0.3 mmol) in 8 ml of dioxane and stirred under microwave at 170° C. for 15 minutes. The reaction was completed and the reaction solution was cooled to room temperature and filtered. The filtrate was concentrated under reduced pressure to give the crude product which was separated and purified by preparative liquid chromatography to give compound J-10 (18 mg) as a yellow solid. Yield: 22.5%, purity: 97.08% (UV254). MS m/z (ESI): 537.3[M+H]$^+$. $^1$H NMR (400 MHz, DMSO) δ 10.15 (s, 1H), 9.48 (d, J=2.2 Hz, 1H), 9.23 (d, J=1.9 Hz, 1H), 9.03 (s, 1H), 8.64 (s, 1H), 8.36 (s, 1H), 7.96-7.94 (d, J=8.3 Hz, 1H), 7.71-7.66 (m, 2H), 7.55-7.50 (m, 2H), 7.12 (s, 1H), 7.02-7.01 (d, J=4.8 Hz, 1H), 6.30-6.26 (dd, J1=10.7 Hz, J2=17.0 Hz, 1H), 5.95-5.90 (dd, J1=5.8 Hz, J2=16.9 Hz, 1H), 5.58-5.55 (dd, J1=1.7 Hz, J2=10.1 Hz, 1H), 3.80 (s, 3H), 2.96-2.93 (d, J=9.5 Hz, 2H), 2.78 (s, 3H), 2.37 (s, 2H), 2.24 (s, 6H).

Example 11: The Preparation of N-(2-((2-(dimethylamino)ethyl)(methyl)amino)-4-methoxy-5-(7-phenylpyrrolo[1,2-f][1,2,4]triazin-2-ylamino)phenyl) acrylamide (J-11)

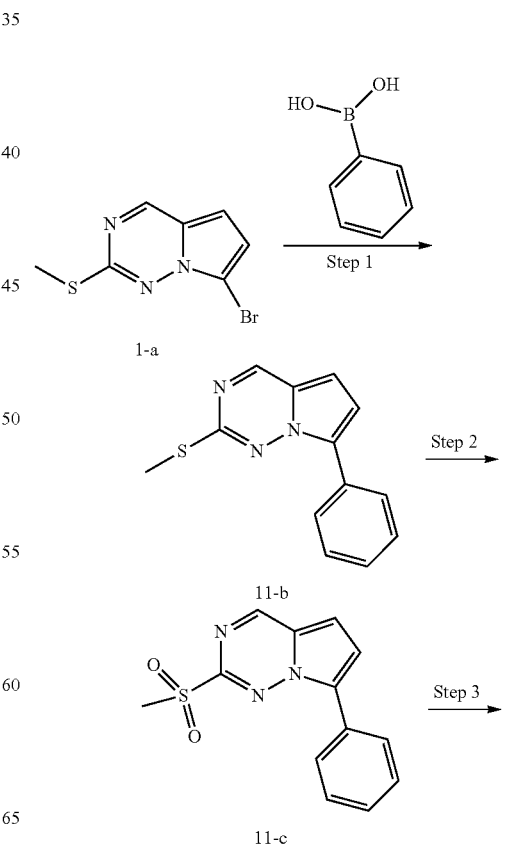

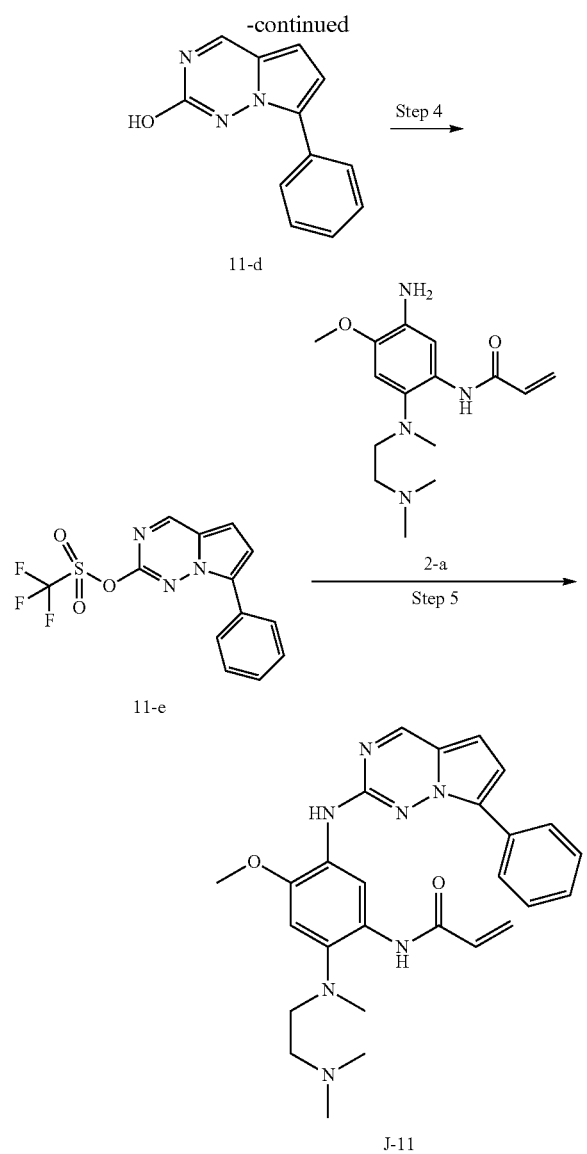

(180 mg) as a yellow solid which was used directly in the next reaction. Purity: 54% (UV254). MS m/z (ESI): 274.1 [M+H]+.

Step 3: Compound 11-c (180 mg, 0.66 mmol) was added to the solution of sodium hydroxide (396 mg, 10 mmol) in 10 ml of water and stirred at 100° C. for 2 h. The reaction was completed and the mixture was cooled to room temperature, neutralized with acedic acid and extracted with ethyl acetate/water. The organic phase was separated, collected and concentrated under reduced pressure to give compound 11-d (100 mg) as a yellow powder which was used directly in the next reaction. Purity: 66% (UV254). MS m/z (ESI): 212.1 [M+H]+.

Step 4: N,N-diisopropylethylamine (183 mg, 1.42 mmol) was added to the solution of compound 11-d (100 mg, 0.47 mmol) in 5 ml of dimethylformamide at 0° C. and stirred at room temperature for 5 minutes. N-phenyl bis(trifluoromethanesulfonimide) (169 mg, 0.47 mmol) was added and stirred at room temperature for 3 h. The reaction was completed and the mixture was extracted with ethyl acetate/water. The organic phase was separated, collected, and washed with water and saturated brine. The organic phase was separated and concentrated under reduced pressure to give the crude product which was purified by Combi-flash column chromatography [PE:EA=90:10] to give compound 11-e (55 mg) as a yellow semi-solid which was used directly in the next reaction. Purity: 90% (UV254). MS m/z (ESI): 344.0[M+H]+.

Step 5: Tris(dibenzylideneacetone) dipalladium (3 mg, 0.003 mmol), 4,5-bis(diphenylphosphino)-9,9-dimethylxanthene (4 mg, 0.006 mmol) and cesium carbonate (19 mg, 0.058 mmol) were added to the solution of compound 11-e (10 mg, 0.029 mmol) and compound 2-a (9 mg, 0.029 mmol) in 2 ml of dioxane and stirred under microwave at 160° C. for 10 minutes. The reaction was completed and the reaction solution was cooled to room temperature and filtered. The filtrate was concentrated under reduced pressure to give the crude product which was separated and purified by preparative liquid chromatography to give compound J-11 (2.08 mg). Purity: 100% (UV254). MS m/z (ESI): 486.1 [M+H]+. 1H NMR (400 MHz, DMSO) δ 9.94 (s, 1H), 8.97 (s, 1H), 8.47 (s, 1H), 8.14 (d, J=7.8 Hz, 2H), 7.92 (s, 1H), 7.39 (t, J=7.6 Hz, 2H), 7.27 (d, J=7.3 Hz, 1H), 7.20 (d, J=4.8 Hz, 1H), 7.01-6.96 (m, 2H), 6.27 (d, J=16.7 Hz, 1H), 5.80 (d, J=10.3 Hz, 1H), 5.33 (t, J=4.9 Hz, 1H), 3.89 (s, 3H), 3.20 (s, 2H), 2.65 (s, 3H), 2.60 (s, 2H), 1.25 (s, 6H).

Example 12: The Preparation of N-(2-((2-(dimethylamino)ethyl)(methyl)amino)-4-methoxy-5-(7-(1-methyl-1H-pyrrol-3-yl)pyrrolo[1,2-f][1,2,4]triazin-2-ylamino)phenyl)acrylamide (J-12)

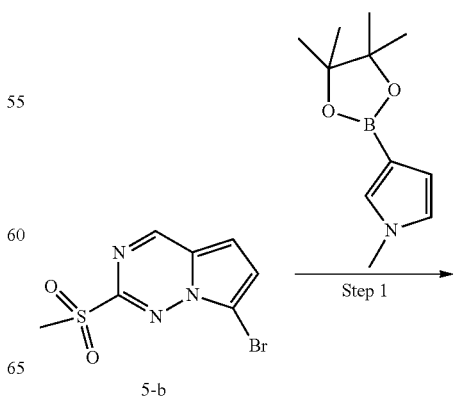

Step 1: Phenylboronic acid (250 mg, 2.05 mmol), [1,1'-bis(diphenylphosphino)ferrocene]dichloropalladium(II) (150 mg, 0.2 mmol), and sodium carbonate (435 mg, 4.10 mmol) were added to the solution of compound 1-a (500 mg, 2.05 mmol) in acetonitrile 15 ml/water 3 ml and stirred under microwave at 100° C. for 20 minutes. The reaction was completed and the reaction solution was cooled to room temperature and filtered. The filtrate was concentrated under reduced pressure to give the crude product which was separated and purified by Combi-flash column chromatography [PE:EA=100:0-80:20] to give compound 11-b (210 mg) as a yellow solid which was used directly in the next reaction. Yield: 42%; purity: 76% (UV254). MS m/z (EST): 242.1 [M+H]+.

Step 2: Compound 11-b (200 mg, 0.83 mmol) in 100 ml of dichloromethane was cooled to 0° C. and m-CPBA (m-chloroperoxybenzoic acid) (428 mg, 2.49 mmol) was added slowly. After the addition, the mixture was stirred at room temperature for 3 h. The reaction was completed and saturated sodium thiosulfate solution was added. The organic phase was separated and washed with saturated sodium carbonate. The organic phase was separated and concentrated under reduced pressure to give compound 11-c

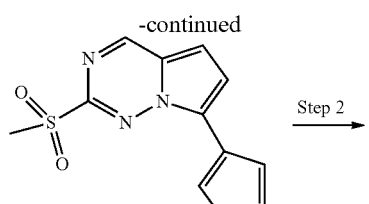

12-b

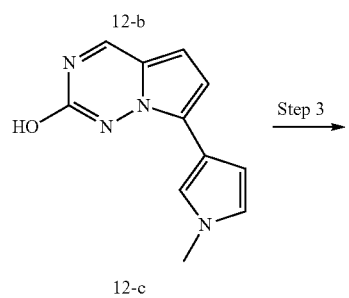

12-c

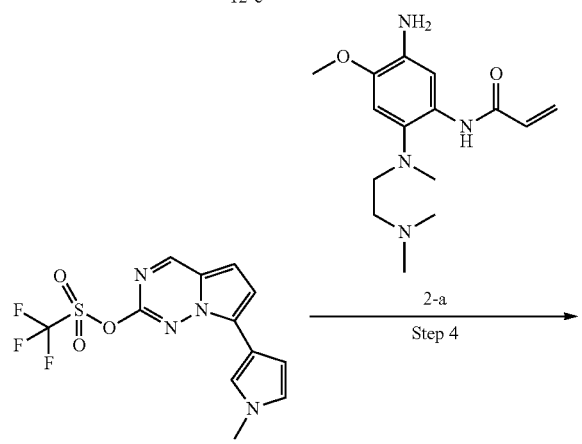

12-d

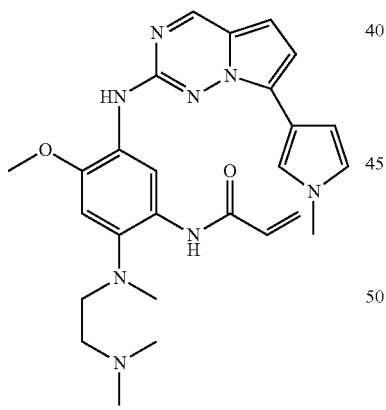

J-12 chromatography to give compound 12-b (80 mg) as a yellow powder which was used directly in the next reaction. Yield: 32%. MS m/z (ESI): 277.1 [M+H]$^+$.

Step 2: Compound 12-b (80 mg, 0.29 mmol) was added to the solution of sodium hydroxide (174 mg, 4.34 mmol) in 3 ml of water and stirred at 100° C. for 2 h. The reaction was completed and the mixture was cooled to room temperature. Acetic acid was added slowly to adjust pH to 4 and the mixture was extracted with ethyl acetate. The combined organic phases were separated and concentrated under reduced pressure to give compound 12-c (80 mg) as yellow oil which was used directly in the next reaction. MS m/z (ESI): 215.1 [M+H]$^+$.

Step 3: N,N-diisopropylethylamine (145 mg, 1.12 mmol) and N-phenyl bis(trifluoromethanesulfonimide) (134 mg, 0.37 mmol) were added to the solution of compound 12-c (80 mg, 0.37 mmol) in 4 ml of dimethylformamide at 0° C. and stirred at room temperature for 3 h. The reaction was completed and the mixture was concentrated under reduced pressure to give the crude product which was purified by Combi-flash column chromatography to give compound 12-d (40 mg) as yellow oil which was used directly in the next reaction. MS m/z (ESI): 347.1 [M+H]$^+$.

Step 4: Compound 2-a (25 mg, 0.09 mmol), tris(dibenzylideneacetone) dipalladium (8 mg, 0.009 mmol), 4,5-bis(diphenylphosphino)-9,9-dimethylxanthene (10 mg, 0.018 mmol) and cesium carbonate (58 mg, 0.18 mmol) were added to the solution of compound 12-d (30 mg, 0.09 mmol) in 2 ml of dioxane and stirred under microwave at 160° C. for 10 minutes. The reaction was completed and the reaction solution was cooled to room temperature and filtered. The filtrate was concentrated under reduced pressure to give the crude product which was separated and purified by preparative liquid chromatography to give compound J-12 (1.83 mg) as a yellow powder. MS m/z (ESI): 489.2[M+H]$^+$.

Example 13: The Preparation of N-(2-(4-(dimethylamino)piperidin-1-yl)-4-methoxy-5-(7-(quinolin-3-yl)pyrrolo[1,2-f][1,2,4]triazin-2-ylamino)phenyl) acrylamide (J-13)

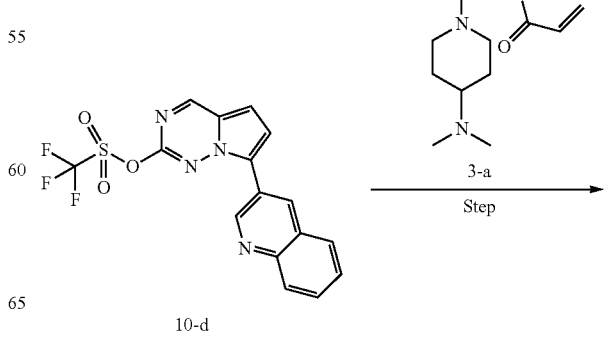

10-d

Step 1: 1-methyl-1H-pyrrol-3-yl boric acid (188 mg, 0.9 mmol), [1,1'-bis(diphenylphosphino)ferrocene]dichloropalladium(II) (67 mg, 0.09 mmol), sodium carbonate (192 mg, 1.81 mmol) and 2 ml of water were added to the solution of compound 5-b (250 mg, 0.9 mmol) in 16 mL of acetonitrile and stirred under microwave at 130° C. for 30 minutes. The reaction was completed and the reaction solution was cooled to room temperature and filtered. The filtrate was concentrated under reduced pressure to give the crude product which was separated and purified by Combi-flash column

63

-continued

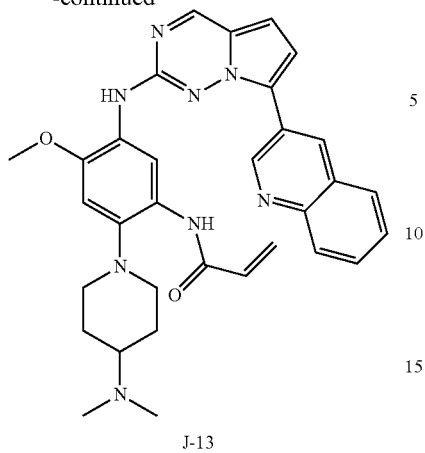

J-13

Step: Tris(dibenzylideneacetone) dipalladium (14 mg, 0.015 mmol) was added to the solution of compound 10-d (60 mg, 0.15 mmol), compound 3-a (48 mg, 0.15 mmol), 4,5-bis(diphenylphosphino)-9,9-dimethylxanthene (18 mg, 0.03 mmol), and cesium carbonate (98 mg, 0.3 mmol) in 8 ml of dioxane and stirred under microwave at 170° C. for 15 minutes. The reaction was completed, and the mixture was cooled to room temperature and concentrated under reduced pressure to give the crude product which was separated and purified by preparative liquid chromatography to give compound J-13 (16 mg) as a yellow solid. Yield: 19%, purity: 97.38% (UV254). MS m/z (ESI): 563.3 [M+H]$^+$. $^1$H NMR (400 MHz, DMSO) δ 9.47 (s, 1H), 9.23-9.22 (d, J=2.0 Hz, 1H), 9.02 (s, 2H), 8.37 (s, 1H), 8.30 (s, 1H), 7.98-7.96 (d, J=8.4 Hz, 1H), 7.74-7.66 (m, 2H), 7.55-7.54 (d, J=5.0 Hz, 2H), 7.01-7.00 (d, J=4.8 Hz, 1H), 6.96 (s, 1H), 6.61-6.54 (dd, J1=10.2 Hz, J2=16.9 Hz, 1H), 5.98-5.94 (dd, J1=1.7 Hz, J2=16.9 Hz, 1H), 5.58-5.55 (d, J=11.7 Hz, 1H), 3.78 (s, 3H), 3.13-3.11 (d, J=11.2 Hz, 2H), 2.77-2.71 (t, J=11.2 Hz, 1H), 2.25 (s, 7H), 1.90-1.87 (d, J=10.6 Hz, 2H), 1.76-1.74 (d, J=9.8 Hz, 2H).

Example 14: The Preparation of N-(2-(4-(dimethylamino)piperidin-1-yl)-4-methoxy-5-(7-methylpyrrolo[1,2-f][1,2,4]triazin-2-yl amino)phenyl)acrylamide (J-14)

64

-continued

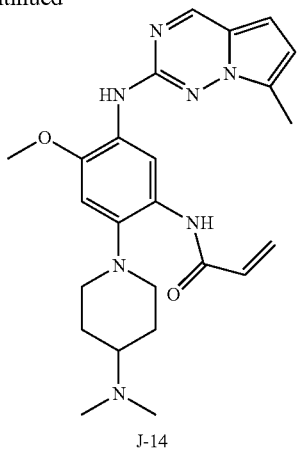

J-14

Step: Tris(dibenzylideneacetone) dipalladium (29 mg, 0.032 mmol) was added to the solution of compound 9-d (90 mg, 0.32 mmol), compound 3-a (102 mg, 0.32 mmol), 4,5-bis(diphenylphosphino)-9,9-dimethylxanthene (37 mg, 0.064 mmol), and cesium carbonate (209 mg, 0.64 mmol) in 8 ml of dioxane under argon and stirred under microwave at 170° C. for 15 minutes. The reaction was completed and the reaction solution was cooled to room temperature and filtered. The filtrate was concentrated under reduced pressure to give the crude product which was separated and purified by preparative liquid chromatography to give compound J-14 (31 mg) as a yellow solid. Yield: 21.5%, purity: 100% (UV254). MS m/z (ESI): 450.4[M+H]$^+$. $^1$H NMR (400 MHz, DMSO) δ 9.10 (s, 1H), 8.95 (s, 1H), 8.79 (s, 1H), 7.52 (s, 1H), 6.86 (s, 1H), 6.79-6.78 (d, J=4.5 Hz, 1H), 6.68-6.61 (dd, J1=10.1 Hz. J2=16.8 Hz, 1H), 6.61-6.60 (d, J=4.5 Hz, 1H), 6.24-6.19 (dd, J1=1.8 Hz, J2=16.9 Hz, 1H), 5.74-5.71 (dd, J1=1.6 Hz, J2=10.2 Hz, 1H), 3.88 (s, 3H), 3.01-2.99 (d, J=11.6 Hz, 2H), 2.69-2.64 (m, 2H), 2.52 (s, 3H), 2.22 (s, 6H), 2.18 (m, 1H), 1.85-1.82 (d, J=10.9 Hz, 2H), 1.71-1.66 (t, J=11.2 Hz, 2H).

Example 15: The Preparation of N-(5(7-cyclopropylpyrrolo[1,2-f][1,2,4]triazin-2-ylamino)-2-(4-(dimethylamino)piperidin-1-yl)-4-methoxyphenyl)acrylamide (J-15)

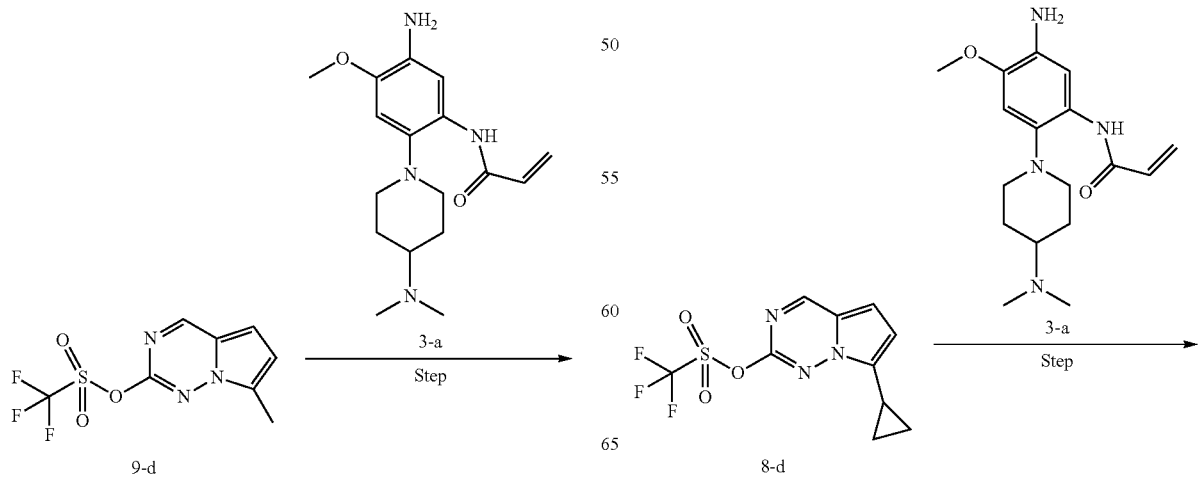

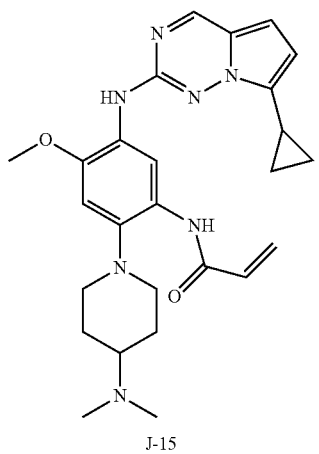

J-15

Step: Tris(dibenzylideneacetone) dipalladium (27 mg, 0.029 mmol) was added to the solution of compound 8-d (90 mg, 0.29 mmol), compound 3-a (93 mg, 0.29 mmol), 4,5-bis(diphenylphosphino)-9,9-dimethylxanthene (34 mg, 0.058 mmol) and cesium carbonate (190 mg, 0.58 mmol) in 10 ml of dioxane and stirred under microwave at 170° C. for 15 minutes. The reaction was completed and the reaction solution was cooled to room temperature and filtered. The filtrate was concentrated under reduced pressure to give the crude product which was separated and purified by preparative liquid chromatography to give compound J-15 (14.6 mg) as a yellow solid. Yield: 10.6%, purity: 100% (UV254). MS m/z (ESI): 476.1 [M+H]$^+$. $^1$H NMR (400 MHz, DMSO) δ 9.18 (s, 1H), 8.95 (s, 1H), 8.75 (s, 1H), 7.49 (s, 1H), 6.84 (s, 1H), 6.75-6.74 (d, J=4.6 Hz, 1H), 6.68-6.61 (dd, J1=10.1 Hz, J2=16.7 Hz, 1H), 6.40-6.39 (d, J=4.6 Hz, 1H), 6.18-6.13 (dd, J1=2.0 Hz, J2=16.9 Hz, 1H), 5.71-5.68 (dd, J1=1.8 Hz, J2=10.1 Hz, 1H), 3.89 (s, 3H), 3.02-3.00 (d, J=11.5 Hz, 2H), 2.74 (s, 1H), 2.68-2.63 (t, J=10.1 Hz, 2H), 2.21 (s, 6H), 1.95 (m, 1H), 1.84-1.81 (d, J=10.6 Hz, 2H), 1.71-1.63 (dd, J1=11.5 Hz, J2=20.3 Hz, 2H), 1.05-1.02 (m, 2H), 0.80-0.78 (m, 2H).

Example 16: The Preparation N-(2-((2-(dimethylamino)ethyl)(methyl)amino)-4-methoxy-5-(3(1-methyl-1H-pyrrol-3-yl)imidazo[1,2-a]pyrazin-6-ylamino)phenyl)acrylamide (J-16)

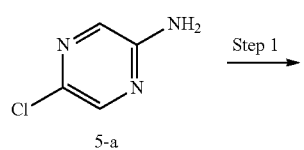

5-a

Step 1 →

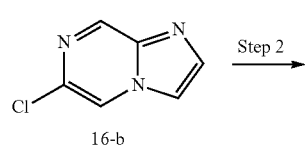

16-b

Step 2 →

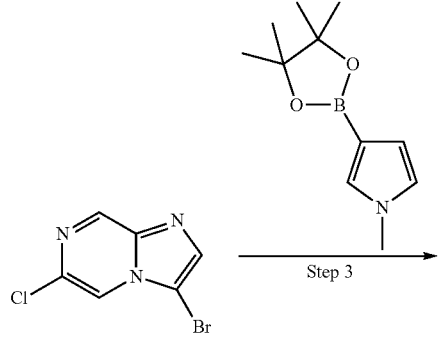

16-c

Step 3 →

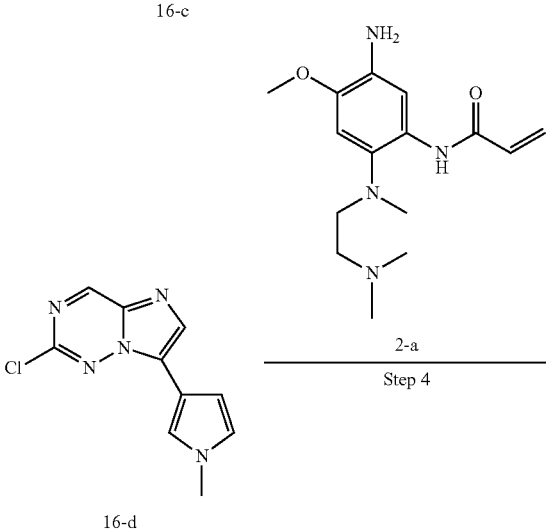

16-d

Step 4 →

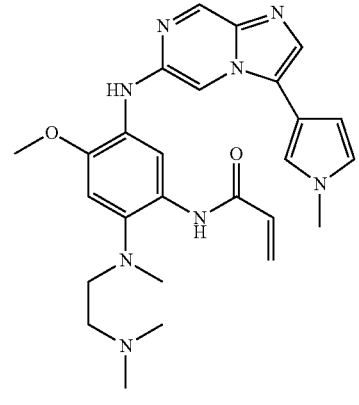

J-16

Step 1: Compound 5-a (2.6 g, 20 mmol) and 2-bromo-1,1-diethoxyethane (12.0 g, 60.89 mmol) were dissolved in 30 ml of isopropanol solution and hydrogen bromide solution (10.5 g, 62.22 mmol) was added and stirred at 80° C. overnight. The reaction was completed and the mixture was cooled to room temperature, adjusted with sodium bicarbonate to pH 8, and extracted with dichloromethane. The combined organic phases were separated and concentrated under reduced pressure to give the crude product which was purified by Combi-flash column chromatography [DCM:MeOH=90:10-70:30] to give compound 16-b (2.3 g) as a brown solid which was used directly in the next reaction. Yield: 49.75%, purity: 96.63. MS m/z (ESI): 154.0[M+H]$^+$.

Step 2: N-bromosuccinimide (1.46 g, 8.2 mmol) was added to the solution of compound 16-b (1.2 g, 7.8 mmol)

in 40 ml of acetonitrile and stirred at room temperature for 2 h. The reaction was completed and the mixture was extracted with ethyl acetate and water. The combined organic phases were separated, dried over anhydrous sodium sulfate and filtered. The filtrate was concentrated under reduced pressure to give the crude product which was separated and purified by Combi-flash column chromatography [PE:EA=100:0-70:30] to give compound 16-c (850 mg) which was used directly in the next reaction. Yield: 47.2%, purity: 100%. MS m/z (ESI): 231.9 [M+H]$^+$.

Step 3: [1,1'-bis(diphenylphosphino)ferrocene]dichloropalladium(II) (27 mg, 0.0375 mmol) was added to the solution of compound 16-c (174 mg, 0.75 mmol), 1-methyl-1H-pyrrol-3-yl boric acid (147 mg, 0.71 mmol) and sodium carbonate (238 mg, 2.25 mmol) in acetonitrile 15 ml/water 3 ml under argon and stirred at 70° C. for 4 h. The reaction was completed, and the mixture was cooled to room temperature and extracted with ethyl acetate and water. The combined organic phases were separated and filtered. The filtrate was concentrated under reduced pressure to give the crude product which was separated and purified by Combi-flash column chromatography [PE:EA=60:40-40:60] to give compound 16-d (81 mg) which was used directly in the next reaction. Yield: 46.5%, purity: 100%. MS m/z (ESI): 233 [M+H]$^+$.

Step 4: Tris(dibenzylideneacetone) dipalladium (27 mg, 0.03 mmol) was added to the solution of compound 16-d (69 mg, 0.3 mmol), compound 2-a (88 mg, 0.3 mmol), 4,5-bis(diphenylphosphino)-9,9-dimethylxanthene (35 mg, 0.06 mmol), and cesium carbonate (196 mg, 0.6 mmol) in 10 ml of dioxane under argon and stirred under microwave at 170° C. for 25 minutes. The reaction was completed, and the mixture was cooled to room temperature and concentrated under reduced pressure to give the crude product which was separated and purified by preparative liquid chromatography to give compound J-16 (34.7 mg). Yield: 23.3%, purity: 100%. MS m/z (ESI): 489[M+H]$^+$. $^1$H NMR (400 MHz, DMSO) δ 10.20 (s, 1H), 8.81 (d, J=1.3 Hz, 1H), 8.52 (s, 1H), 8.12 (s, 1H), 7.81 (s, 1H), 7.52 (s, 1H), 7.39 (s, 1H), 7.00 (s, 1H), 6.90-6.89 (t, J=2.3 Hz, 1H), 6.50-6.49 (t, J=2.2 Hz, 1H), 6.39-6.32 (dd, J1=9.9 Hz, J2=16.8 Hz, 1H), 6.23-6.19 (dd, J1=1.9 Hz, J2=16.8 Hz, 1H), 5.75-5.72 (dd, J1=1.9 Hz, J2=10.0 Hz, 1H), 3.84 (s, 3H), 3.69 (s, 3H), 2.86-2.83 (t, J=5.3 Hz, 2H), 2.68 (s, 3H), 2.27-2.24 (t, J=5.6 Hz, 2H), 2.19 (s, 6H).

Example 17: The Preparation of N-(2-((2-(dimethylamino)ethyl)(methyl)amino)-4-methoxy-5-(3(pyridin-3-yl)imidazo[1,2-a]pyrazin-6-ylamino)phenyl) acrylamide (J-17)

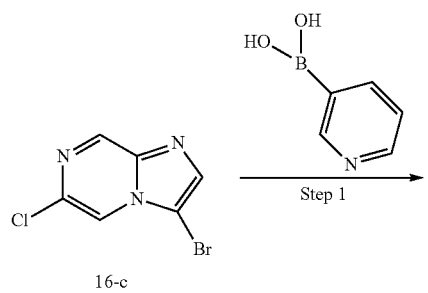

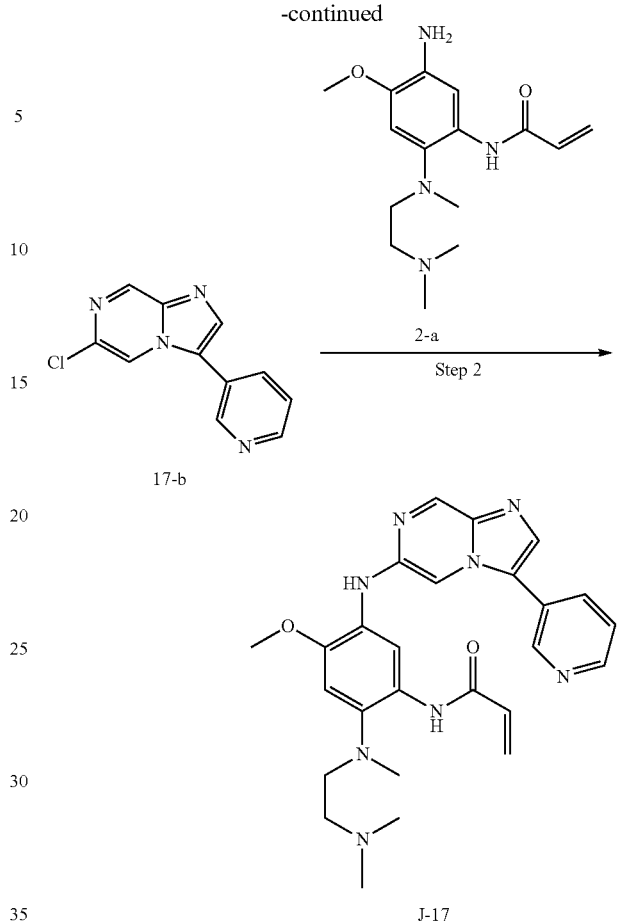

Step 1: [1,1'-bis(diphenylphosphino)ferrocene]dichloropalladium(II) (27 mg, 0.0375 mmol) was added to the solution of compound 16-c (174 mg, 0.75 mmol), pyridin-3-yl boric acid (87 mg, 0.71 mmol) and sodium carbonate (238 mg, 2.25 mmol) in acetonitrile 8 ml/water 2 ml under argon and stirred at 70° C. for 4 h. The reaction was completed, and the mixture was cooled to room temperature and extracted with ethyl acetate and water. The combined organic phases were separated and washed with saturated brine. The organic phase was separated, dried over anhydrous sodium sulfate and filtered. The filtrate was concentrated under reduced pressure to give the crude product which was separated and purified by Combi-flash column chromatography [PE:EA=50:50-20:80] to give compound 17-b (87 mg) which was used directly in the next reaction. Yield: 50.6%, purity: 93%. MS m/z (ESI): 231[M+H]$^+$.

Step 2: Tris(dibenzylideneacetone) dipalladium (30 mg, 0.0325 mmol) was added to the solution of compound 17-b (75 mg, 0.325 mmol), compound 2-a (95 mg, 0.325 mmol), 4,5-bis(diphenylphosphino)-9,9-dimethylxanthene (38 mg, 0.065 mmol), and cesium carbonate (212 mg, 0.65 mmol) in 10 ml of dioxane under argon and stirred under microwave at 170° C. for 25 minutes. The reaction was completed and the mixture was cooled to room temperature, concentrated under reduced pressure to give the crude product which was separated and purified by preparative liquid chromatography to give compound J-17 (49.2 mg). Yield: 31%, purity: 100%. MS m/z (ESI): 487[M+H]$^+$. $^1$H NMR (400 MHz, DMSO) δ 10.12 (s, 1H), 8.95 (d, J=1.3 Hz, 1H), 8.94 (d, J=1.7 Hz, 1H), 8.64 (t, J=1.5 Hz, 1H), 8.52 (s, 1H), 8.27-8.26 (d, J=1.2 Hz, 1H), 8.22-8.19 (m, 1H), 8.07 (s, 1H), 7.79 (s, 1H), 7.58-7.55 (m, 1H), 6.97 (s, 1H), 6.34-6.32 (d, J=10.0 Hz, 1H), 6.23-6.22 (d, J=2.0 Hz, 1H), 5.74-5.71 (dd, J1=2.0 Hz, J2=10.0 Hz, 1H), 3.83 (s, 3H), 2.86-2.83 (t, J=5.1 Hz, 2H), 2.67 (s, 3H), 2.28 (s, 2H), 2.20 (s, 6H).

Example 18: The Preparation of N-(2-((2-(dimethylamino)ethyl)(methyl)amino)-4-methoxy-5-(3-(-methyl-1H-pyrazol-4-yl)imidazo[1,2-α]pyrazin-6-ylamino)phenyl)acrylamide (J-18)

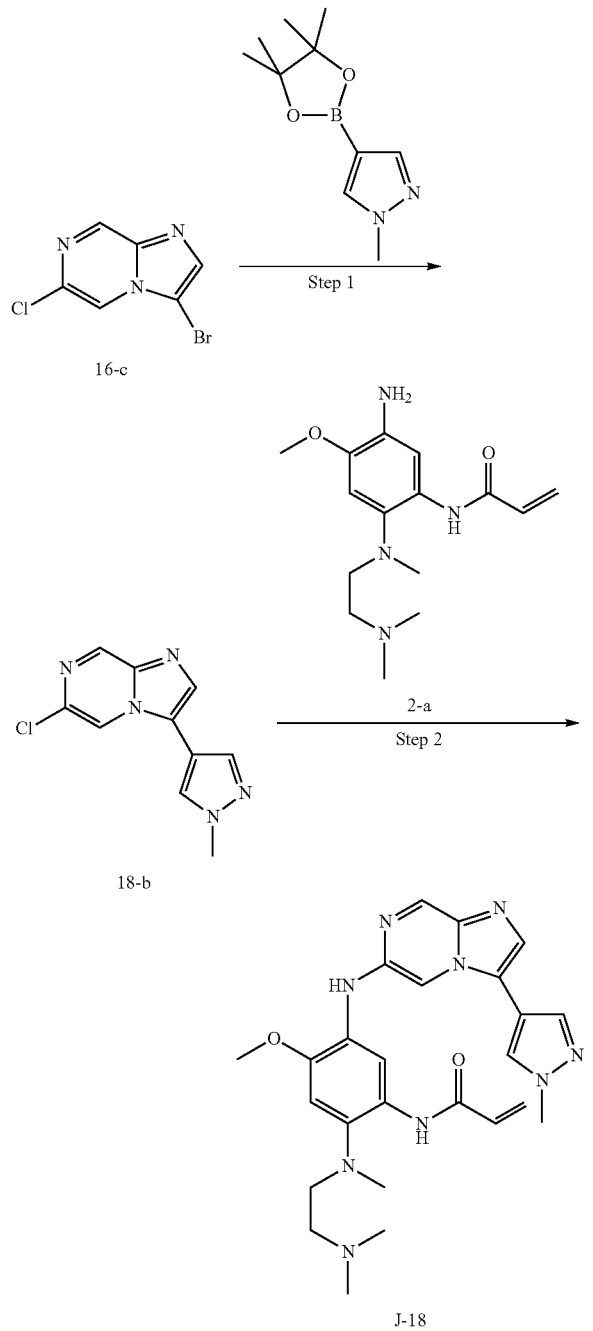

Step 1: [1,1'-bis(diphenylphosphino)ferrocene]dichloropalladium(II) (73 mg, 0.1 mmol) was added to the solution of compound 16-c (465 mg, 2 mmol), 1-methyl-4(4,4,5,5-tetramethyl-1,3,2-dioxaborolan-2-yl)-1H-parazole (395 mg, 1.9 mmol), and sodium carbonate (636 mg, 6 mmol) in acetonitrile 40 ml/water 8 ml under argon and stirred at 70° C. for 4 h. The reaction was completed, and the mixture was cooled to room temperature and extracted with ethyl acetate and water. The combined organic phases were separated and washed with saturated brine. The organic phase was separated, dried over anhydrous sodium sulfate and filtered. The filtrate was concentrated under reduced pressure to give the crude product which was separated and purified by Combi-flash column chromatography [PE:EA=50:50-0:100] to give compound 18-b (281 mg) which was used directly in the next reaction. Yield: 61%, purity: 97%. MS m/z (ESI): 234[M+H]$^+$.

Step 2: Tris(dibenzylideneacetone) dipalladium (37 mg, 0.04 mmol) was added to the solution of compound 18-b (93 mg, 0.4 mmol), compound 2-a (117 mg, 0.4 mmol), 4,5-bis (diphenylphosphino)-9,9-dimethylxanthene (46 mg, 0.08 mmol), and cesium carbonate (261 mg, 0.8 mmol) in 12 ml of dioxane under argon and stirred under microwave at 160° C. for 20 minutes. The reaction was completed and the reaction solution was cooled to room temperature and filtered. The filtrate was concentrated under reduced pressure to give the crude product which was separated and purified by preparative liquid chromatography to give compound J-18 (37.95 mg). Yield: 19.4%, purity: 100%. MS m/z (ESI): 490 [M+H]$^+$. $^1$H NMR (400 MHz, DMSO) δ 10.23 (s, 1H), 8.87-8.86 (d, J=1.3 Hz, 1H), 8.53 (s, 1H), 8.37 (s, 1H), 8.11 (d, J=1.3 Hz, 1H), 7.96 (d, J=0.5 Hz, 1H), 7.91 (s, 1H), 7.53 (s, 1H), 7.00 (s, 1H), 6.39-6.33 (dd, J1=10.0 Hz, J2=16.9 Hz, 1H), 6.25-6.20 (dd, J1=2.1 Hz, J2=16.9 Hz, 1H), 5.76-5.73 (dd, J1=2.0 Hz, J2=9.9 Hz, 1H), 3.93 (s, 3H), 3.85 (s, 3H), 2.86-2.83 (t, J=5.3 Hz, 2H), 2.68 (s, 3H), 2.27-2.24 (t, J=9.7 Hz, 2H), 2.19 (s, 6H).

Example 19: The Preparation of N-(2-(4-(dimethylamino)piperidin-1-yl)-4-methoxy-5-(3(1-methyl-1H-pyrazol-4-yl)imidazo[1,2-α]pyrazinyl 6-amino)phenyl)acrylamide (J-19)

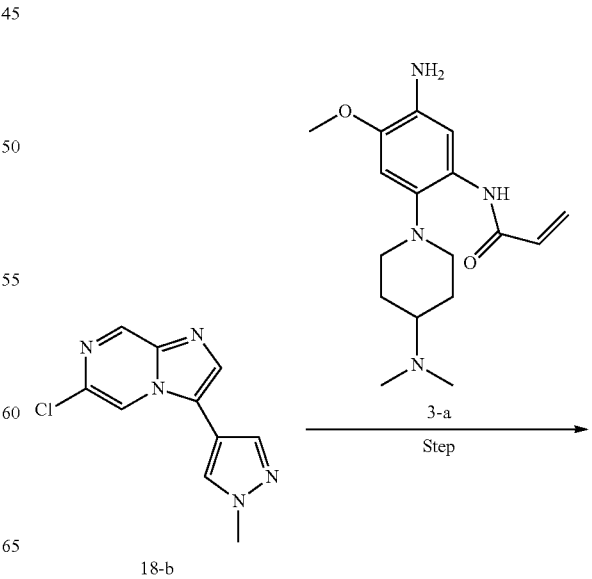

-continued

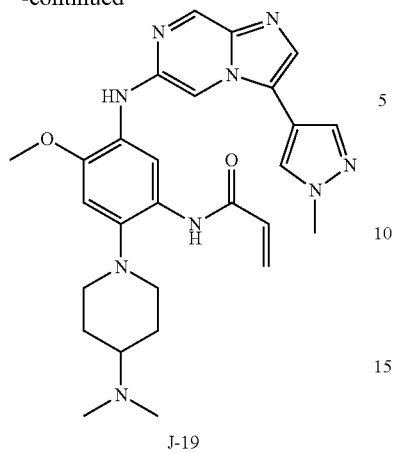

J-19

Step: Tris(dibenzylideneacetone) dipalladium(46 mg, 0.05 mmol) was added to the solution of compound 18-b (117 mg, 0.5 mmol), compound 3-a (159 mg, 0.5 mmol), 4,5-bis(diphenylphosphino)-9,9-dimethylxanthene (58 mg, 0.1 mmol), and cesium carbonate (326 mg, 1.0 mmol) in 12 ml of dioxane under argon and stirred under microwave at 160° C. for 20 minutes. The reaction was completed and the reaction solution was cooled to room temperature and filtered. The filtrate was concentrated under reduced pressure to give the crude product which was separated and purified by preparative liquid chromatography to give compound J-19 (32.9 mg). Yield: 12.8%, purity: 100%. MS m/z (ESI): 516 [M+H]$^+$. $^1$H NMR (400 MHz, DMSO) δ 9.01 (s, 1H), 8.85 (d, J=0.7 Hz, 1H), 8.35 (s, 1H), 8.25 (s, 1H), 8.07 (s, 1H), 7.95 (s, 1H), 7.90 (s, 1H), 7.54 (s, 1H), 6.84 (s, 1H), 6.69-6.63 (dd, J1=10.2 Hz, J2=17.0 Hz, 1H), 6.23-6.19 (dd, J1=1.7 Hz, J2=16.9 Hz, 1H), 5.74-5.71 (t, J=10.2 Hz, 1H), 3.93 (s, 3H), 3.84 (s, 3H), 3.01-2.98 (d, J=11.4 Hz, 2H), 2.68-2.63 (t, J=10.3 Hz, 2H), 2.24 (s, 7H), 1.85-1.82 (d, J=10.7 Hz, 2H), 1.72-1.64 (m, 2H).

Example 20: The Preparation of N-(2-((2-(dimethylamino)ethyl)(methyl)amino)-4-methoxy-5-(5-methyl-7-(1-methyl-1H-pyrazol-4-yl)pyrrolo[1,2-F][1,2,4]triazin-2-ylamino)phenyl)acrylamide (J-20)

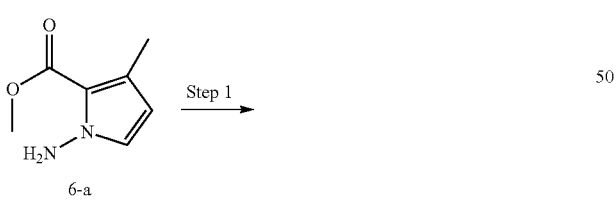

6-a

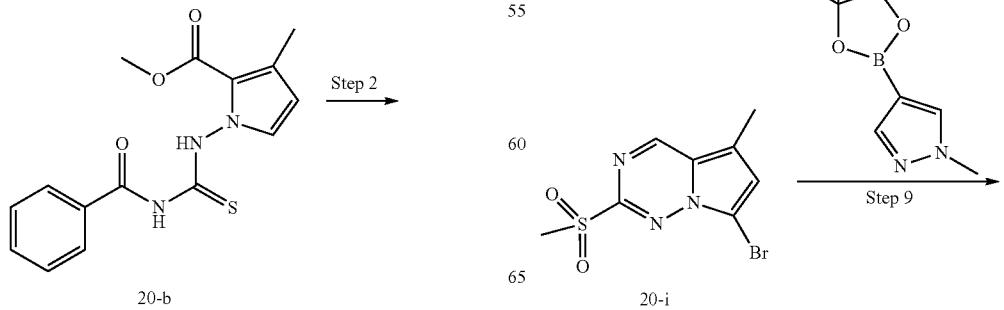

20-b

-continued

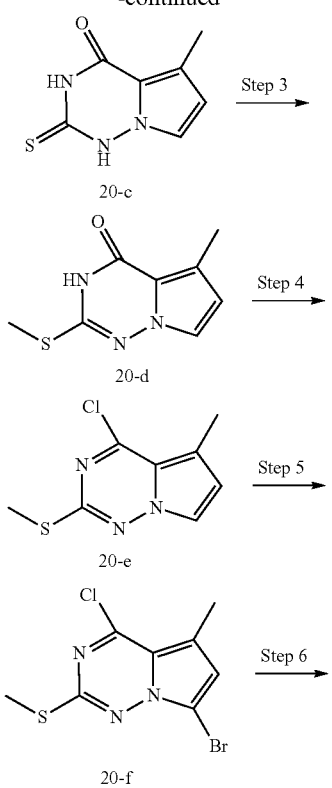

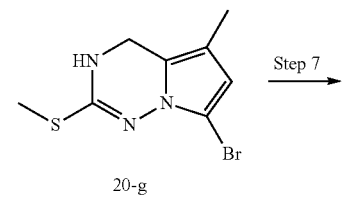

20-h

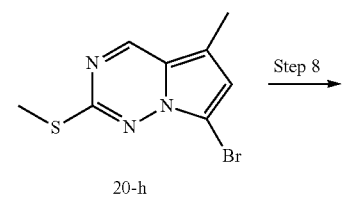

20-i

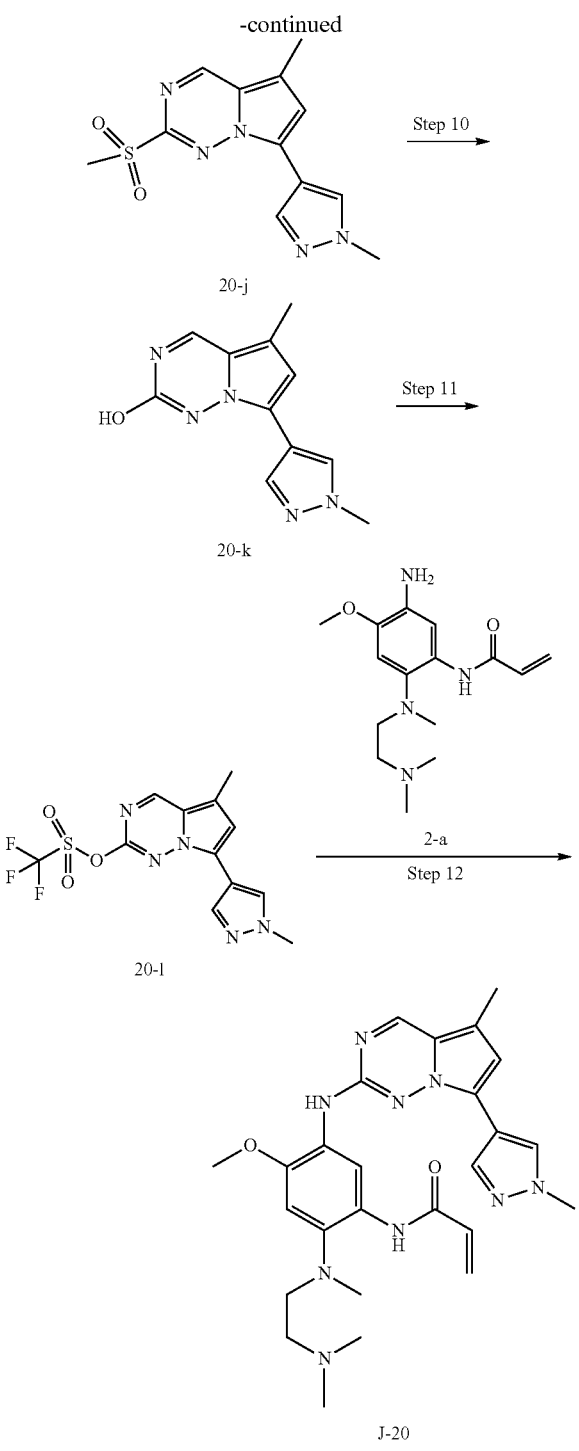

Step 1: Benzoyl isothiocyanate (4.5 g, 27.61 mmol) was added dropwise to a solution of compound 6-a (4.5 g, 26.79 mmol) in 180 ml of tetrahydrofuran at 0° C. and stirred at room temperature for 4 hours. After completion of the reaction, the reaction mixture was concentrated under reduced pressure. Ethyl ether was added to the crude product and stirred, and filtered to give compound 20-b (7.65 g) as a white powder which was directly used in the next reaction. Yield 97%, purity 96%. MS m/z (ESI): 332.1 [M+H]$^+$.

Step 2: Compound 20-b (100 mg, 0.3 mmol) was added to a solution of sodium hydroxide (48 mg, 1.2 mmol) in 1 ml water and heated at 85° C. for 2 hours. The reaction was finished and the mixture was cooled to room temperature. Ethanol (41.5 mg, 0.9 mmol) was added and acetic acid (72 mg, 1.2 mmol) was added dropwise under ice-bath. The mixture was concentrated under reduced pressure to give the white compound 20-c (54 mg) which was directly used in the next reaction. Purity: 91%. MS m/z (EST): 182.1 [M+H]$^+$.

Step 3: Methyl iodide (4.5 g, 28.85 mmol) was added to a solution of compound 20-c (1.0 g, 22.10 mmol) in 110 ml of tetrahydrofuran and stirred at 45° C. for 2 hours. The reaction was completed and the mixture was cooled to room temperature. The reaction solution was concentrated under reduced pressure to give a white solid. 100 ml of water and 100 ml aqueous saturated sodium bicarbonate solution were added to the white solid, stirred and filtered to obtain 20-d (3.96 g) as a white powder which was directly used in the next step. Purity: 92%. MS m/z (ESI): 196.1 [M+H]$^+$.

Step 4: Compound 20-d (3.96 g, 20.31 mmol) was added to 23 ml of phosphorus oxychloride and the mixture was stirred at 120° C. for 1 hour. The reaction was completed and the mixture was cooled to room temperature. The phosphorus oxychloride was evaporated under reduced pressure, and iced water and aqueous ammonia (5.5 ml) were added and stirred for 20 minutes. The filter cake was dissolved in dichloromethane and washed with water and saturated brine. The organic phase was separated and concentrated under reduced pressure to give compound 20-e (4.2 g) as a yellow solid which was directly used in the next step. Purity: 70%. MS m/z (ESI): 214.1 [M+H]$^+$.

Step 5: N-bromosuccinimide (3.49 g, 19.72 mmol) was slowly added to a solution of compound 20-e (4.2 g, 19.72 mmol) in 200 ml of tetrahydrofuran and 100 ml of methanol at 0° C. and stirred at room temperature for 3 hr. The reaction is completed, and the mixture was concentrated, dissolved in dichloromethane, washed with water and saturated brine. The organic phase was separated and concentrated by drying to give crude compound 20-f (6 g) as a yellow solid which was directly used in the next step. Purity: 81%. MS in/z (ESI): 291.9 [M+H]$^+$.

Step 6: Sodium borohydride (874 mg, 23.01 mmol) was added to the solution of compound 20-f (3.36 g, 11.51 mmol) in 40 ml of isopropanol, then heated to 60° C. and stirred for 5 h. The reaction was completed and the mixture was cooled to 0° C. Water was added and then the mixture was extracted with ethyl acetate and water. The organic phase was washed with water and saturated brine. The organic phase was separated, concentrated under reduced pressure to give compound 20-g (2.86 g) as a yellow solid which was directly used in the next step. Purity: 81%. MS m/z (ESI): 260.0[M+H]$^+$.

Step 7: 2,3-dihydro-5,6-dicyano-p-benzoquinone (2.75 g, 121 mmol) was added to the solution of compound 20-g (2.86 g, 110 mmol) in 80 ml of dichloromethane and stirred at room temperature for 1 h. The reaction was completed and the mixture was filtered. The filtrate was concentrated to give the crude product which was purified by column chromatography (petroleum ether/ethyl acetate: 5%) to give compound 20-h (1.92 g) as a yellow solid which was directly used in the next step. Purity: 98%. MS m/z (ESI): 260.0 [M+H]$^+$.

Step 8: Sodium tungstate (3.6 mg, 9.68 mmol) and hydrogen peroxide (1.1 g, 0.01 mmol) were added to the solution of compound 20-h (250 mg, 0.97 mmol) in 8 ml of methanol and stirred at 65° C. for 3 h. The reaction was completed and the mixture was concentrated under reduced pressure, washed with water to give compound 20-i (660 mg) as a yellow solid which was used directly in the next reaction. Yield: 79%. MS m/z (ESI): 290.0 [M+H]$^+$.

Step 9: 1-methyl-4(4,4,5,5-tetramethyl-1,3,2-dioxaborolan-2-yl)-1H-parazole (158 mg, 0.76 mmol), [1,1'-bis(diphenylphosphino)ferrocene]dichloropalladium(II) (56 mg, 0.08 mmol), sodium carbonate (161 mg, 1.52 mmol) and 1 ml of water were added to the solution of compound 20-i (220 mg, 0.76 mmol) in 15 ml of acetonitrile and stirred under microwave at 120° C. for 20 minutes. The reaction was completed and the reaction solution was cooled to room temperature and filtered. The filtrate was concentrated under reduced pressure and purified by Combi-flash column chromatography to give compound 20-j (200 mg) as a yellow solid which was used directly in the next reaction. Yield: 90%. MS m/z (ESI): 292.1 [M+H]+.

Step 10: Sodium hydroxide (371 mg, 9.27 mmol) was added to the solution of compound 20-j (180 mg, 0.62 mmol) in 8 ml of water and stirred at 100° C. for 2 h. The reaction was completed and the mixture was cooled to room temperature, adjusted with acetic acid to pH 4, and extracted with ethyl acetate. The organic phase was separated, collected, dried over anhydrous sodium sulfate and filtered. The filtrate was concentrated under reduced pressure to give compound 20-k (140 mg) as a red solid which was used directly in the next reaction. Yield: 100%. MS m/z (ESI): 230.1 [M+H]+.

Step 11: Compound 20-k (90 mg, 0.39 mmol) was dissolved in 3 ml of dimethylformamide, then N,N-diisopropylethylamine (153 mg, 1.18 mmol) and N-phenyl bis(trifluoromethanesulfonimide) (140 mg, 0.39 mmol) were added and stirred at room temperature for 2 h. The reaction was completed and the mixture was concentrated under reduced pressure to give the crude product which was purified by Combi-flash column chromatography to give compound 20-l (120 mg) as a yellow solid which was used directly in the next reaction. Yield: 90%. MS m/z (ESI): 362.1 [M+H]+.

Step 12: Compound 2-a (41 mg, 0.14 mmol), tris(dibenzylideneacetone) dipalladium(13 mg, 0.014 mmol), 4,5-bis(diphenylphosphino)-9,9-dimethylxanthene (17 mg, 0.027 mmol), and cesium carbonate (91 mg, 0.28 mmol) were added to the solution of compound 20-l (50 mg, 0.14 mmol) in 8 ml of dioxane and stirred under microwave at 160° C. for 15 minutes. The reaction was completed and the reaction solution was cooled to room temperature and filtered. The filtrate was concentrated under reduced pressure to give the crude product which was separated and purified by preparative liquid chromatography to give compound J-20 (2.84 mg). Yield: 4%. MS m/z (ESI): 504.3 [M+H]+.

Example 21: The Preparation of N-(2-(4-(dimethylamino)piperidin-1-yl)-4-methoxy-5-(5-methyl-7-(1-methyl-1H-pyrazol-4-yl) pyrrolo[1,2-F][1,2,4]triazin-2-ylamino)phenyl)acrylamide (J-21)

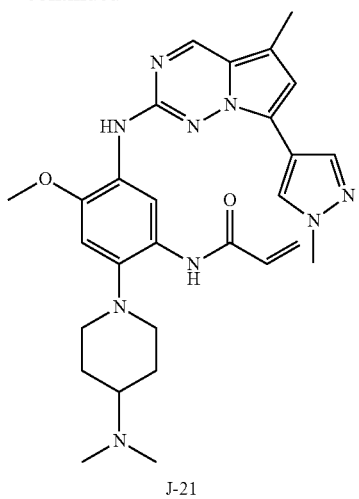

J-21

Step: Compound 3-a (44 mg, 0.14 mmol), tris(dibenzylideneacetone) dipalladium (13 mg, 0.014 mmol), 4,5-bis(diphenylphosphino)-9,9-dimethylxanthene (17 mg, 0.027 mmol), and cesium carbonate (91 mg, 0.28 mmol) were added to the solution of compound 20-l (50 mg, 0.14 mmol) in 8 ml of dioxane and stirred under microwave at 160° C. for 15 minutes. The reaction was completed and the reaction solution was cooled to room temperature and filtered. The filtrate was concentrated under reduced pressure to give the crude product which was separated and purified by preparative liquid chromatography to give compound J-21 (2.76 mg) as yellow oil. Yield: 4%. MS m/z (ESI): 530.2 [M+H]+.

Example 22: The Preparation of N-(2-(4-(dimethylamino)piperidin-1-yl)-4-methoxy-5-(5-methyl-7-(1-methyl-1H-pyrrolo[2,3-b]pyridin-5-yl)pyrrolo[1,2-f][1,2,4]triazin-2-ylamino)phenyl)acrylamide (J-22)

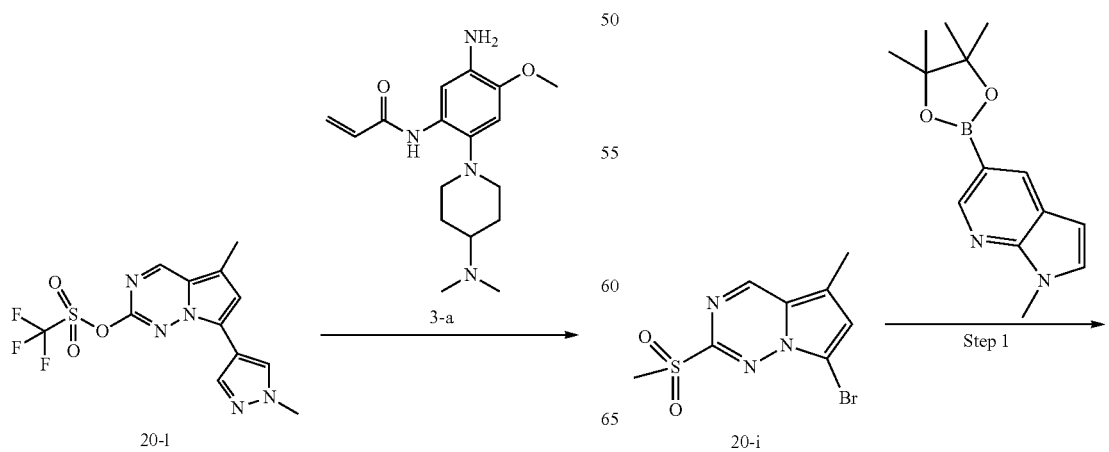

20-l     3-a     20-i

-continued

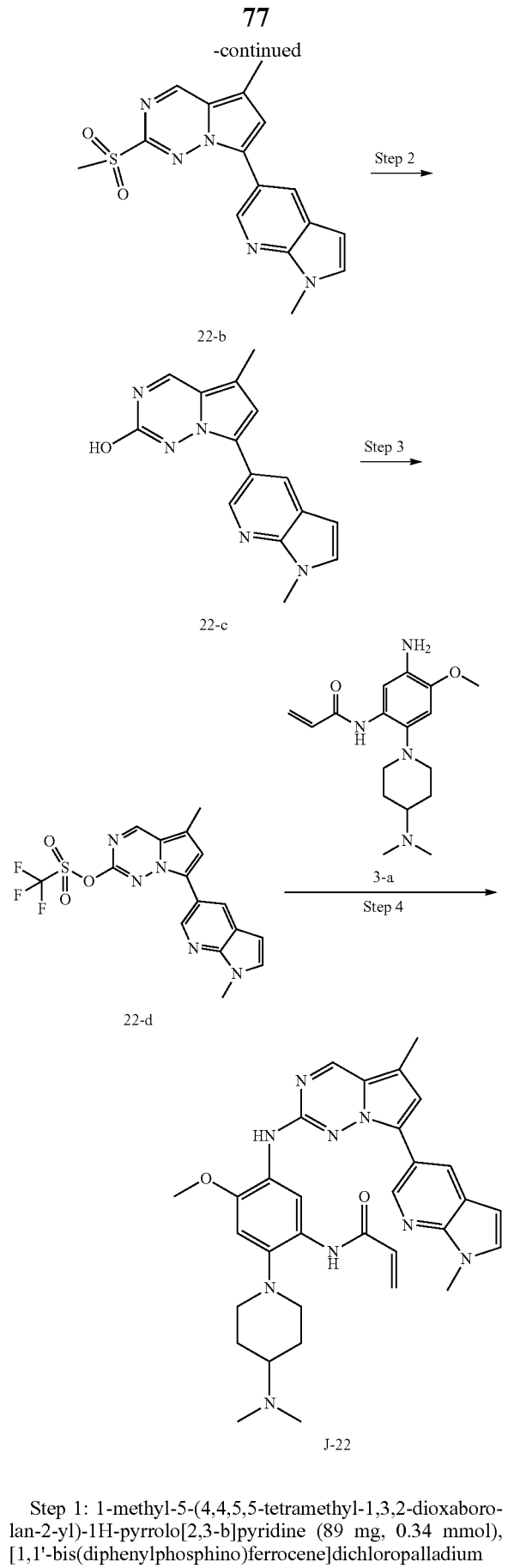

22-b 22-c 22-d

J-22

Step 1: 1-methyl-5-(4,4,5,5-tetramethyl-1,3,2-dioxaborolan-2-yl)-1H-pyrrolo[2,3-b]pyridine (89 mg, 0.34 mmol), [1,1'-bis(diphenylphosphino)ferrocene]dichloropalladium (II) (22 mg, 0.03 mmol), sodium carbonate (73 mg, 0.69 mmol) and two drops of water were added to the solution of compound 20-i (100 mg, 0.34 mmol) in 2 ml of acetonitrile and stirred under microwave at 120° C. for 15 minutes. The reaction was completed and the reaction solution was cooled to room temperature and filtered. The filtrate was concentrated under reduced pressure and purified by Combi-flash column chromatography to give compound 22-b (100 mg) as a yellow solid which was used directly in the next reaction. Yield: 85%. MS m/z (ESI): 342.1 [M+H]$^+$.

Step 2: Sodium hydroxide (234 mg, 5.86 mmol) was added to the solution of compound 22-b (100 mg, 0.29 mmol) in 5 ml of water and stirred at 100° C. for 2 h. The reaction was completed, and the mixture was cooled to room temperature, adjusted with acetic acid to pH 4, and extracted with ethyl acetate. The organic phase was separated and collected, dried over anhydrous sodium sulfate and filtered. The filtrate was concentrated under reduced pressure to give compound 22-c (100 mg) which was used directly in the next reaction. Yield: 100%. MS m/z (ESI): 280.1 [M+H]$^+$.

Step 3: Compound 22-c (100 mg, 0.36 mmol) was dissolved in 10 ml of dimethylformamide, and N,N-diisopropylethylamine (139 mg, 1.08 mmol) was added at 0° C. and stirred for 10 minutes. N-phenyl bis(trifluoromethanesulfonimide) (141 mg, 0.39 mmol) was added and stirred at room temperature for 12 h. The reaction was completed and the mixture was concentrated under reduced pressure to give the crude product which was purified by Combi-flash column chromatography [PE/EA: 50%] to give compound 22-d (250 mg) as a yellow solid which was used directly in the next reaction. Purity: 65%. MS m/z (ESI): 412.1 [M+H]$^+$.

Step 4: Tris(dibenzylideneacetone) dipalladium (36 mg, 0.06 mmol), 4,5-bis(diphenylphosphino)-9,9-dimethylxanthene (45 mg, 0.12 mmol), and cesium carbonate (254 mg, 1.17 mmol) were added to the solution of compound 22-d (240 mg, 0.58 mmol) and compound 3-a (123 mg, 0.58 mmol) in 16 ml of dioxane and stirred under microwave at 160° C. for 20 minutes. The reaction was completed and the reaction solution was cooled to room temperature and filtered. The filtrate was concentrated under reduced pressure to give the crude product which was separated and purified by preparative liquid chromatography to give compound J-22 (24 mg). Purity: 6.09% (UV254). MS m/z (ESI): 580.3 [M+H]$^+$.

Example 23: The Preparation of N-(2-(4-(dimethylamino)piperidin-1-yl)-4-methoxy-5-(5-methyl-7-(pyridin-3-yl)pyrrolo[1,2-f][1,2,4]triazin-2-ylamino)phenyl)acrylamide (J-23)

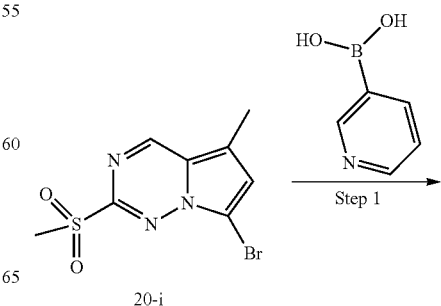

20-i

-continued

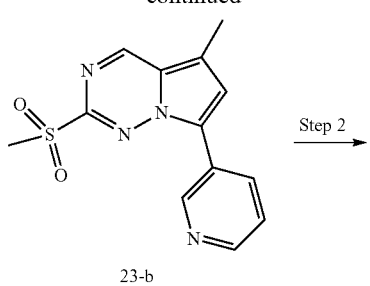

23-b

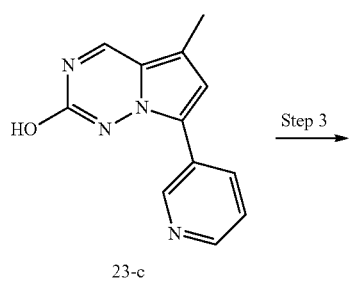

23-c

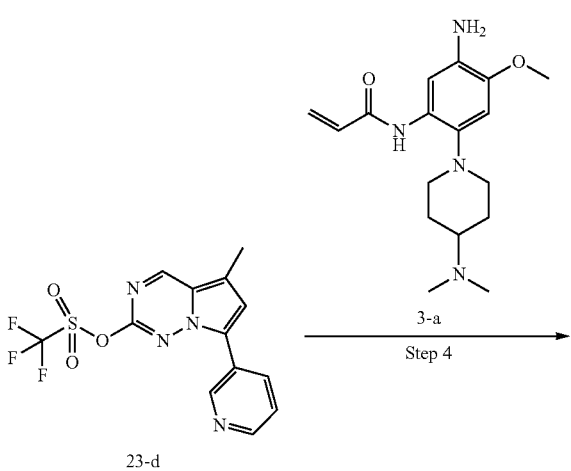

23-d

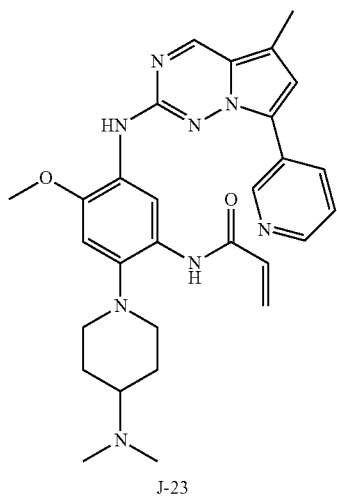 [SMILES: C=CC(=O)Nc1cc(Nc2ncc3c(C)cc(-c4cccnc4)n3n2)c(OC)cc1N1CCC(N(C)C)CC1]

J-23

Step 1: Pyridin-3-yl boric acid (71 mg, 0.34 mmol), [1,1'-bis(diphenylphosphino)ferrocene]dichloropalladium (II) (22 mg, 0.034 mmol), sodium carbonate (73 mg, 0.69 mmol) and two drops of water were added to the solution of compound 20-I (100 mg, 0.34 mmol) in 2 ml of acetonitrile and stirred under microwave at 120° C. for 15 minutes. The reaction was completed and the reaction solution was cooled to room temperature and filtered. The filtrate was concentrated under reduced pressure and purified by Combi-flash column chromatography to give compound 23-b (100 mg) as a yellow solid which was used directly in the next reaction. Yield: 84%. MS m/z (ESI): 389.1 [M+H]$^+$.

Step 2: Sodium hydroxide (278 mg, 6.94 mmol) was added to the solution of compound 23-b (100 mg, 0.35 mmol) in 5 ml of water and stirred at 100° C. for 2 h. The reaction was completed and the mixture was cooled to room temperature, adjusted with acetic acid to pH 4, to and extracted with ethyl acetate. The organic phase was separated, collected, dried over anhydrous sodium sulfate and filtered. The filtrate was concentrated under reduced pressure to give compound 23-c (95 mg) which was used directly in the next reaction. Yield: 100%. MS m/z (ESI): 227.1 [M+H]$^+$.

Step 3: Compound 23-c (75 mg, 0.33 mmol) was dissolved in 3 ml of dimethylformamide, and N,N-diisopropylethylamine (128 mg, 0.99 mmol) and N-phenyl bis(trifluoromethanesulfonimide) (130 mg, 0.36 mmol) were added at 0° C. and stirred at room temperature for 1 h. The reaction was completed and the mixture was concentrated under reduced pressure to give the crude product which was purified by Combi-flash column chromatography to give compound 23-d (50 mg) as a yellow solid which was used directly in the next reaction. Purity: 42%. MS m/z (ESI): 359.0[M+H]$^+$.

Step 4: Tris(dibenzylideneacetone) dipalladium (10 mg, 0.01 mmol), 4,5-bis(diphenylphosphino)-9,9-dimethylxanthene (12 mg, 0.02 mmol) and cesium carbonate (70 mg, 0.21 mmol) were added to the solution of compound 23-d (37 mg, 0.1 mmol) and compound 3-a (33 mg, 0.1 mmol) in 6 ml of dioxane and stirred under microwave at 160° C. for 100 minutes. The reaction was completed and the reaction solution was cooled to room temperature and filtered. The filtrate was concentrated under reduced pressure to give the crude product which was separated and purified by preparative liquid chromatography to give compound J-23 (16 mg). Purity: 18% (UV254). MS m/z (EST): 527.3 [M+H]$^+$.

Examples 24-54

Compounds J-24 to J-54 have the structure of formula (I), wherein the substituents $Z_1$, $Z_2$, $R_3$ and $R_4$ are defined as shown in Table 5, $R_1$, $R_2$, $R_6$, and $R_7$ are H and $R_5$ is methoxy. Compounds J-24-J-54 can be prepared by the similar methods for Compounds J-1 to J-23 according to the different structures listed in the following table. All starting materials and intermediates used can be prepared by those skilled in the art according to the existing methods.

TABLE 5
| Example No. | Compound | R$_3$ | R$_4$ | Z$_1$ | Z$_2$ | MS [M + H]$^+$ |
|---|---|---|---|---|---|---|
| 24 | J-24 | 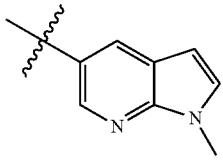 [SMILES: *c1cnc2c(ccn2C)c1] | 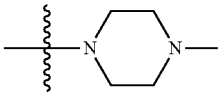 | N | CH | 538.2 |
| 25 | J-25 | 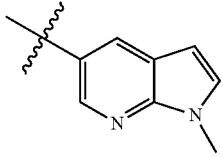 [SMILES: *c1cnc2c(ccn2C)c1] | 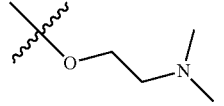 [SMILES: *OCCN(C)C] | N | CH | 527.2 |
| 26 | J-26 | 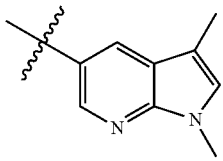 [SMILES: *c1cnc2c(c1)c(C)cn2C] | 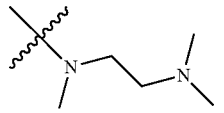 [SMILES: *N(C)CCN(C)C] | N | CH | 554.3 |
| 27 | J-27 | 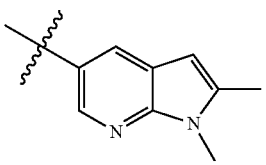 [SMILES: *c1cnc2c(c1)cc(C)n2C] | 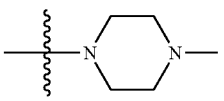 | N | C—CH$_3$ | 566.2 |
| 28 | J-28 | 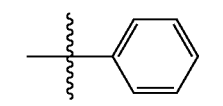 [SMILES: *c1ccccc1] | 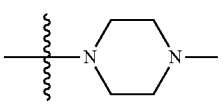 | N | CH | 484 |
| 29 | J-29 | 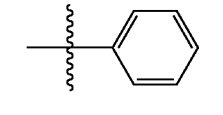 | 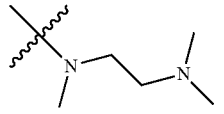 [SMILES: *N(C)CCN(C)C] | N | C—CH$_3$ | 500.3 |
| 30 | J-30 | 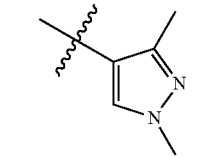 |  | N | C—CH$_3$ | 544.3 |
| 31 | J-31 | 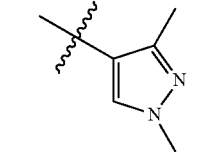 [SMILES: *c1cn(C)nc1C] | 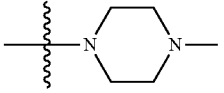 | N | C—CH$_3$ | 516 |
| 32 | J-32 | 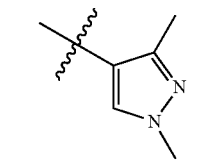 [SMILES: *c1cn(C)nc1C] | 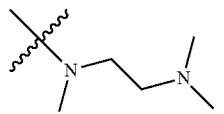 [SMILES: *N(C)CCN(C)C] | N | C—CH$_3$ | 518.2 |

TABLE 5-continued

| Example No. | Compound | R₃ | R₄ | Z₁ | Z₂ | MS [M + H]⁺ |
|---|---|---|---|---|---|---|
| 33 | J-33 | 4-(1-methyl-1H-pyrazolyl) | -N(CH₃)CH₂CH₂N(CH₃)₂ | N | CH | 504 |
| 34 | J-34 | 4-(1,3-dimethyl-1H-pyrazolyl) | -N(CH₃)CH₂CH₂N(CH₃)₂ | N | CH | 518.2 |
| 35 | J-35 | 4-(1,3-dimethyl-1H-pyrazolyl) | 4-(dimethylamino)piperidin-1-yl | N | C—CH₃ | 558.3 |
| 36 | J-36 | 4-(1-methyl-1H-pyrazolyl) | 4-methylpiperazin-1-yl | N | C—CH₃ | 502 |
| 37 | J-37 | 4-(1-methyl-1H-pyrazolyl) | -OCH₂CH₂N(CH₃)₂ | N | C—CH₃ | 491 |
| 38 | J-38 | 4-(1-methyl-1H-pyrazolyl) | -OCH₂CH₂N(CH₃)₂ | CH | N | 477 |
| 39 | J-39 | 4-(1,3-dimethyl-1H-pyrazolyl) | -N(CH₃)CH₂CH₂N(CH₃)₂ | CH | N | 504.3 |
| 40 | J-40 | 4-(1-methyl-1H-pyrazolyl) | 4-(dimethylamino)piperidin-1-yl | CH | N | 515 |
| 41 | J-41 | 4-(1-methyl-1H-pyrazolyl) | 4-(dimethylamino)piperidin-1-yl | N | CH | 515 |

TABLE 5-continued

| Example No. | Compound | R₃ | R₄ | Z₁ | Z₂ | MS [M + H]⁺ |
| --- | --- | --- | --- | --- | --- | --- |
| 42 | J-42 | 3-(1-methylpyrrolyl) | -N(CH₃)CH₂CH₂N(CH₃)₂ | N | C—CH₃ | 503 |
| 43 | J-43 | 3-(1-methylpyrrolyl) | 4-methylpiperazin-1-yl | N | CH | 487.3 |
| 44 | J-44 | 2,3-dimethyl-1-methylpyrrol-4-yl | 4-(dimethylamino)piperidin-1-yl | N | CH | 543.3 |
| 45 | J-45 | quinolin-3-yl | -OCH₂CH₂N(CH₃)₂ | N | CH | 524 |
| 46 | J-46 | quinolin-3-yl | 4-(dimethylamino)piperidin-1-yl | N | C—CH₃ | 577.3 |
| 47 | J-47 | quinolin-3-yl | -N(CH₃)CH₂CH₂N(CH₃)₂ | CH | N | 537.2 |
| 48 | J-48 | isopropyl | -N(CH₃)CH₂CH₂N(CH₃)₂ | N | C—CH₃ | 466 |
| 49 | J-49 | methyl | -N(CH₃)CH₂CH₂N(CH₃)₂ | CH | N | 424 |
| 50 | J-50 | methyl | 4-methylpiperazin-1-yl | N | CH | 422.2 |
| 51 | J-51 | cyclopropyl | -OCH₂CH₂N(CH₃)₂ | N | CH | 437 |
| 52 | J-52 | cyclopropyl | 4-(dimethylamino)piperidin-1-yl | CH | N | 476.3 |

TABLE 5-continued

| Example No. | Compound | R₃ | R₄ | $Z_1$ | $Z_2$ | MS [M + H]⁺ |
|---|---|---|---|---|---|---|
| 53 | J-53 | 3-pyridyl | piperazin-1-yl | N | CH | 485.2 |
| 54 | J-54 | 3-pyridyl | 4-(dimethylamino)piperidin-1-yl | CH | N | 513 |

Test Example 1: Assay of Inhibitory Activity on Wild Type EGFR and Mutant EGFR Kinase All reagents used in the following z'-lyte assay were purchased from Invitrogen.

The inhibitory activity on T790M/L858R double mutant EGFR kinase (Invitrogen, PV4879) and wild-type EGFR kinase (Invitrogen, PV3872) were determined by the z'-lyte assay.

The working concentrations of each component in 10 μL T790M/L858R kinase reaction system were: 25 μM ATP, 0.1 ng/μL T790M/L858R kinase, 2 μM Tyr04 substrate (Invitrogen, PV3193). The concentration of DMSO after addition of the compound prepared in the above examples of the present invention (i.e., the compound to be tested) was 2 vol %.

The working concentrations of each component in 10 μL wild-type EGFR kinase reaction system were: 10 μM ATP, 0.8 ng/μL wild-type EGFR kinase, 2 μM Tyr04 substrate (Invitrogen, PV3193). The concentration of DMSO after addition of the compound to be tested was 2 vol %.

10 mM drug stock solution was dissolved at room temperature and gradiently diluted to a final concentration of 4-0.002 μM with 8 vol % DMSO solution. 2.5 μL of the solution of the compound to be tested and 5 μL of the mixture of T790M/L858R kinase (or wild-type EGFR kinase) and Tyr04 substrate diluted with the reaction buffer were added to each well. Then 2.5 μl of ATP was added to initiate the reaction. Wherein, ATP was replaced by the reaction buffer in well C1, no drug was added to well C2, and the phosphorylated substrate was added to well C3 according to the instructions. The mixture was allowed to react at 25° C. in a shaker in dark for 60 min. 5 μL of Development Reagent B (Invitrogen, diluted with TR-FRET dilution buffer) was added and allowed to react at room temperature in the shaker for 60 minutes. The plate was read on a Victor X5 plate reader (PerkinElmer) and the absorbance was measured at excitation wavelengths of 405 nm and emission wavelengths of 450 nm and 520 nm (for example, $C3_{520\ nm}$ indicates the absorbance for well C3 at 520 nm).

The inhibition rate was calculated according to the following method (refer to the instructions of Invitrogen, PV3193):
1. ER=Coumarin Emission (450 nm)/Fluorescein Emission (520 nm)
2. Phosphorylation ratio=$(1-(ER \times C3_{520\ nm} - C3_{450\ nm})/((C1_{450\ nm} - C3_{450\ nm}) + ER \times (C3_{520\ nm} - C1_{520\ nm}))) \times 100\%$
3. Inhibition ratio (IR)=(1−(phosphorylation ratio of the test compound)/(phosphorylation ratio of C2))×100%

The half-inhibitory concentration $IC_{50}$ was obtained through fitting calculation by using XLFIT 5.0 software (IDBS, UK).

TABLE 1

Enzyme inhibitory activity and selective inhibitory activity

| Compound No. | T790M/L858R ($IC_{50}/\mu M$) | EGFR WT ($IC_{50}/\mu M$) | Selective inhibitory activity against enzymes [$IC_{50}$ (EGFR WT)/ $IC_{50}$ (T790M/L858R)] |
|---|---|---|---|
| J-1 | 0.001 | 0.004 | 4 |
| J-2 | 0.002 | 0.023 | 11.5 |
| J-3 | 0.001 | 0.010 | 10 |
| J-4 | 0.002 | 0.035 | 17.5 |
| J-5 | 0.003 | 0.009 | 3 |
| J-6 | 0.0024 | 0.013 | 5.42 |
| J-7 | 0.002 | 0.005 | 2.5 |
| J-8 | 0.002 | 0.112 | 56 |
| J-9 | 0.016 | 0.105 | 6.6 |
| J-10 | 0.001 | 0.003 | 3 |
| J-11 | 0.0024 | 0.010 | 4.2 |
| J-12 | 0.0019 | 0.008 | 4.2 |
| J-13 | 0.005 | 0.021 | 4.2 |
| J-14 | 0.009 | 0.104 | 11.6 |
| J-15 | 0.262 | >1 | 3.8 |
| J-20 | 0.012 | 0.294 | 24.5 |
| J-21 | 0.294 | >1 | 3.4 |
| AZD-9291 | 0.002 | 0.003 | 1.5 |
| BIBW2992 | 0.005 | 0.001 | 0.2 |

It can be seen from Table 1 that the compounds in the examples of the present invention exhibit a strong inhibitory activity against the EGFR mutant enzyme (T790M/L858R) but a weak inhibitory activity against EGFR wild-type enzyme (T790M WT) compared with the positive control BIBW2992 (alfatinib) and AZD-9291 (the preparation method thereof is referred to WO2013014448A1, and the structure is as follows). Therefore, the compounds of the present invention have excellent selective inhibitory activity against EGFR mutant enzymes.

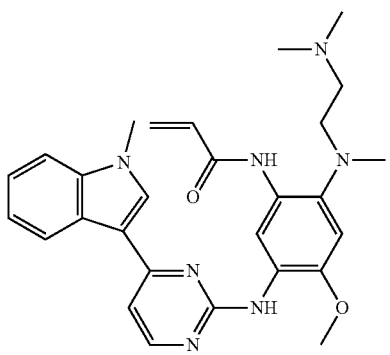

AZD-9291

Moreover, the present inventors have also synthesized other compounds including compound CC0922, wherein the site of acrylamide group

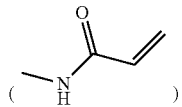

is different from that in formula (I) compound. The results indicate that compound CC0922 is very unstable and not suitable for medicinal application.

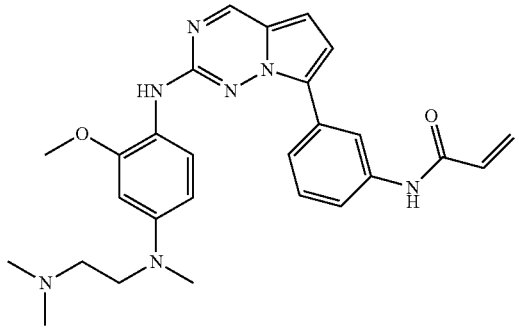

CC0922

Test Example 2: Inhibition of EGFR Phosphorylation in A431 (EGFR Wild-Type) and H1975 (EGFR T790M Mutant) Cells by EGFR T790M Inhibitors (Determined by ELISA)

In the following methods, the reagents used, the preparation methods of solutions, the cell treatment and the preparation steps of the lysis solution, as well as the ELISA assay steps, were carried out according to the instructions of R&D DYC3570, R&D DYC1095E and R&D DYC1095BE.

I. Reagents and Solutions

Cell lysis buffer: 1% (W/V) NP-40, 20 mM Tris (pH 8.0), 137 mM (1 NaCl, 10% (V/V) glycerol, 1 mM NaVO$_3$, 2 mM EDTA.

Cell lysis solution: Cell lysis buffer+10 μg/mL Aprotinin (Sigma)+10 μg/mL Leupeptin (Sigma), prepared on site.

1×PBS buffer: NaCl: 0.137M, KCl: 0.0027M, Na$_2$PO$_4$-12H$_2$O: 0.01M, KH$_2$PO$_4$: 0.0015M, pH7.4.

Wash buffer: PBS buffer containing 0.05% (v/v) Tween-20.

Detection antibody diluent: 20 mM Tris, 137 mM NaCl, 0.05% (V/V) Tween-20, 0.1% (W/V) BSA, pH 7.2-7.4.

Blocking solution: PBS buffer containing 1% (w/v) BSA. ELISA kits: R&D DYC3570, R&D DYC1095E and R&D DYC1095BE.

II. H1975 Cells 2.1 H1975 Cell Treatment and Lysis Solution Preparation (1) H1975 cells (purchased from the Cell Bank of the Type Culture Collection Committee, Chinese Academy of Sciences) were seeded into 96-well plates at a density of $1\times10^4$/well, each cell containing 90 μl of RPMI1640 medium with 10% (V/V) FBS, and cultured overnight at 37° C. in 5% (v/v) CO$_2$.

(2) The compounds to be tested were diluted in accordance with the drug dilution method in the MTT assay. 10 μL of the diluted compound or diluted DMSO was added to the corresponding wells of the cell culture plate, and the final concentration of DMSO was 0.5% (V/V). The plate was cultured at 37° C. in 5% (v/v) CO$_2$ for 1 h. The cell culture system treated with DMSO alone was used as cell control.

(3) The medium was removed and then 100 μL of cell lysis solution was added. The plate was sealed and placed in a refrigerator at −80° C. overnight. The cell lysis buffer was used as blank control.

2.2 ELISA Assay Steps

The assay was conducted according to the instructions given in R&D DYC1095E or R&D DYC1095BE.

(1) R&D capture antibody ((DYC1095BE or DYC1095E)) was diluted with PBS in the proportion of 1:180. 100 μL of the diluted antibody was added to each well of the ELISA reaction plate (Corning costar 42592) and the coated plate was incubated at 25° C. with shaking overnight.

(2) The plate was washed 3 times with 360 μL of the wash buffer.

(3) 300 μL of the blocking solution was added and the plate was incubated at 25° C. with shaking for 2 hours.

(4) The plate was washed 3 times with 360 μL of the wash buffer.

(5) 40 μL of cell lysis buffer and 60 μL of cell lysis solution were added and the plate was incubated at 25° C. with shaking for 2 hours.

(6) The plate was washed 3 times with 360 μL of the wash buffer.

(7) The detection antibody was diluted with the detection antibody diluent in the proportion specified in the instructions of the kit. 100 μL of the diluted antibody was added to each well and the plate was incubated at 25° C. with shaking in dark for 1 h.

(8) The plate was washed 3 times with 360 μL of wash buffer.

(9) A reagent and B reagent in the TMB substrate (R&D DY999) were mixed in 1:1. 100 μL of the mixture was added to each well and incubated in dark at 25° C. with shaking for 20 min.

(10) 50 μL of 2N H$_2$SO$_4$ was added to each well.

(11) The plate was read with a microplate reader (Thermo Multiskan K3). OD 450 values and OD570 values of the cell control, blank control, and drug treatment wells were measured. $OD_{cell}$, $OD_{blank}$ and $OD_{drug\ treatment}$ were obtained by subtracting the corresponding OD570 value from the OD 450 value of the same well.

2.3 Data Analysis

Inhibition rate (%)=100%×($OD_{cell}$−$OD_{drug\ treatment}$)/($OD_{cell}$−$OD_{blank}$)

2.4 $IC_{50}$ values were calculated using the XLFIT 5.0 software based on the calculated inhibition rate and the results are shown in Table 2.

III. A431 Cells 3.1 A431 Cell Treatment and Testing Procedures (1) A431 cells (purchased from the Cell Bank of the Type Culture Collection Committee, Chinese Academy of Sciences) were seeded in 96-well plates at a density of $1\times10^4$/well in 90 μl of DMEM medium containing 10% FBS and cultured at 37° C. in 5% $CO_2$ overnight.

(2) The A431 cell culture medium was replaced with 90 μl of serum-free DMEM medium and the plate was cultured overnight.

(3) The compound to be tested was diluted according to the drug dilution method in MTT assay. 10 μL of the diluted compound or diluted DMSO was added to the corresponding wells of the cell culture plate, and the final concentration of DMSO was 0.5%. The plate was cultured at 37° C. in 5% $CO_2$ for 1 hour. 10 μl of 2 μg/L EGF(R&D, 236-EG-01M) was added to each well except the cell control well and 10 μl of serum-free DMEM was added to the cell well and incubated for 45 minutes. The cells without EGF and drug treatment were used as cell control, and the cells treated with EGF without drugs were used as EGF control.

(4) The medium was removed and then 100 μL of the cell lysis solution was added. The plate was sealed and placed in a refrigerator at −80° C. overnight.

3.2 ELISA Assay Steps

The assay was conducted according to the instructions given in R&D DYC3570E.

(1) R&D capture antibody (DYC3570E) was diluted with PBS in the proportion of 1:180. 100 μL of the diluted antibody was added to each well of the ELISA reaction plate (Corning costar 42592) and the coated plate was incubated at 25° C. with shaking overnight.

(2) The plate was washed 3 times with 360 μL of the wash buffer.

(3) 200 μL of the blocking solution was added and the plate was incubated at 25° C. with shaking for 2 hours.

(4) The plate was washed 3 times with 360 μL of wash buffer.

(5) 40 μL of cell lysis buffer and 60 μL of cell lysis solution were added and the plate was incubated at 25° C. with shaking for 2 hours.

(6) The plate was washed 3 times with 360 μL of the wash buffer.

(7) The detection antibody was diluted with the detection antibody diluent in the proportion specified in the instructions of the kit. 100 μL of the diluted antibody was added to each well and the plate was incubated at 25° C. with shaking in dark for 1 h.

(8) The plate was washed 3 times with 360 μL of the wash buffer.

(9) A reagent and B reagent in TMB substrate (R&D DY999) were mixed in 1:1. 100 μL of the mixture was added to each well and incubated in dark at 25° C. with shaking for 20 min.

(10) 50 μL of 2N $H_2SO_4$ was added to each well.

(11) The plate was read with a microplate reader (Thermo Multiskan K3). OD 450 values and OD570 values of the cell control, blank control, and drug treatment wells were measured. $OD_{EGF}$, $OD_{drug}$ and $OD_{cell}$ were obtained by subtracting the corresponding OD570 value from the OD 450 value of the same well.

3.3 Data Analysis

Inhibition rate (%)=100%×($OD_{EGF}$−$OD_{drug}$)/($OD_{EGF}$−$OD_{cell}$)

3.4 $IC_{50}$ values were calculated using the XLFIT 5.0 software based on the calculated inhibition rate and the results are shown in Table 2.

TABLE 2

Results of the cell activity by ELISA assay

| Compound No. | H1975 cell ($IC_{50}$/μM) | A431 cell ($IC_{50}$/μM) | Selective inhibitory activity against targets at the cell level [$IC_{50}$ (A431 cell)/$IC_{50}$ (H1975 cell)] |
|---|---|---|---|
| J-1 | 0.012 | 0.112 | 9.3 |
| J-2 | 0.025 | 0.303 | 12.1 |
| J-3 | 0.001 | 0.093 | 93 |
| J-4 | 0.004 | 1.799 | 450 |
| J-5 | 0.106 | 0.208 | 2 |
| J-6 | 0.027 | 0.309 | 11.4 |
| J-8 | 0.163 | 0.495 | 3 |
| J-9 | 0.186 | 0.920 | 5 |
| J-11 | 0.063 | 0.237 | 3.8 |
| J-12 | 0.015 | 0.023 | 1.5 |
| J-13 | 0.043 | 0.301 | 7 |
| J-14 | 0.106 | 2.704 | 25.5 |
| J-16 | 0.171 | 0.211 | 1.2 |
| J-17 | 0.734 | 1.164 | 1.6 |
| J-19 | 0.289 | 0.327 | 1.13 |
| BIBW2992 | 0.021 | 0.005 | 0.24 |

As can be seen from Table 2, the compounds of the examples of the present invention have a better selective inhibitory activity against EGFR mutant cells as compared with the positive control BIBW2992.

Test Example 3: Cell Inhibitory Activity Tested by MTT (3-(4,5-dimethylthiazole-2)-2,5-diphenyltetrazolium bromide) assay The steps of the MTT assay were carried out using methods well known to those skilled in the art, and all the reagents used in the methods are commercially available.

Firstly, the medium was removed and 1 mL of 0.25% trypsin/EDTA (Gibco, 25200-056) was added. After the first wash, another 1.5 mL of trypsin/EDTA was added to digest the adherent cells until the cells detached. Then 3.5 mL of the culture medium was added to terminate the digestion. The digested cell suspension was transferred to a 15 mL centrifuge tube and centrifuged at 1300 rpm for 3 minutes. The supernatant was discarded and the cells were resuspended in fresh medium. The cells were then counted and diluted to the following concentrations: 27,800 cells per milliliter of H1975 cells, 33,300 cells per milliliter of A431 cells and NIH3T3 cells (purchased from the Cell Bank of the Type Culture Collection Committee, Chinese Academy of Sciences). Cells were seeded in 96 well plates (BD 3072), 90 μL/well, and cultured overnight.

A431 cell culture medium: DMEM (Hyclone SH30243.01B) containing 10% FBS (Gibco, 10099-141);

NIH3T3 cell culture medium: DMEM (Hyclone SH30243.01B) containing 10% FBS (Gibco, 10099-141);

H1975 cell culture medium: RPMI-1640 (Hyclone SH30809.01B) containing 10% FBS (Gibco, 10099-141);

20 μL of 10 mM compound to be tested (200×) was diluted with the following concentration gradients (2000, 666.67, 222.22, 74.07, 24.69, 8.23, 2.74, 0.91 μM), followed by adding serum-free medium (final concentrations: 100, 33.33, 11.11, 3.404, 1.235, 0.412, 0.137, 0.046 μM), and 10 μl of drug was added to each well of the cell culture plate with a final DMSO concentration of 0.5%.

After the drug was added, the cells were incubated in an incubator for 72 hours. 10 μL of 5 mg/ml MTT (Sigma, M5655) solution was added to each well. The 96-well plate was then incubated in a 37° C. and 5% $CO_2$ incubator for 4 h.

The plate was then centrifuged at 2000 rpm for 5 min. After the supernatant was removed, 150 μl of DMSO was added to each well and the plate was shaken in a shaker until all crystal violet was dissolved. Finally, absorbance at 492 nm was measured using a microplate reader and $IC_{50}$ was calculated using the XLFIT 5.0 software (IDBS, UK).

TABLE 3

Inhibitory activity and selectivity of the compounds on cell growth

| Compound No. | H1975 cell ($IC_{50}$/μM) | A431 cell ($IC_{50}$/μM) | Selective inhibitory activity against cell growth [$IC_{50}$ (A431 cell)/ $IC_{50}$ (H1975 cell)] |
|---|---|---|---|
| J-1 | <0.00457247 | 0.327 | 71.6 |
| J-2 | 0.011 | 0.403 | 36.6 |
| J-3 | 0.008 | 0.168 | 21 |
| J-4 | 0.014 | 0.461 | 32.9 |
| J-5 | 0.023 | 0.354 | 15.4 |
| J-6 | 0.028 | 0.427 | 15.3 |
| J-7 | 0.010 | 0.231 | 23.1 |
| J-8 | 0.097 | 3.191 | 32.9 |
| J-9 | 0.125 | 1.653 | 13.2 |
| J-10 | 0.009 | 0.147 | 16.3 |
| J-11 | 0.026 | 0.621 | 23.9 |
| J-12 | 0.009 | 0.332 | 36.9 |
| J-13 | 0.013 | 0.369 | 28.4 |
| J-14 | 0.126 | 3.557 | 28.2 |
| J-16 | 0.388 | 1.147 | 3 |
| J-17 | 0.424 | 2.951 | 7 |
| J-18 | 0.251 | 1.563 | 6.2 |
| J-19 | 0.243 | 1.212 | 5 |
| BIBW2992 | 0.088 | 0.029 | 0.33 |

As can be seen from Table 3, compared to the positive control BIBW2992, the example compounds of the present invention showed a stronger inhibitory activity against EGFR mutant type cells (H1975 cells), but showed a weak inhibition to EGFR wild type cells (A431 cells). The compounds of the present invention thus have an excellent selective inhibitory activity against EGFR mutant cells.

TABLE 4

Results of the toxicity test of the compounds on NIH3T3 cells

| Compound No. | MTT assay for NIH3T3 cells ($IC_{50}$/μM) |
|---|---|
| J-1 | 4.834 |
| J-2 | 5.457 |
| J-3 | 3.905 |
| J-4 | 3.646 |
| J-5 | 2.818 |
| J-6 | 8.205 |
| J-7 | 3.375 |
| J-9 | >10 |
| J-10 | 3.271 |
| J-11 | 5.567 |
| J-12 | 4.734 |
| J-13 | 2.966 |
| J-14 | 7.774 |
| J-16 | >10 |
| J-17 | >10 |
| J-18 | >10 |
| J-19 | >10 |
| BIBW2992 | 2.750 |

As can be seen from Table 4, the example compounds of the present invention have higher $IC_{50}$ values for NIH3T3 cells and thus exhibit less toxicity compared to the positive control BIBW2992.

The results of the assays of in vitro kinase activity inhibition, intracellular EGFR phosphorylation level inhibition and cell growth inhibition demonstrate that, at the level of nanomole concentration, the example compounds of the present invention exhibit a stronger inhibitory activity against mutant EGFR enzyme activity, EGFR phosphorylation level, and cell proliferation but a weak inhibition on wild-type EGFR enzyme activity, EGFR phosphorylation level, and cell proliferation. Therefore, the compounds of the present invention have desirable selective inhibitory activity for EGFR mutant cells.

Moreover, in cytotoxicity experiments the compounds have a very weak inhibitory effect on NIH-3T3 cells, therebying showing lower cytotoxicity.

Therefore, such compounds have a good selective inhibitory activity on T790M mutant EGFR and a low cytotoxicity, making them ideal substitutes for the second generation EGFR-TKI. At the same time, the compounds of the present invention exhibit good bioavailability.

All literatures mentioned in the present application are incorporated herein by reference, as though each individually incorporated by reference. Additionally, it should be understood that after reading the above teachings, many variations and modifications may be made by the skilled in the art, and these equivalents also fall within the scope as defined by the appended claims.

The invention claimed is:

1. A compound represented by formula (I), or a pharmaceutically acceptable salt, solvate, or stereoisomer thereof:

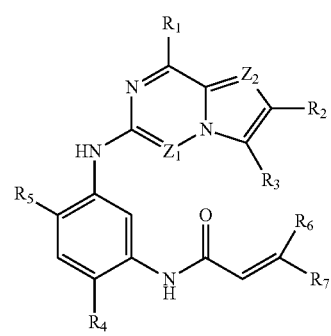

wherein;

each of $Z_1$ and $Z_2$ is independently N or $CR_0$, wherein $R_0$ is selected from the group consisting of H, halogen, $C_{1-10}$ alkyl, and $C_{1-10}$ haloalkyl;

each of $R_1$ and $R_2$ is independently H, halogen, $C_{1-10}$ alkyl, $C_{1-10}$ haloalkyl, $C_{1-10}$ alkoxy, or $C_{3-8}$ cycloalkoxy;

$R_3$ is $C_{1-10}$ alkyl, $C_{1-10}$ haloalkyl, substituted or unsubstituted $C_{3-10}$ cycloalkyl, substituted or unsubstituted $C_{6-10}$ aromatic ring, or substituted or unsubstituted $C_{4-10}$ cycloalkenyl,

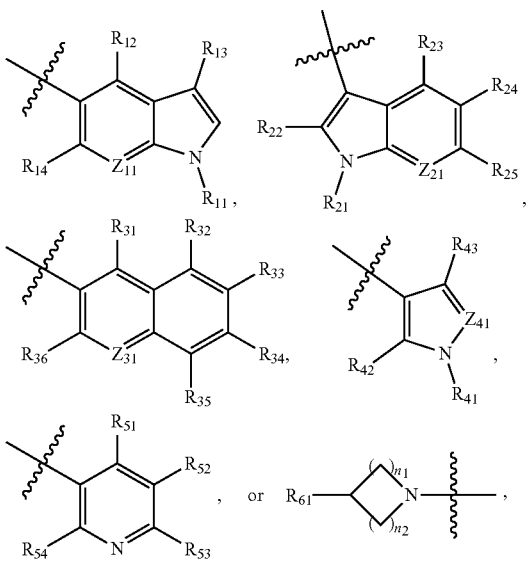

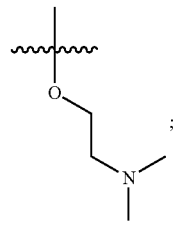

$R_5$ is methoxy; and each of $R_6$ and $R_7$.

2. The compound, or the pharmaceutically acceptable salt, solvate, or stereoisomer thereof according to claim 1, wherein $R_3$ is methyl, ethyl, propyl, isopropyl, monofluoroethyl, difluoromethyl, trifluoromethyl, cyclopropyl, cyclobutyl, cyclopentyl, cyclohexyl, substituted or unsubstituted phenyl, substituted or unsubstituted $C_{4-8}$ cycloalkenyl, wherein "substituted" means 1-6 hydrogen atoms on a ring atom are substituted with a substituent selected from the group consisting of hydroxy, CN, $NO_2$, halogen, $C_{1-10}$ alkyl, $C_{1-10}$ haloalkyl, —CON($C_{1-10}$ alkyl)$_2$, —C(O)O$C_{1-10}$ alkyl, —OC(O)$C_{1-10}$ alkyl, —CO$C_{1-10}$ alkyl, —CO-phenyl, —SO$_2$$C_{1-10}$ alkyl, —SO$_2$-phenyl, —S(O)$C_{1-10}$ alkyl, and —S(O)-phenyl, —N($C_{1-10}$ alkyl)$_2$ and wherein the phenyl is unsubstituted or substituted with 1-3 substituents selected from the group consisting of halogen and $C_{1-10}$ alkyl;

$Z_{11}$ is $CR_{15}$ or N;
$Z_{21}$ is $CR_{26}$ or N;
$Z_{31}$ is $CR_{37}$ or N;
$Z_{41}$ is $CR_{44}$ or N;
$n_1$ is 1, 2 or 3;
$n_2$ is 1 or 2;

each of $R_{12}$, $R_{13}$, $R_{14}$, $R_{15}$, $R_{22}$, $R_{23}$, $R_{24}$, $R_{25}$, $R_{26}$, $R_{31}$, $R_{32}$, $R_{33}$, $R_{34}$, $R_{35}$, $R_{36}$, $R_{37}$, $R_{42}$, $R_{43}$, $R_{44}$, $R_{51}$, $R_{52}$, $R_{53}$, $R_{54}$, and $R_{61}$ is independently H, hydroxy, CN, NO, halogen, $C_{1-10}$ haloalkyl, $C_{1-10}$ alkyl, —CON($C_{1-10}$ alkyl)$_2$, —N($C_{1-10}$ alkyl)$_2$, —C(O)O$C_{1-10}$ alkyl, —OC(O)$C_{1-10}$ alkyl, —CO$C_{1-10}$ alkyl, —CO-phenyl, —SO$_2$$C_{1-10}$ alkyl, —SO$_2$-phenyl, —S(O)$C_{1-10}$ alkyl, or —S(O)-phenyl, wherein the alkyl or phenyl is unsubstituted or substituted with 1-3 substituents selected from the group consisting of F, Cl, and methyl;

each of $R_{11}$, $R_{21}$, and $R_{41}$ is independently H, $C_{1-10}$ haloalkyl, $C_{1-10}$ alkyl, —CO$C_{1-10}$ alkyl, —CO-phenyl, —SO$_2$$C_{1-10}$ alkyl, or —SO$_2$-phenyl, wherein the phenyl is unsubstituted or substituted with 1-3 substituents selected from the group consisting of F, Cl, and methyl;

$R_4$ is selected from the group consisting of:

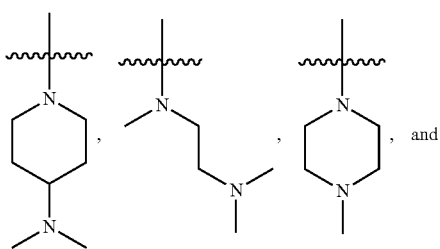

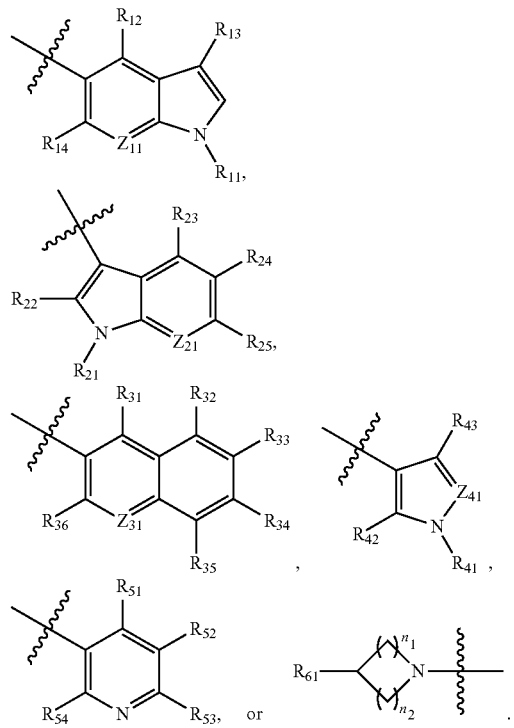

3. The compound, or the pharmaceutically acceptable salt, solvate, or stereoisomer thereof according to claim 1, wherein, $Z_{11}$ is N;

each of $R_{12}$, $R_{13}$, and $R_{14}$ is independently H, halogen, $C_{1-3}$ haloalkyl, or $C_{1-3}$ alkyl;

$R_{11}$ is H, $C_{1-3}$ haloalkyl, $C_{1-3}$ alkyl, —CO$C_{1-3}$ alkyl, or —SO$_2$$C_{1-3}$ alkyl;

$Z_{21}$ is $CR_{26}$;

each of $R_{22}$, $R_{23}$, $R_{24}$, $R_{25}$, and $R_{26}$ is independently H, halogen, $C_{1-3}$ haloalkyl, or $C_{1-3}$ alkyl; $R_{21}$ is H, $C_{1-3}$ haloalkyl, $C_{1-3}$ alkyl, —CO$C_{1-3}$ alkyl, or —SO$_2$$C_{1-3}$ alkyl;

$Z_{31}$ is N;

each of $R_{31}$, $R_{32}$, $R_{33}$, $R_{34}$, $R_{35}$, and $R_{36}$ is independently H, halogen, $C_{1-3}$ haloalkyl, or $C_{1-3}$ alkyl;

$Z_{41}$ is N or $CR_{44}$;

each of $R_{42}$, $R_{43}$, and $R_{44}$ is independently H, halogen, $C_{1-3}$ haloalkyl, or $C_{1-3}$ alkyl;

$R_{41}$ is H, $C_{1-3}$ haloalkyl, $C_{1-3}$ alkyl, —$COC_{1-3}$ alkyl, or —$SO_2C_{1-3}$ alkyl;

each of $R_{51}$, $R_{52}$, $R_{53}$, and $R_{54}$ is independently H, halogen, $C_{1-3}$ haloalkyl, or $C_{1-3}$ alkyl;

$n_1$ is 2;

$n_2$ is 2; and $R_{61}$ is H, halogen, $C_{1-3}$ haloalkyl, $C_{1-3}$ alkyl, —$COC_{1-3}$ alkyl, or —$SO_2C_{1-3}$ alkyl.

4. The compound, or the pharmaceutically acceptable salt, solvate, or stereoisomer thereof according to claim 3, wherein, $Z_{11}$ is N;

each of $R_{12}$, $R_{13}$, and $R_{14}$ is independently H, F, Cl, Br, methyl, ethyl, propyl, isopropyl, monofluoroethyl, difluoromethyl, or trifluoromethyl;

$R_{11}$ is H, methyl, ethyl, propyl, isopropyl, monofluoroethyl, difluoromethyl, trifluoromethyl, —$COCH_3$, or —$SO_2CH_3$;

$Z_{21}$ is $CR_{26}$;

each of $R_{22}$, $R_{23}$, $R_{24}$, $R_{25}$, and $R_{26}$ is independently H, F, Cl, Br, methyl, ethyl, propyl, isopropyl, monofluoroethyl, difluoromethyl, or trifluoromethyl;

$R_{21}$ is H, methyl, ethyl, propyl, isopropyl, monofluoroethyl, difluoromethyl, trifluoromethyl, —$COCH_3$, or —$SO_2CH_3$;

$Z_{31}$ is N;

each of $R_{31}$, $R_{32}$, $R_{33}$, $R_{34}$, $R_{35}$, and $R_{36}$ is independently H, F, Cl, Br, methyl, ethyl, propyl, isopropyl, monofluoroethyl, difluoromethyl, or trifluoromethyl;

$Z_{41}$ is N or $CR_{44}$;

each of $R_{42}$, $R_{43}$, and $R_{44}$ is independently H, F, Cl, Br, methyl, ethyl, propyl, isopropyl, monofluoroethyl, difluoromethyl, or trifluoromethyl;

$R_{41}$ is H, methyl, ethyl, propyl, isopropyl, monofluoroethyl, difluoromethyl, trifluoromethyl, —$COCH_3$, or —$SO_2CH_3$;

each of $R_{51}$, $R_{52}$, $R_{53}$, and $R_{54}$ is independently H, F, Cl, Br, methyl, ethyl, propyl, isopropyl, monofluoroethyl, difluoromethyl, or trifluoromethyl;

$n_1$ is 2;

$n_2$ is 2; and $R_{61}$ is H, F, Cl, Br, methyl, ethyl, propyl, isopropyl, monofluoroethyl, difluoromethyl, trifluoromethyl, —$COCH_3$, or —$SO_2CH_3$.

5. The compound, or the pharmaceutically acceptable salt, solvate, or stereoisomer thereof according to claim 1, wherein the compound of formula (I) is a compound of formula (II), formula (III), formula (IV), formula (V), formula (VI), formula (VII), formula (VIII), or formula (IX), or a pharmaceutically acceptable salt, solvate, or stereoisomer thereof:

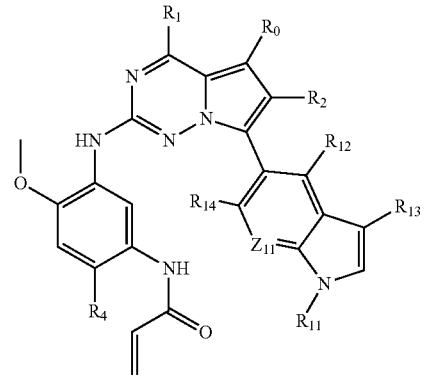

II wherein $R_{11}$, $R_{12}$, $R_{13}$, $R_{14}$, $Z_{11}$, $R_0$, $R_1$, $R_2$, and $R_4$ are defined as in claim 1;

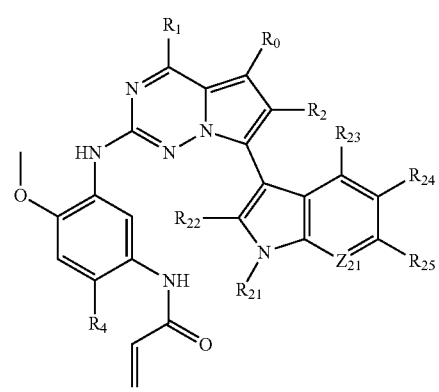

III wherein $R_{21}$, $R_{22}$, $R_{23}$, $R_{24}$, $R_{25}$, $Z_{21}$, $R_0$, $R_1$, $R_2$, and $R_4$ are defined as in claim 1;

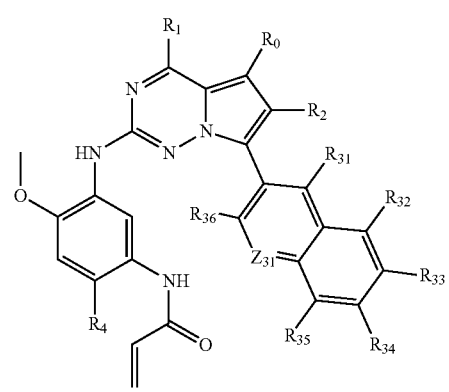

IV wherein $R_{31}$, $R_{32}$, $R_{33}$, $R_{34}$, $R_{35}$, $R_{36}$, $Z_{31}$, $R_0$, $R_1$, $R_2$, and $R_4$ are defined as in claim 1;

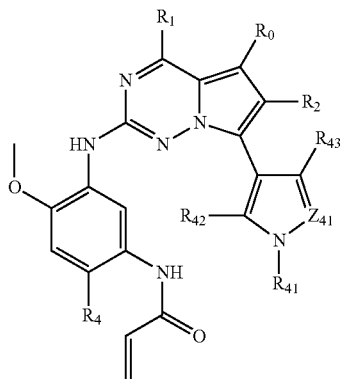

V wherein $R_{41}$, $R_{42}$, $R_{43}$, $Z_{41}$, $R_0$, $R_1$, $R_2$, and $R_4$ are defined as in claim 1;

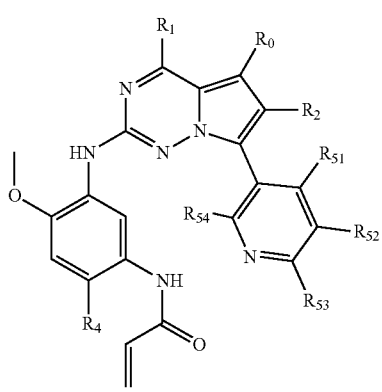

VI wherein $R_{51}$, $R_{52}$, $R_{53}$, $R_{54}$, $R_0$, $R_1$, $R_2$, and $R_4$ are defined as in claim 1;

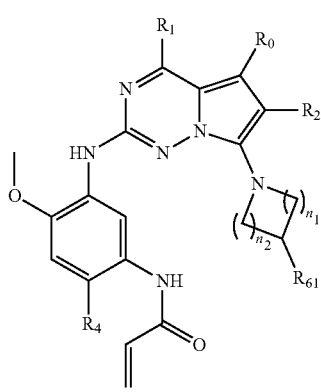

VII wherein $R_{61}$, $n_1$, $n_2$, $R_0$, $R_1$, $R_2$, and $R_4$ are defined as in claim 1;

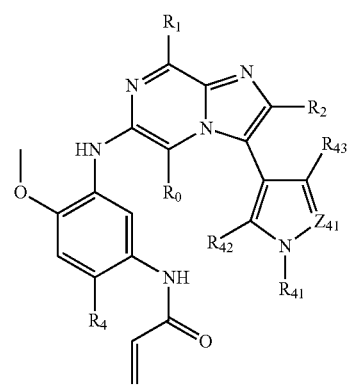

VIII wherein $R_{41}$, $R_{42}$, $R_{43}$, $Z_{41}$, $R_0$, $R_1$, $R_2$, and $R_4$ are defined as in claim 1;

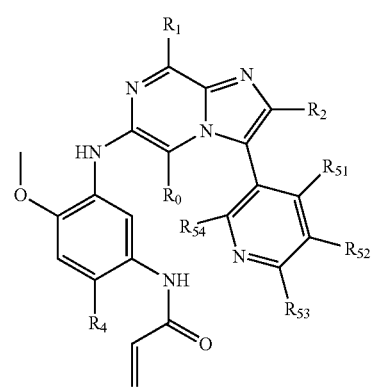

IX wherein $R_{51}$, $R_{52}$, $R_{53}$, $R_{54}$, $R_0$, $R_1$, $R_2$, and $R_4$ are defined as in claim 1.

6. A compound selected from the group consisting of:

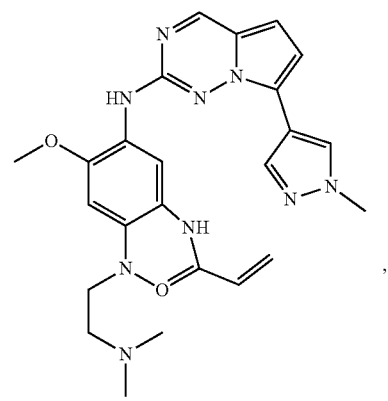

,

101
-continued
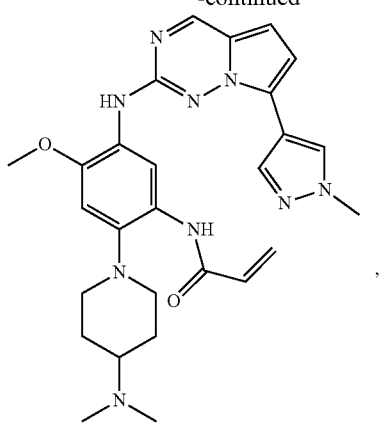
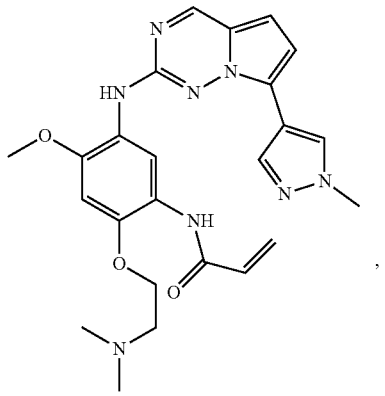
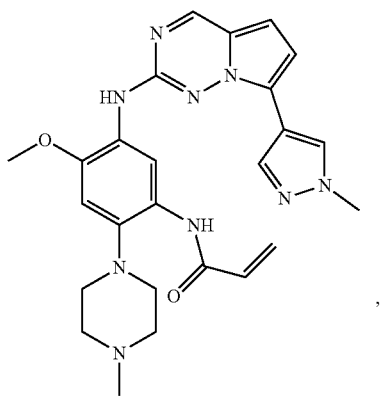
102
-continued
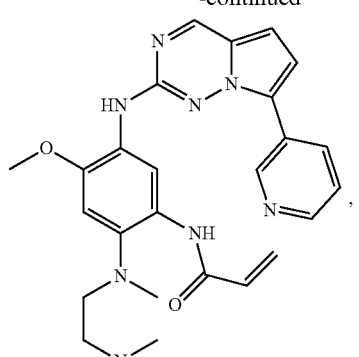
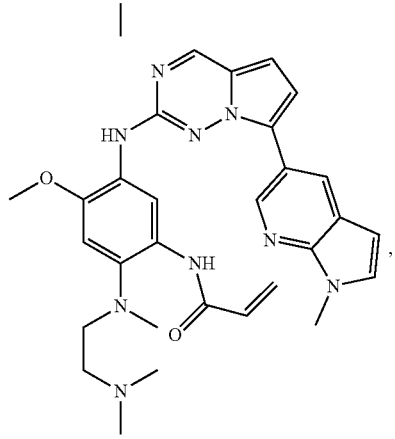
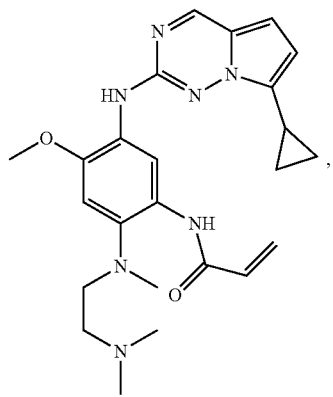
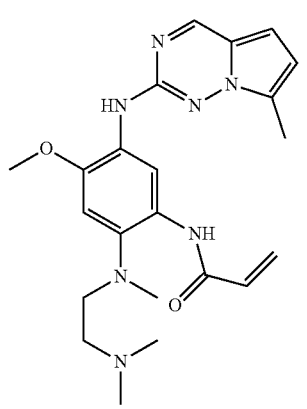

103
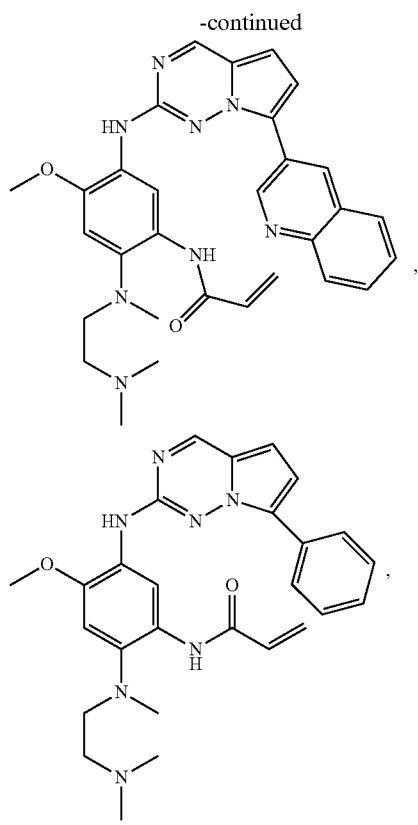
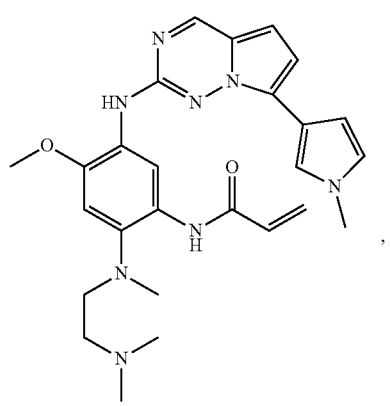
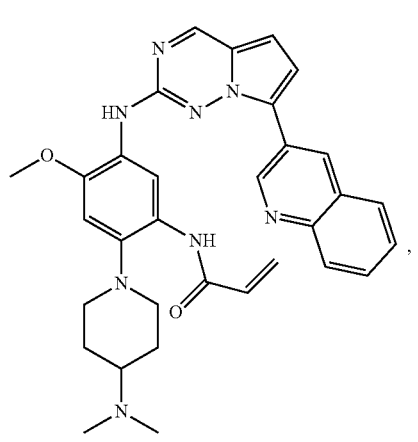
104
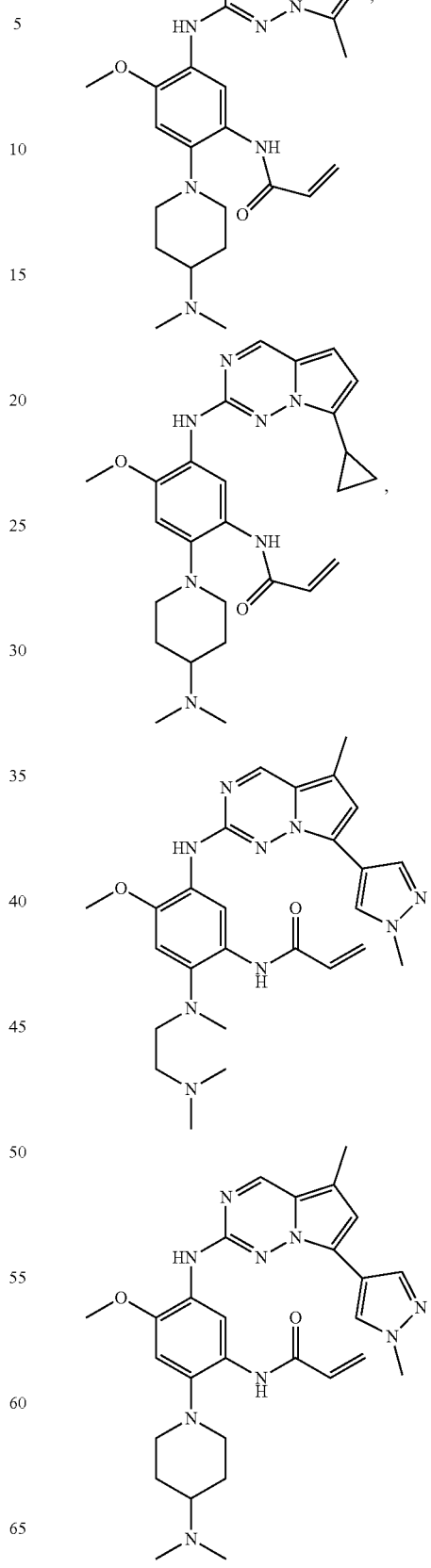

105
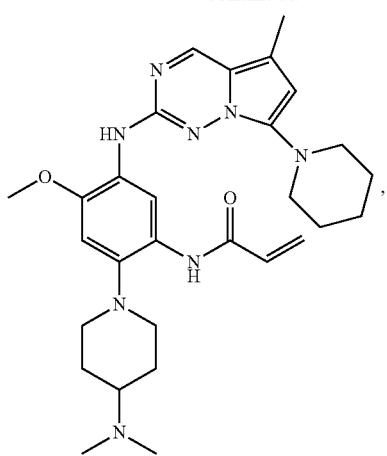
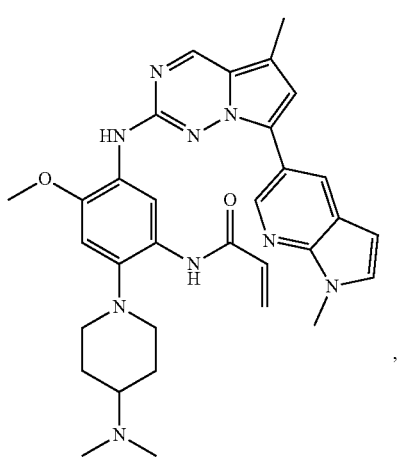
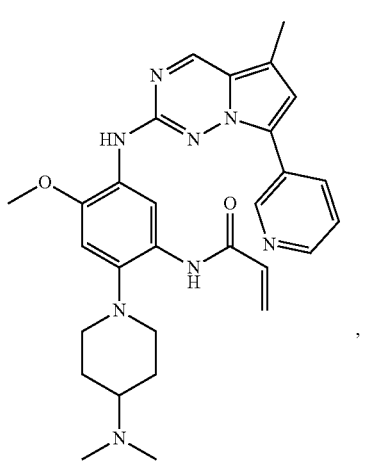
106
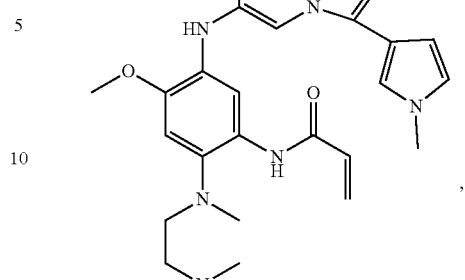
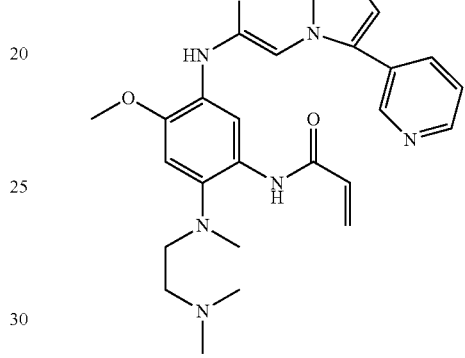
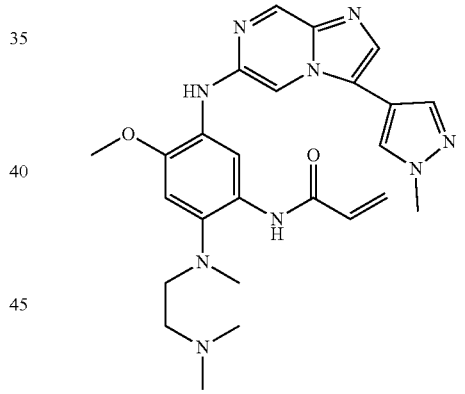
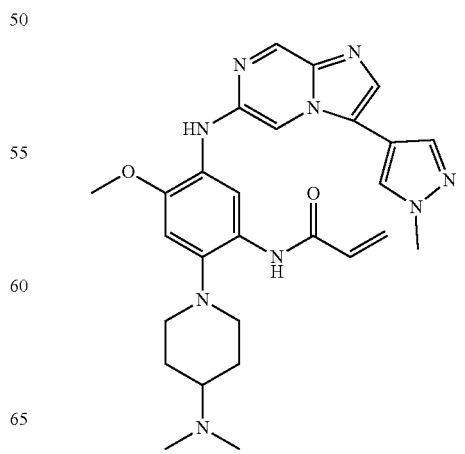

107
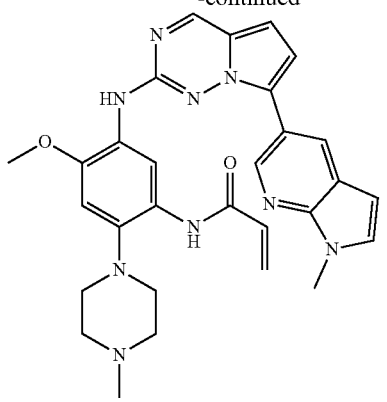
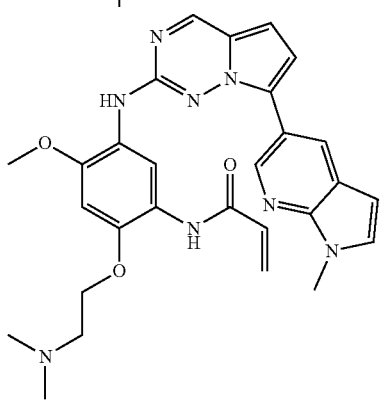
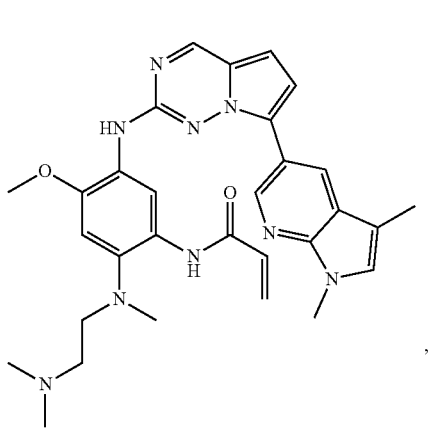
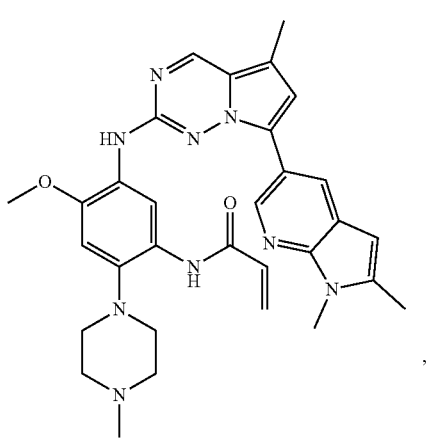
108
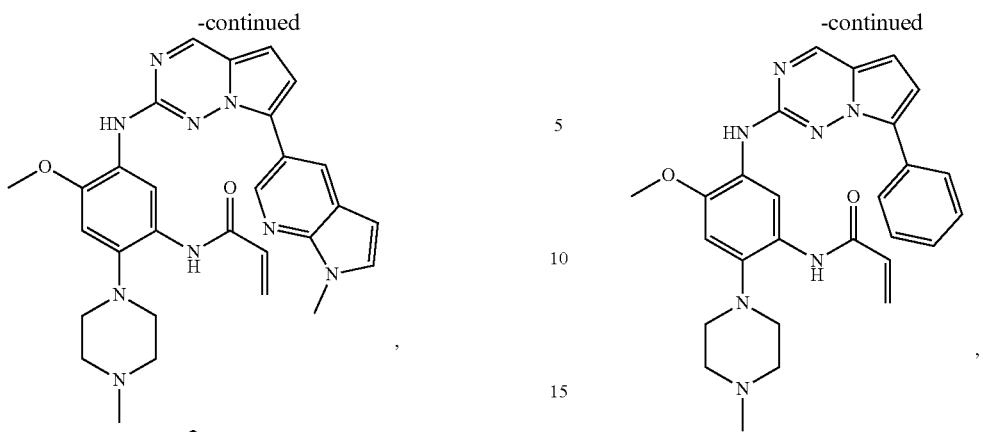
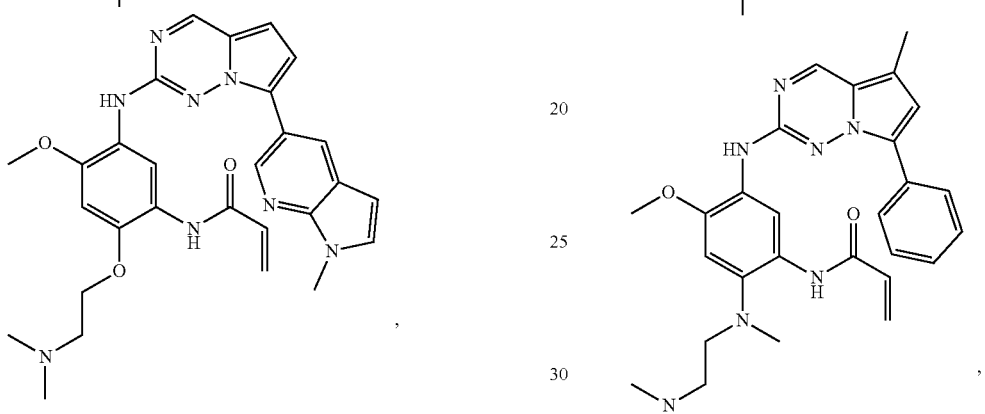
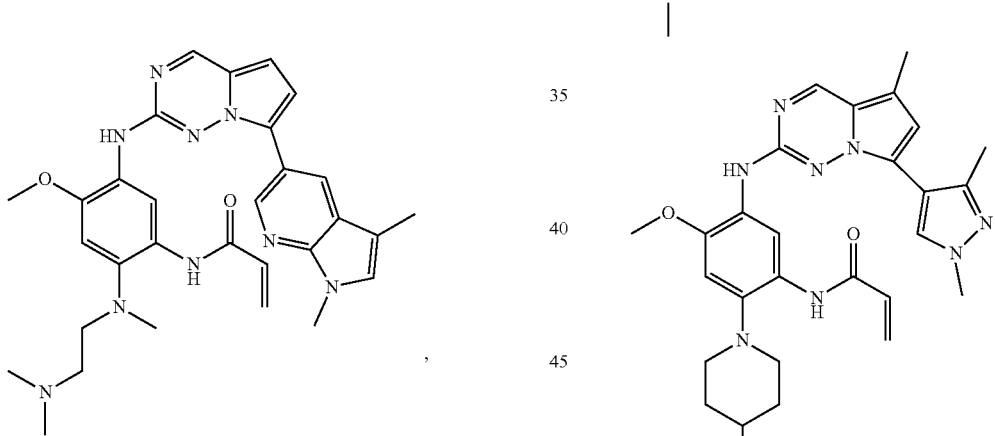
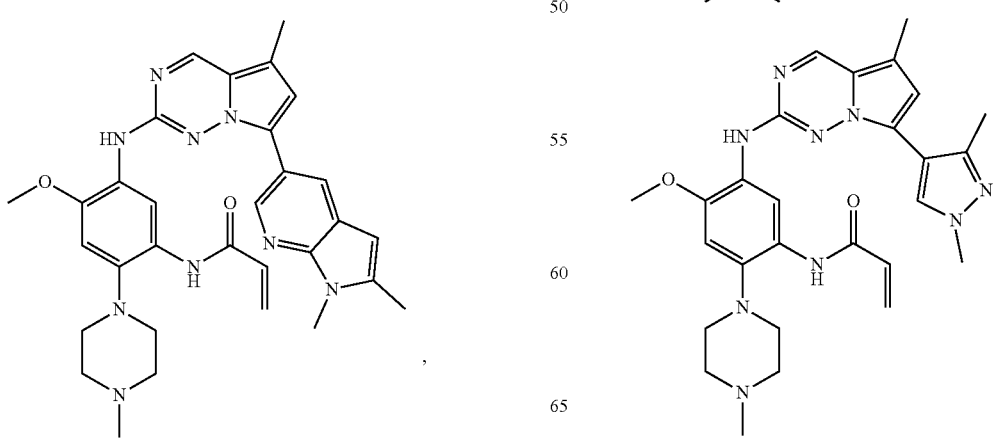

109
-continued
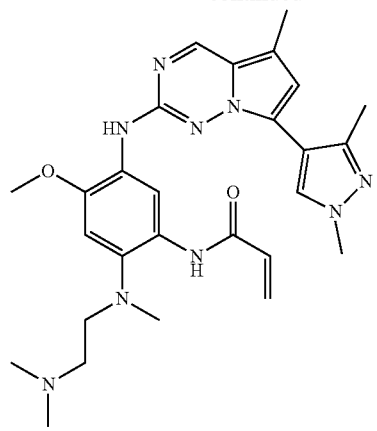
,
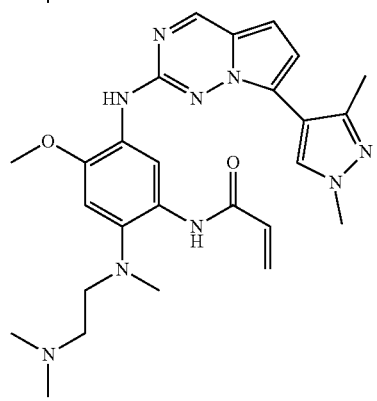
,
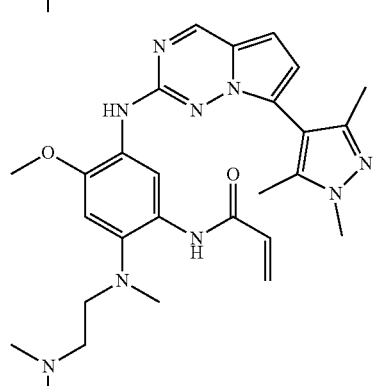
,
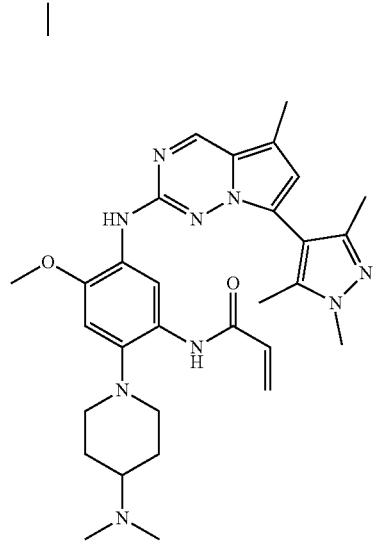
,
110
-continued
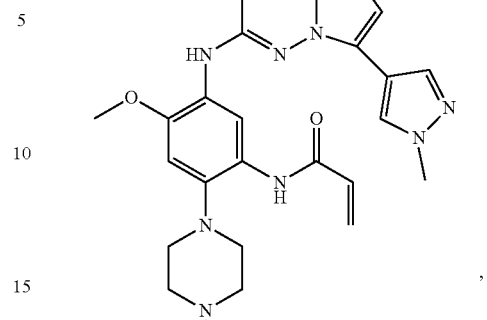
,
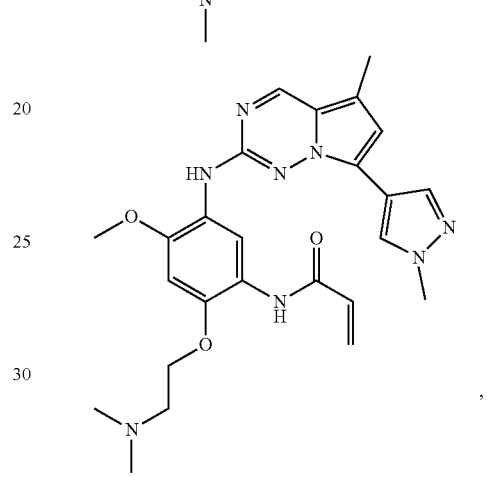
,
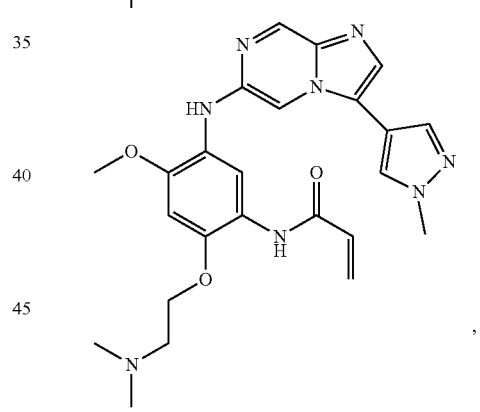
, 111
-continued
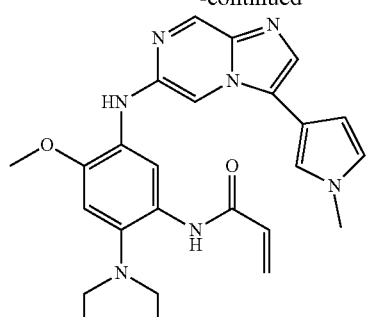
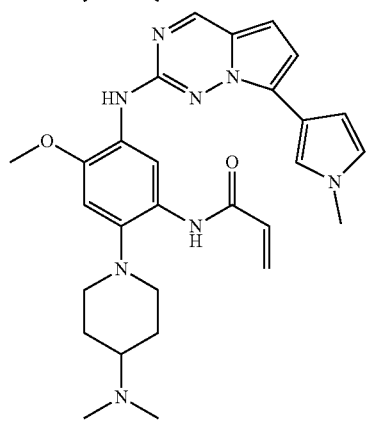
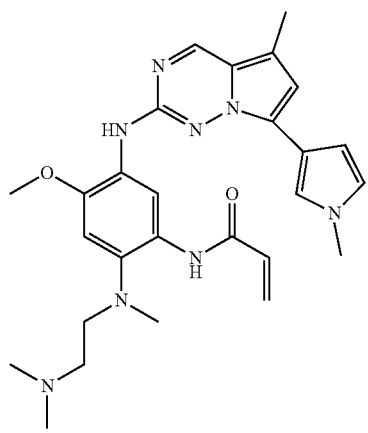
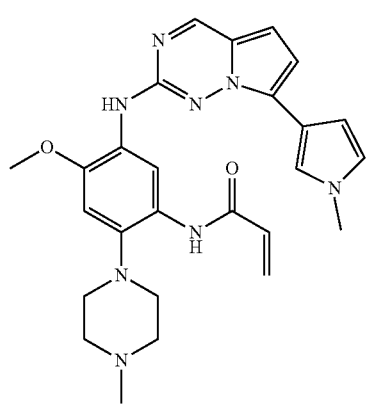
112
-continued
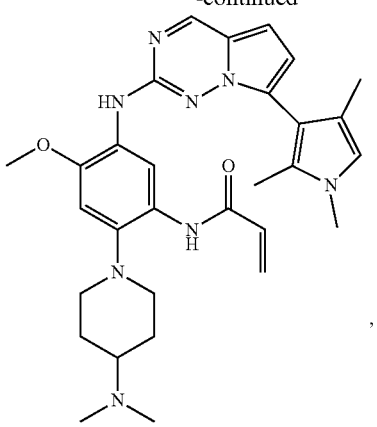
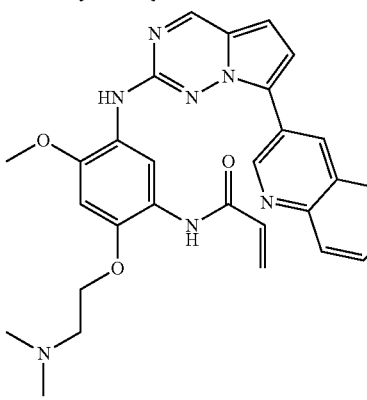
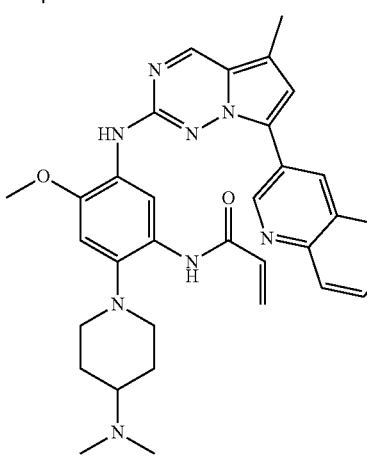
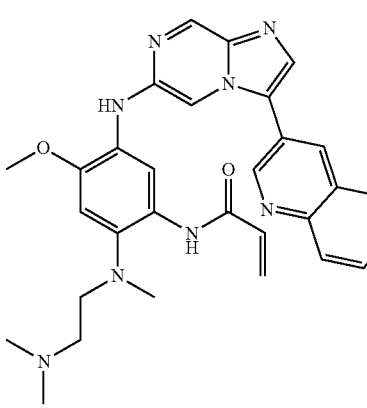

-continued

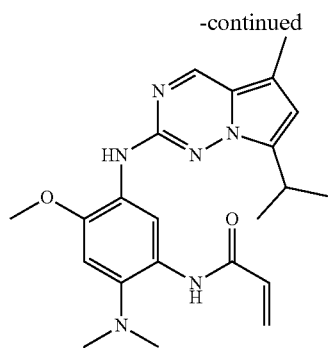

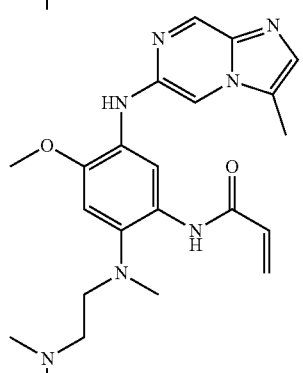

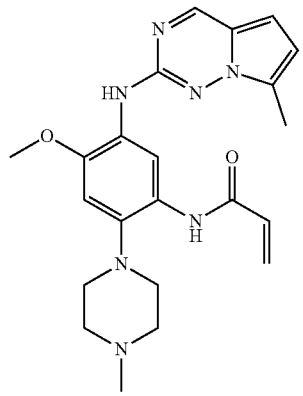

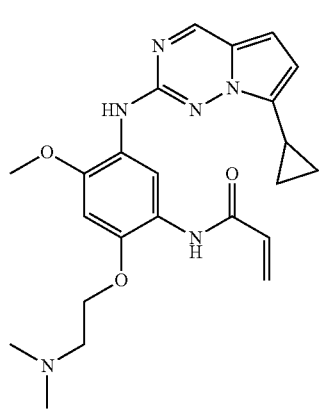

-continued

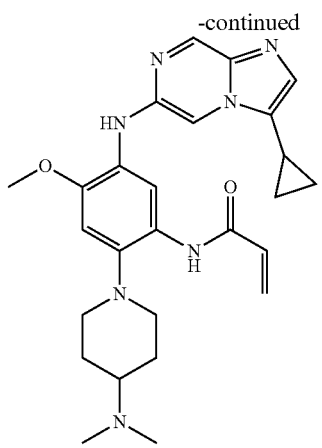

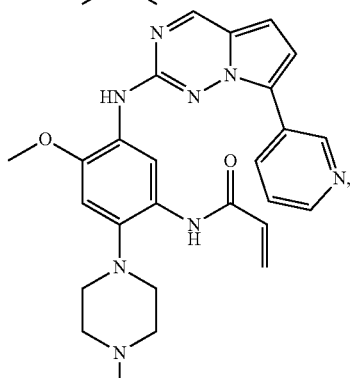

, and

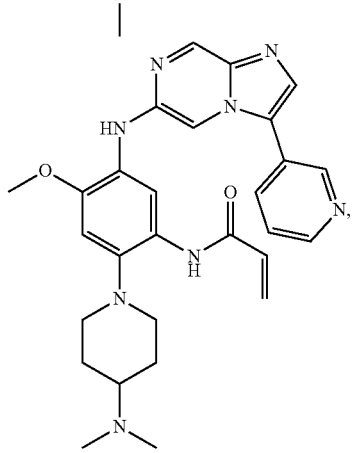

or a pharmaceutically acceptable salt, solvate or stereoisomer thereof.

7. A pharmaceutical composition comprising the compound, or the pharmaceutically acceptable salt, solvate, or stereoisomer thereof according to claim 1, and a pharmaceutically acceptable carrier.

8. A method for treating an EGFR-related disease in a subject, the method comprising administering to the subject the pharmaceutical composition of claim 7, wherein the EGFR-related disease is non-small cell lung cancer.

9. A medicinal composition comprising the compound, or the pharmaceutically acceptable salt, solvate, or stereoisomer thereof according to claim 1 and an additional medicament, wherein the additional medicament is at least one medicament selected from the group consisting of gefitinib, erlotinib, icotinib, lapatinib, XL647, NVP-AEE-788, ARRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitors, CNF2024, tanespimycin, alvespimycin, IPI-504, SNX-5422, and NVP-AUY922.

10. A pharmaceutical composition comprising the compound, or pharmaceutically acceptable salt, solvate, or stereoisomer thereof according to claim 6, and a pharmaceutically acceptable carrier.

11. A method for treating an EGFR-related disease in a subject, the method comprising administering to the subject the pharmaceutical composition according to claim 10, wherein the EGFR-related disease is non-small cell lung cancer.

12. The method according to claim 8, wherein the non-small cell lung cancer is caused by mutations of EFGR comprising L858R and T790M.

13. The method according to claim 11, wherein the non-small cell lung cancer is caused by mutations of EGFR comprising L858R and T790M.

* * * * *